(12) United States Patent
Bai

(10) Patent No.: US 12,082,501 B2
(45) Date of Patent: Sep. 3, 2024

(54) ORGANIC COMPOUND, PREPARATION METHOD THEREOF, AND DISPLAY PANEL

(71) Applicant: WUHAN CHINA STAR OPTOELECTRONICS SEMICONDUCTOR DISPLAY TECHNOLOGY CO., LTD., Wuhan (CN)

(72) Inventor: Keyan Bai, Wuhan (CN)

(73) Assignee: WUHAN CHINA STAR OPTOELECTRONICS SEMICONDUCTOR DISPLAY TECHNOLOGY CO., LTD., Wuhan (CN)

( * ) Notice: Subject to any disclaimer, the term of this patent is extended or adjusted under 35 U.S.C. 154(b) by 681 days.

(21) Appl. No.: 17/420,109

(22) PCT Filed: May 24, 2021

(86) PCT No.: PCT/CN2021/095430
§ 371 (c)(1),
(2) Date: Jun. 30, 2021

(87) PCT Pub. No.: WO2022/205588
PCT Pub. Date: Oct. 6, 2022

(65) Prior Publication Data
US 2023/0157163 A1    May 18, 2023

(30) Foreign Application Priority Data
Mar. 29, 2021   (CN) .......................... 202110335161.6

(51) Int. Cl.
| | |
|---|---|
| *C07D 471/06* | (2006.01) |
| *C09K 11/06* | (2006.01) |
| *H10K 50/16* | (2023.01) |
| *H10K 85/60* | (2023.01) |

(52) U.S. Cl.
CPC ....... *H10K 85/6572* (2023.02); *C07D 471/06* (2013.01); *C09K 11/06* (2013.01); *H10K 85/657* (2023.02); *C09K 2211/1018* (2013.01); *H10K 50/16* (2023.02)

(58) Field of Classification Search
CPC ............. H10K 85/6572; H10K 85/657; H10K 50/16; C07D 471/06; C09K 11/06; C09K 2211/1018
See application file for complete search history.

(56) References Cited

U.S. PATENT DOCUMENTS 11,101,435 B2 *   8/2021   Li ....................... C07F 15/0086

FOREIGN PATENT DOCUMENTS

| CN | 109942578 A | 6/2019 |
|---|---|---|
| CN | 111187263 A | 5/2020 |
| CN | 111763205 A | 10/2020 |
| CN | 110590790 B | 12/2020 |
| CN | 112062764 A | 12/2020 |

* cited by examiner

*Primary Examiner* — Timothy R Rozof
(74) *Attorney, Agent, or Firm* — The Roy Gross Law Firm, LLC; Roy Gross

(57) ABSTRACT

Embodiments of the present invention disclose an organic compound, a preparation method thereof, and a display panel. The organic compound is represented by the following general formula:

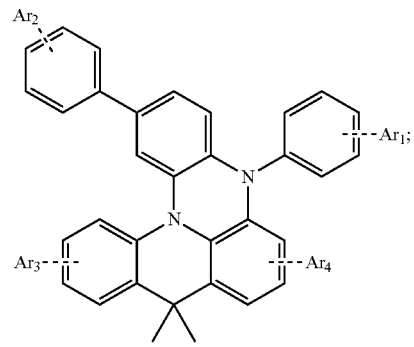

wherein a structure of the organic compound includes at least one of Ar1, Ar2, Ar3, or Ar4, any one of Ar1, Ar2, Ar3 and Ar4 includes any one or a combination of hydrogen, an isotope of hydrogen, an aromatic group, an arylamine group, a heteroarylamine group, and a fused ring group. In the embodiments of the present invention, by adding other electron-donating groups on the basis of a structure of phenazine acridine, organic compounds with high mobility are obtained.

20 Claims, 1 Drawing Sheet

ORGANIC COMPOUND, PREPARATION METHOD THEREOF, AND DISPLAY PANEL

CROSS REFERENCE TO RELATED APPLICATIONS

This application is a National Phase of PCT Patent Application No. PCT/CN2021/095430 having International filing date of May 24, 2021, which claims the benefit of priority of Chinese Application No. 202110335161.6 filed on Mar. 29, 2021. The contents of the above applications are all incorporated by reference as if fully set forth herein in their entirety.

BACKGROUND OF INVENTION

Field of Invention

The present application relates to the field of display, and in particular to an organic compound, a preparation method thereof, and a display panel.

Description of Prior Art

In recent years, organic light-emitting diode (OLED) display panels have become more and more popular in the market.

At present, in the OLED display panels, energy levels and mobility of materials of light-emitting device layers have always been in contradictory relationships, and it is urgent to develop materials for the light-emitting device layers with matching energy levels and high mobility.

Therefore, there is an urgent need to provide an organic compound, a preparation method thereof, and a display panel to solve the above technical problems.

SUMMARY OF INVENTION

Embodiments of the present application provide an organic compound and a preparation method thereof, and a display panel, to alleviate the technical problem of low mobility of materials for light-emitting device layers.

In order to solve the above problems, the technical solutions provided by the present application are as follows:

Embodiments of the present application provide an organic compound, and the organic compound is represented by the following g general formula:

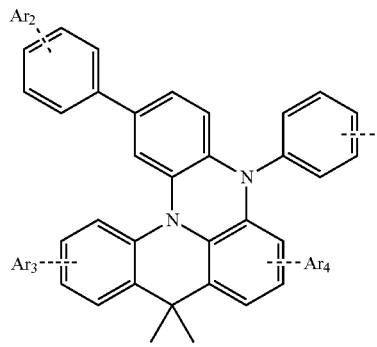

wherein any one of $Ar_1$, $Ar_2$, $Ar_3$, and $Ar_4$ includes any one or a combination of hydrogen, an isotope of hydrogen, an aromatic group, an arylamine group, a heteroarylamine group, and a fused ring group.

In one embodiment, any one of $Ar_1$, $Ar_2$, $Ar_3$, and $Ar_4$ includes any one or a combination of protium, deuterium, tritium, an aromatic group with 6 to 60 carbon atoms, an arylamine group with 6 to 60 carbon atoms, a heteroarylamine group with 6 to 60 carbon atoms, and a fused ring group with 10 to 60 carbon atoms.

In one embodiment, any one of $Ar_1$, $Ar_2$, $Ar_3$, and $Ar_4$ is an axisymmetric group containing a benzene ring.

In one embodiment, any one of $Ar_1$, $Ar_2$, $Ar_3$, and $Ar_4$ is any one or a combination of the following groups:

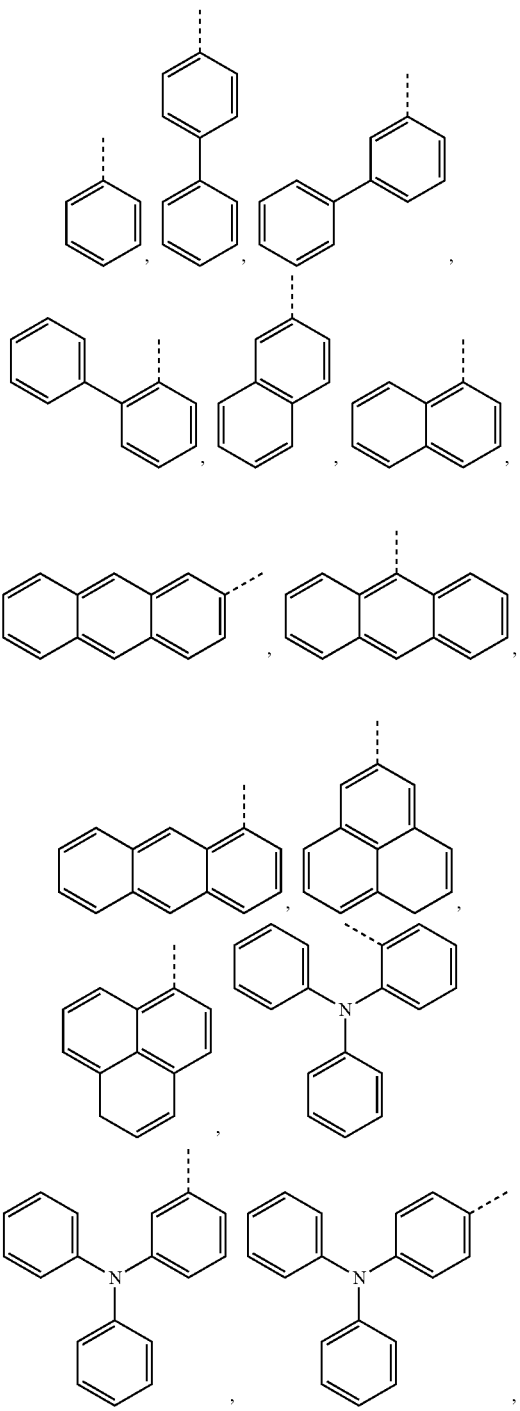

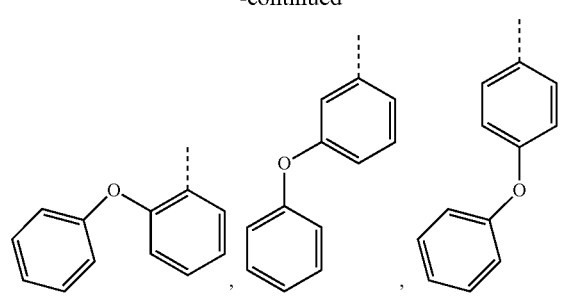
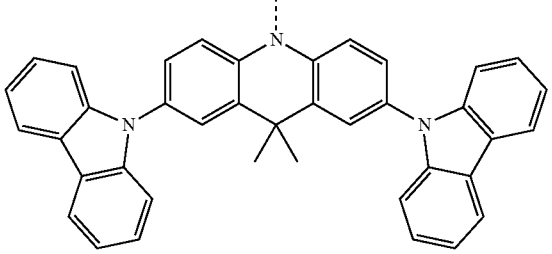
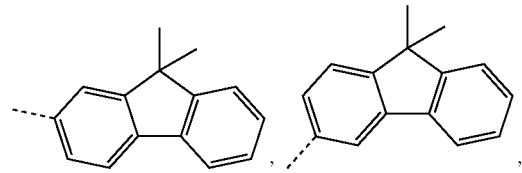
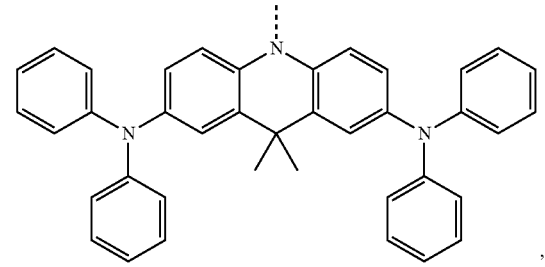
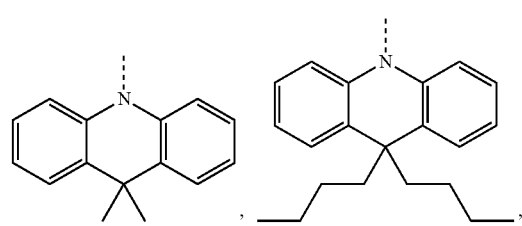
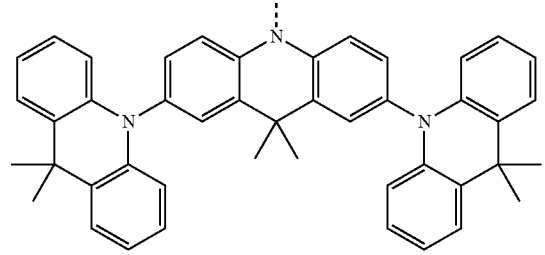
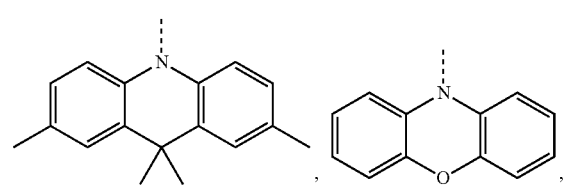
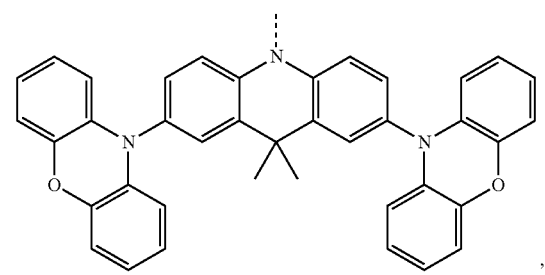
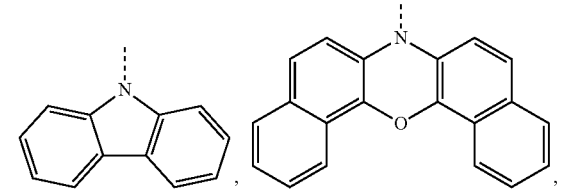
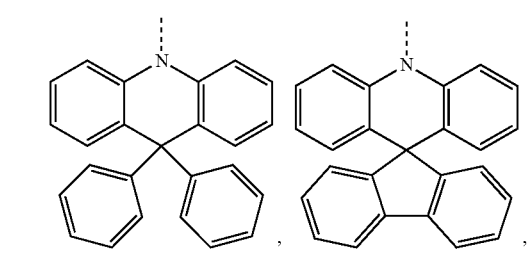
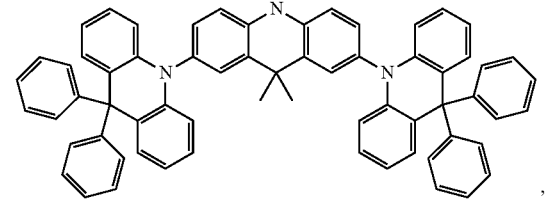
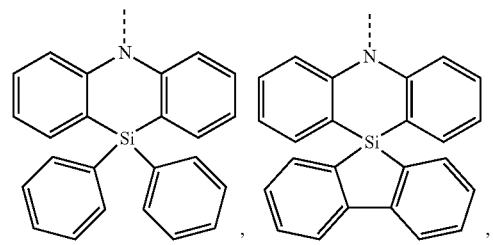
, and

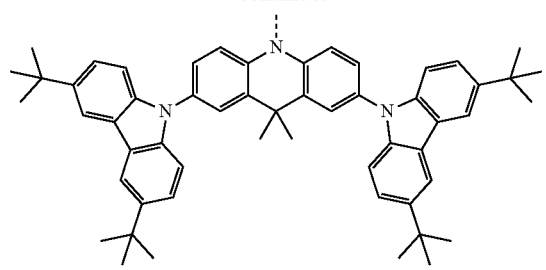

In one embodiment, the aromatic group includes an oxygen-containing aromatic group or a silicon-containing aromatic group, the arylamine group includes an oxygen-containing arylamine group or a silicon-containing arylamine group, and the fused ring group includes any one of naphthalene, anthracene, and pyrene.

In one embodiment, any one of Ar1, Ar2, Ar3, and Ar4 is any one or a combination of the following groups:

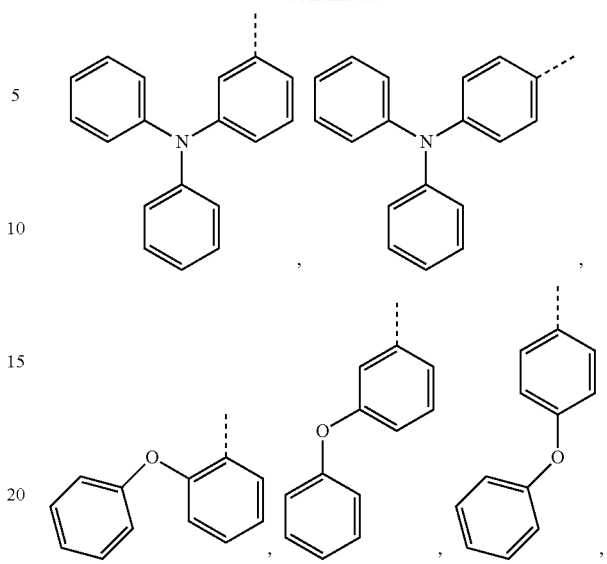

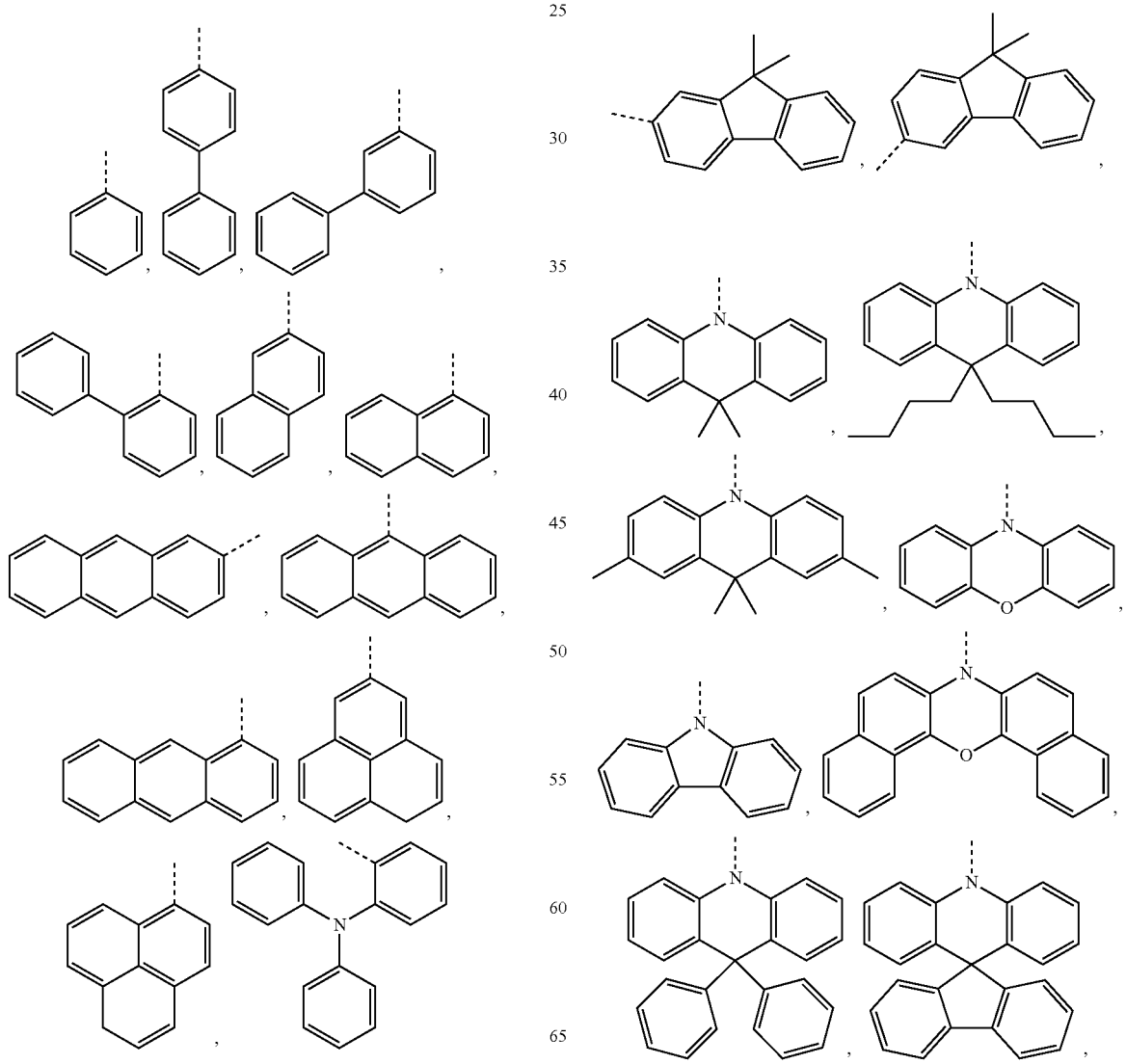

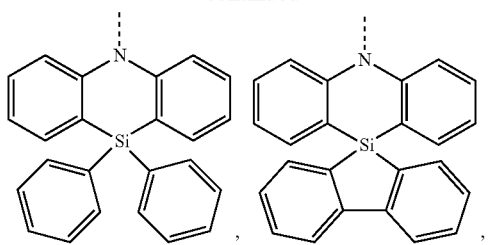 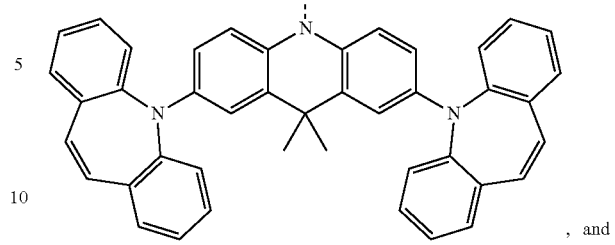
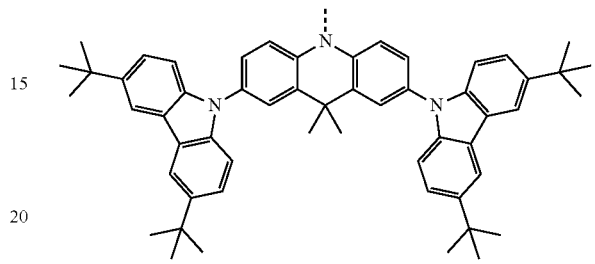
, and
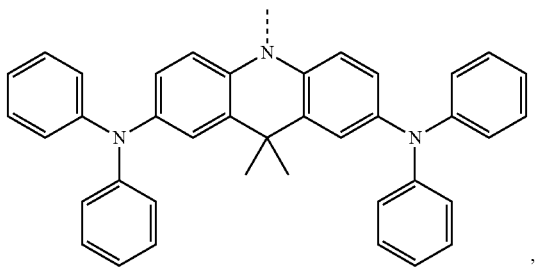 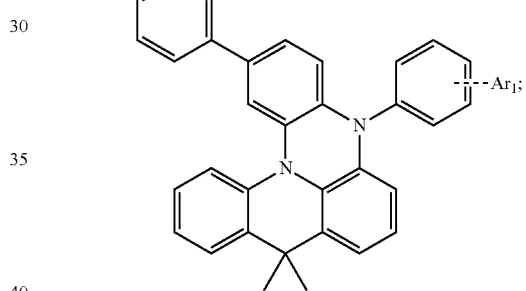
In one embodiment, a structural formula of the organic compound is:
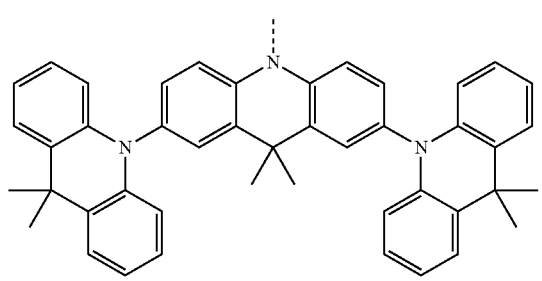
wherein Ar1 is any one of an aromatic group, an arylamine group, or a heteroarylamine group.
In one embodiment, Ar1 is any one of the following groups:
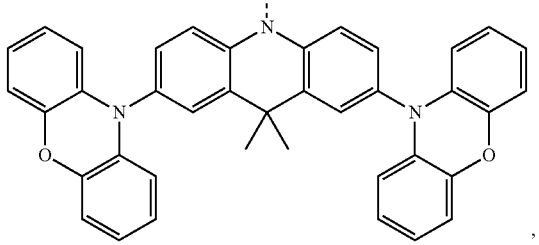 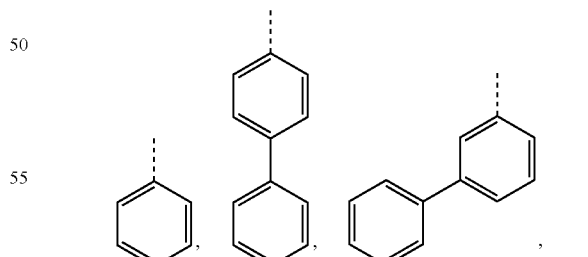
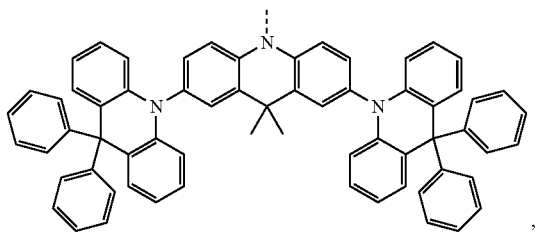 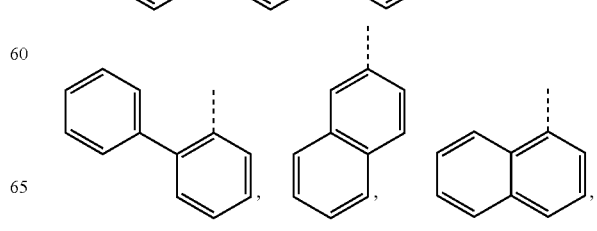

-continued
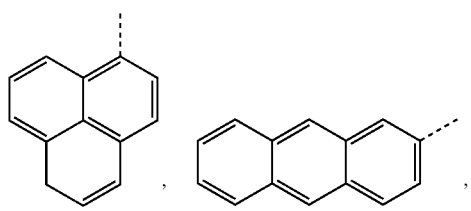
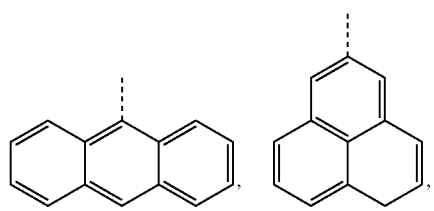
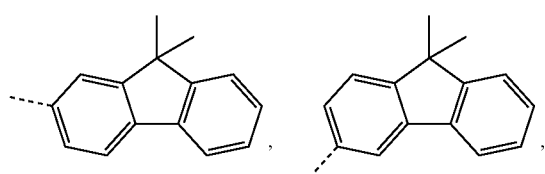
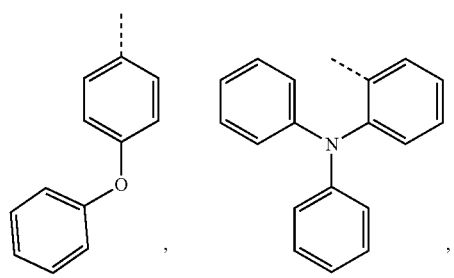
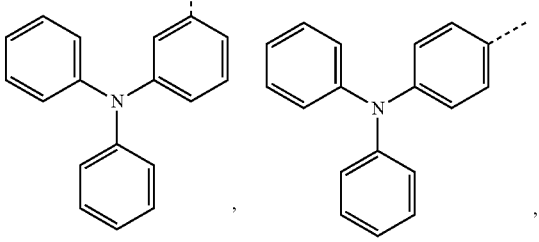
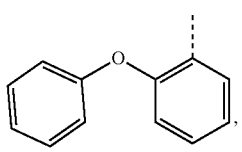
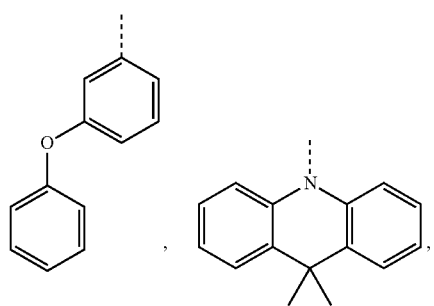
-continued
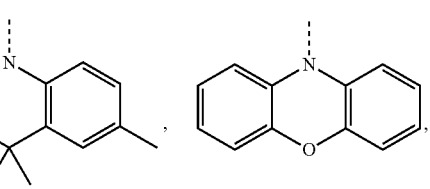
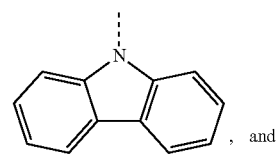
, and
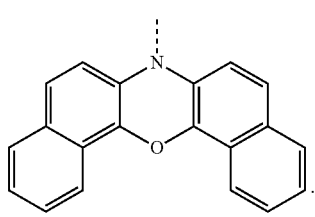
In one embodiment, a structure of the organic compound includes any one or a combination of the following:
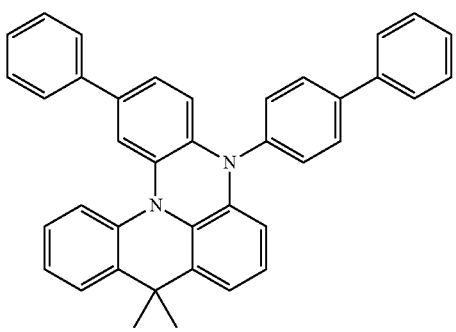
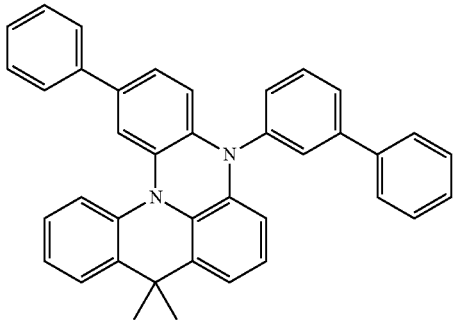

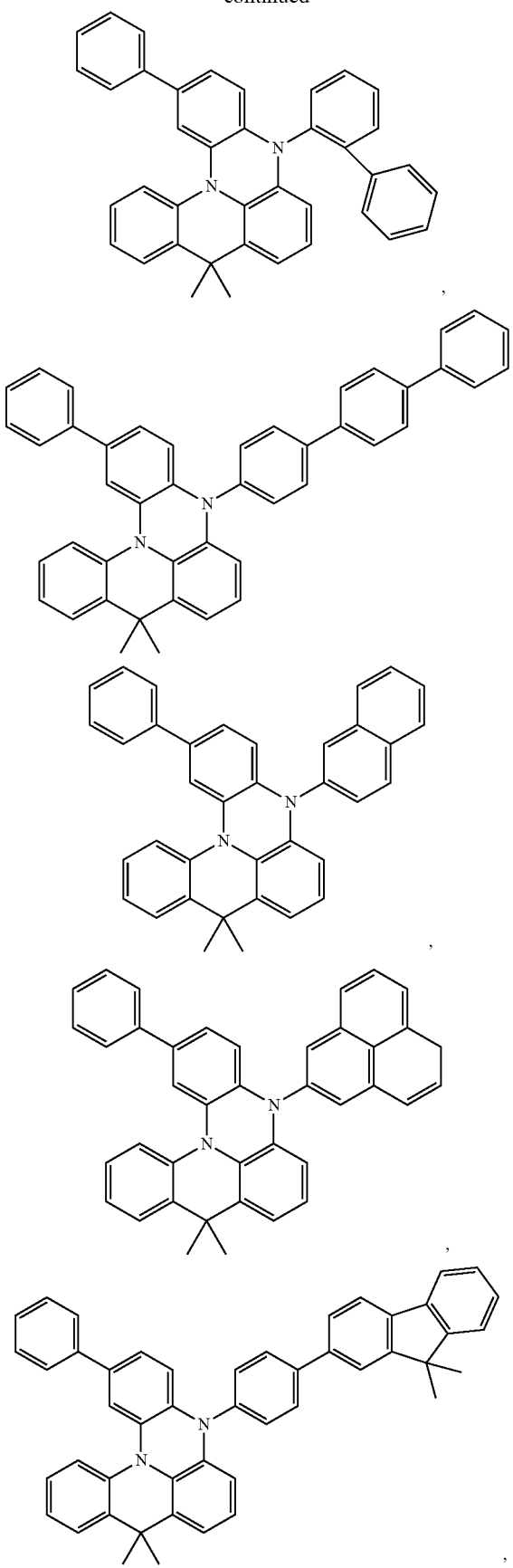
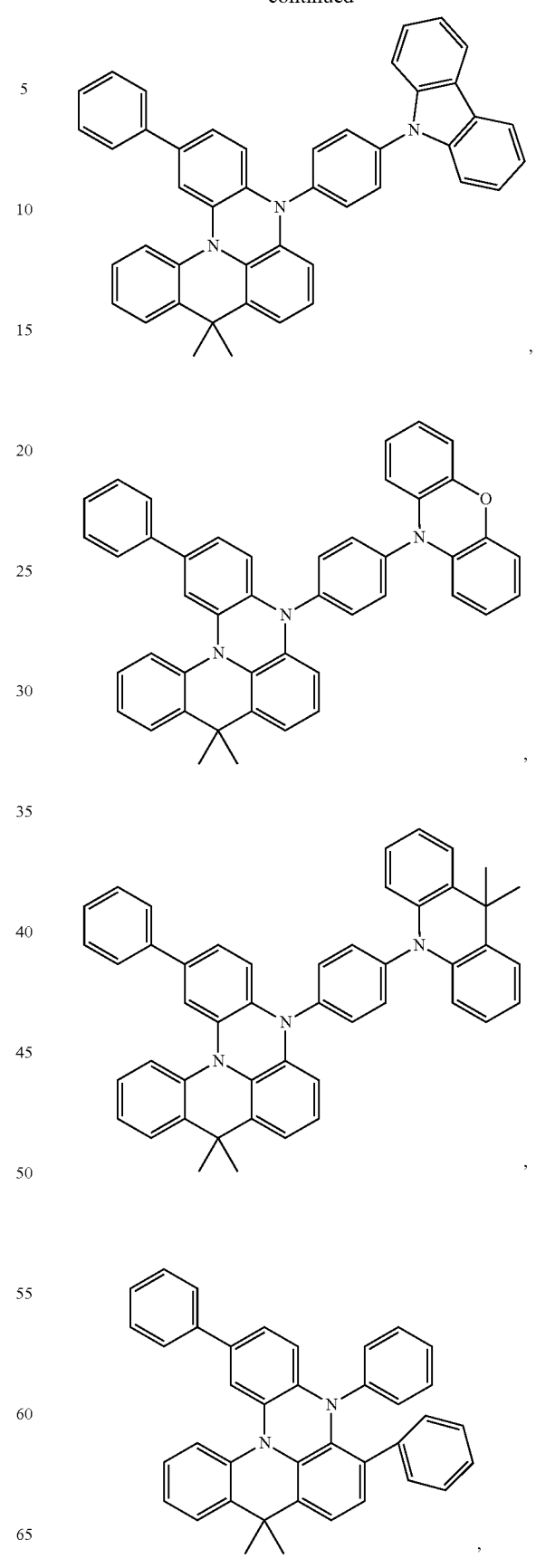

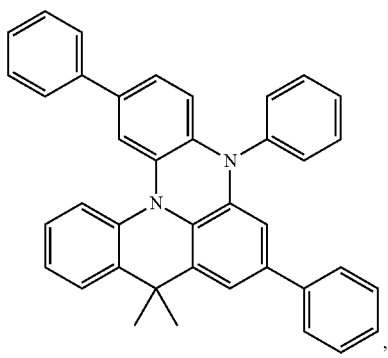,
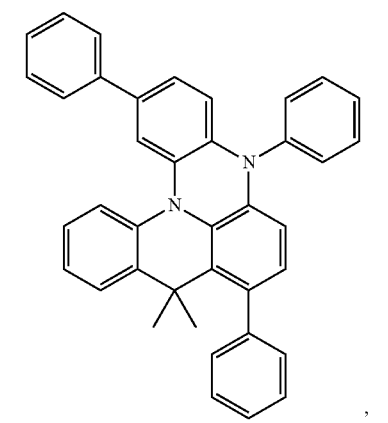,
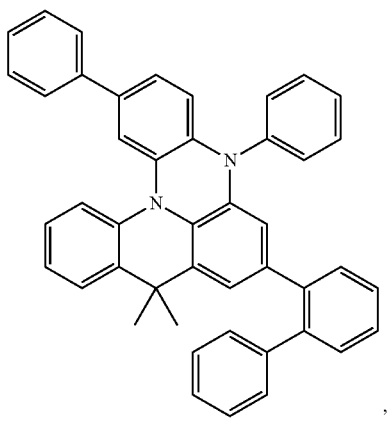,
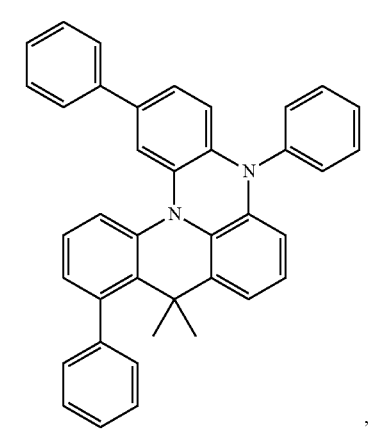,
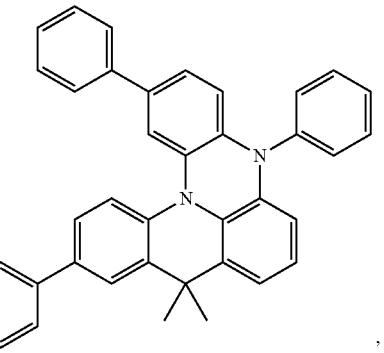,
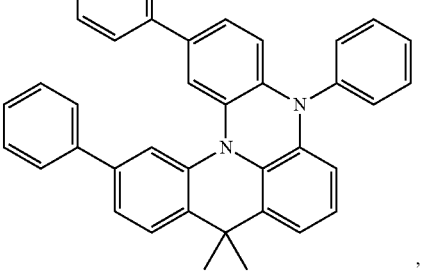,
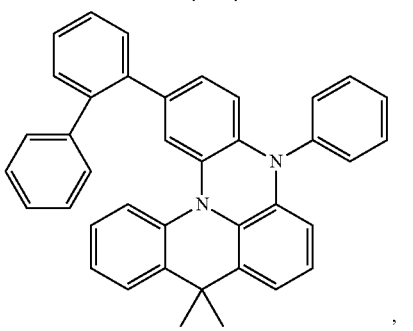,
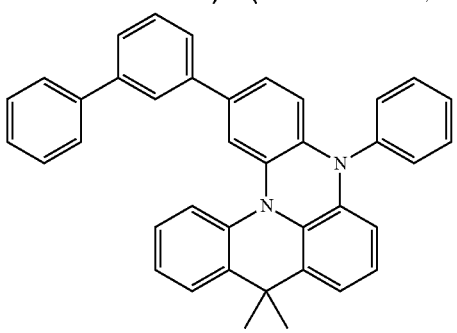,
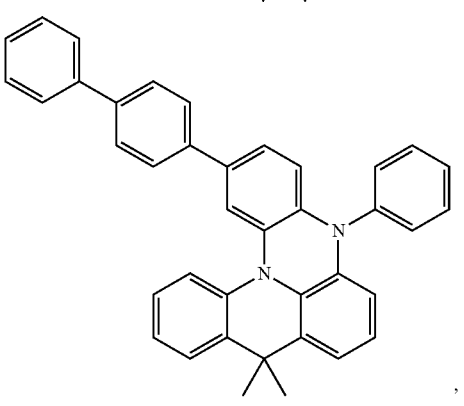, and -continued

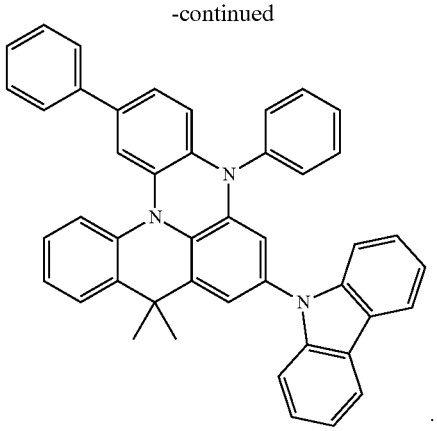

Another embodiment of the present application further provides a method of preparing an organic compound, including:
mixing a first material and a second material to form the organic compound, and the organic compound is represented by the general formula (1):

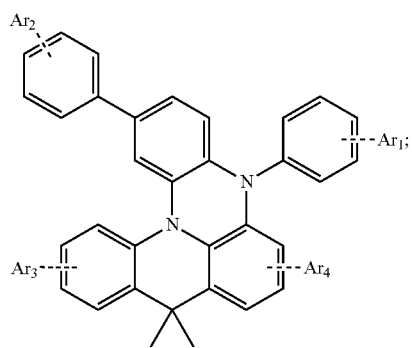

the first material is represented by the general formula (2):

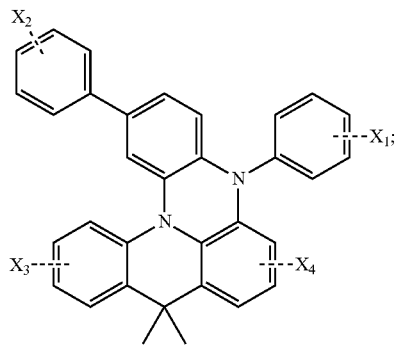

wherein the second material includes any one or a combination of an aromatic group, an arylamine group, a heteroarylamine group, and a fused ring group; each of X1, X2, X3, and X4 is halogen; a structure of the first material includes at least one of X1, X2, X3, and X4; and any one of Ar1, Ar2, Ar3, and Ar4 includes any one or a combination of hydrogen, an isotope of hydrogen, an aromatic group, an arylamine group, a heteroarylamine group, and a fused ring group.

In one embodiment, a molar ratio of the first material to the second material is 1:1 to 1:3.

Yet another embodiment of the present application provides a display panel including a light-emitting device layer, the light-emitting device layer includes an organic compound, and the organic compound is represented by the following general formula:

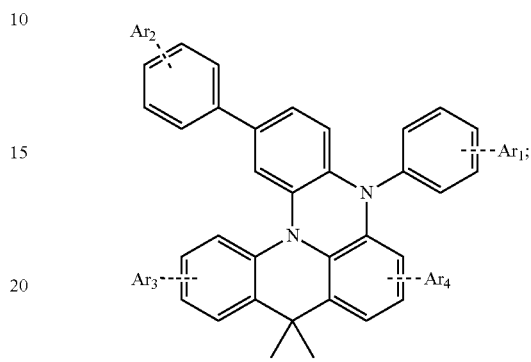

wherein any one of Ar1, Ar2, Ar3, and Ar4 includes any one or a combination of hydrogen, an isotope of hydrogen, an aromatic group, an arylamine group, a heteroarylamine group, and a fused ring group.

In one embodiment, any one of Ar1, Ar2, Ar3, and Ar4 includes any one or a combination of protium, deuterium, tritium, an aromatic group with 6 to 60 carbon atoms, an arylamine group with 6 to 60 carbon atoms, a heteroarylamine group with 6 to 60 carbon atoms, and a fused ring group with 10 to 60 carbon atoms.

In one embodiment, any one of Ar1, Ar2, Ar3, and Ar4 is an axisymmetric group containing a benzene ring.

In one embodiment, the aromatic group includes an oxygen-containing aromatic group or a silicon-containing aromatic group, the arylamine group includes an oxygen-containing arylamine group or a silicon-containing arylamine group, and the fused ring group includes any one of naphthalene, anthracene, and pyrene.

In one embodiment, any one of Ar1, Ar2, Ar3, and Ar4 is any one or a combination of the following groups:

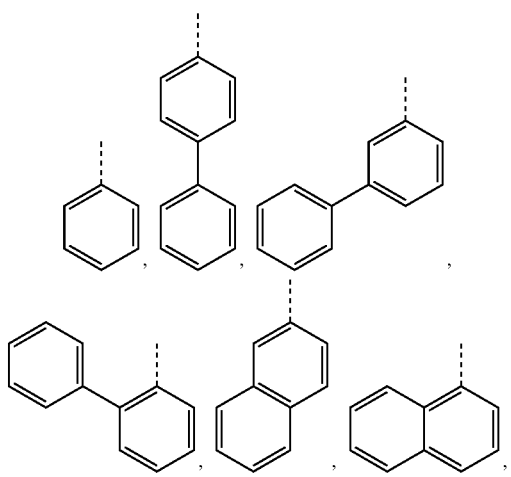

-continued
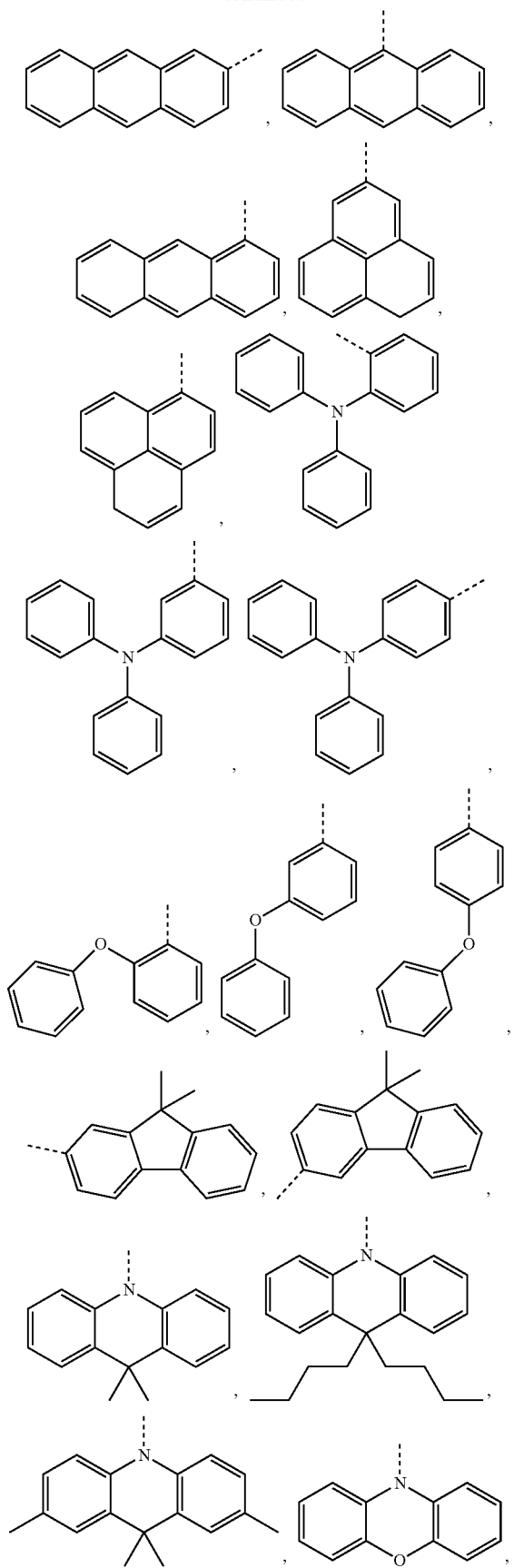
-continued
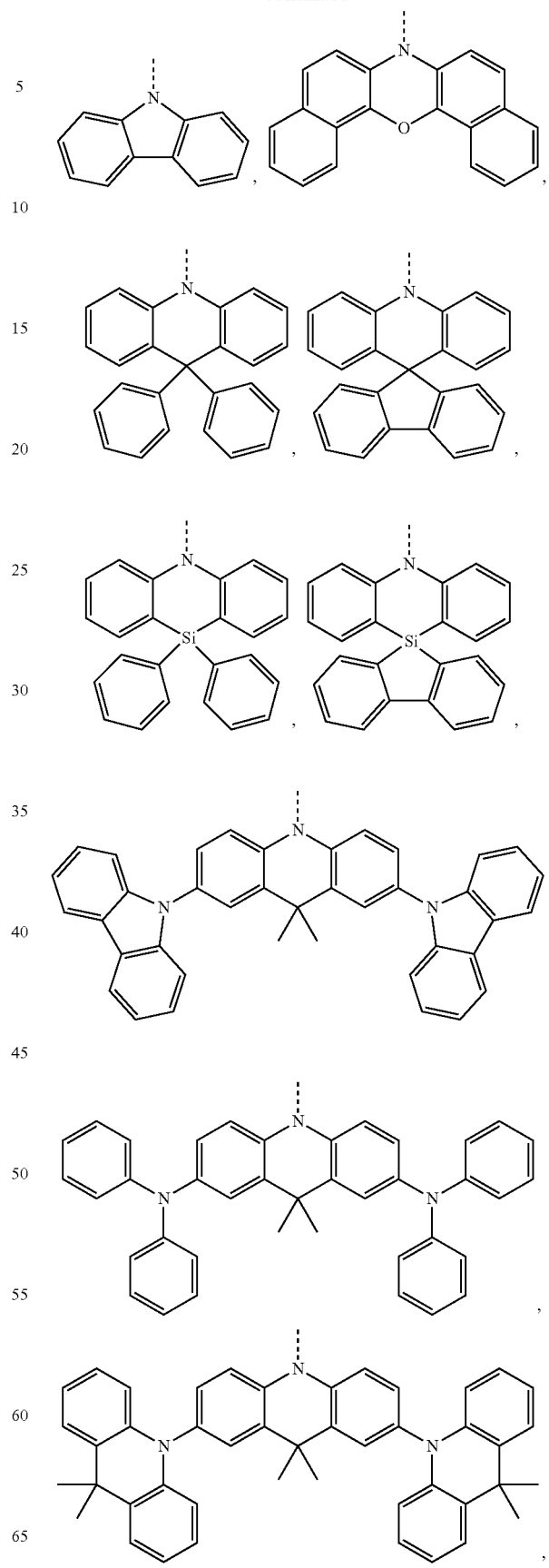

-continued
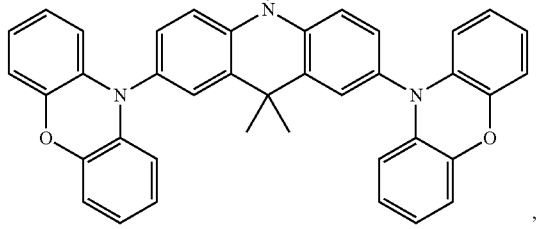
,
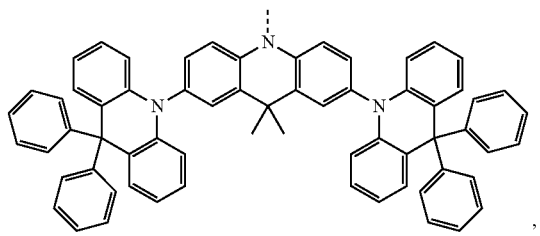
,
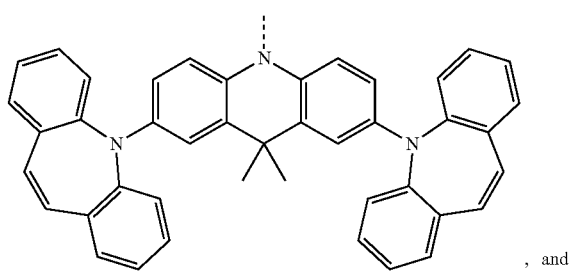
, and
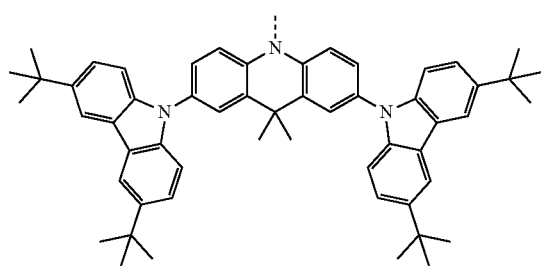
.
In one embodiment, a structural formula of the organic compound is:
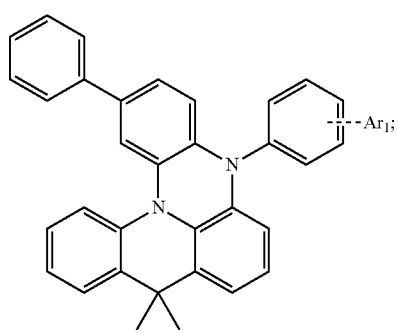
wherein Ar1 is any one of an aromatic group, an arylamine group, or a heteroarylamine group.
In one embodiment, Ar1 is any one of the following groups:
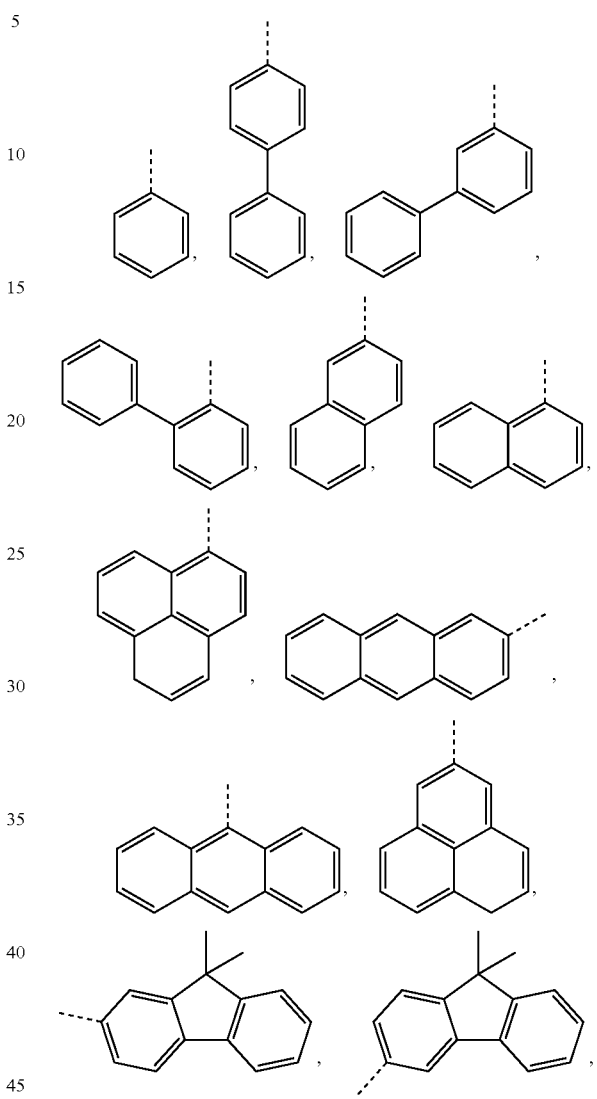
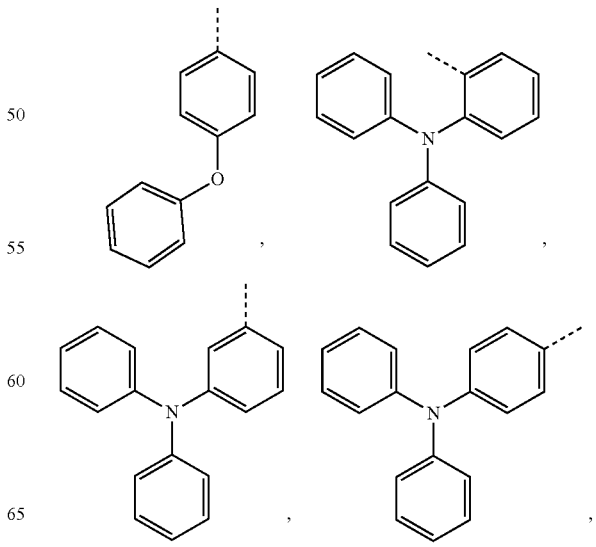

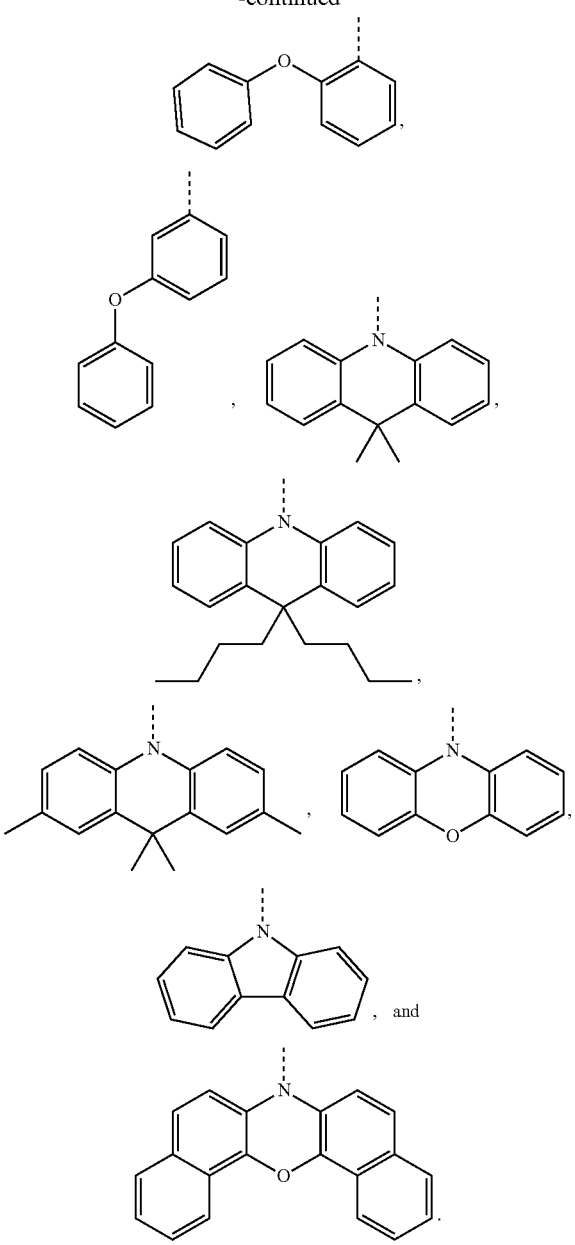
In one embodiment, a structure of the organic compound includes any one or a combination of the following:
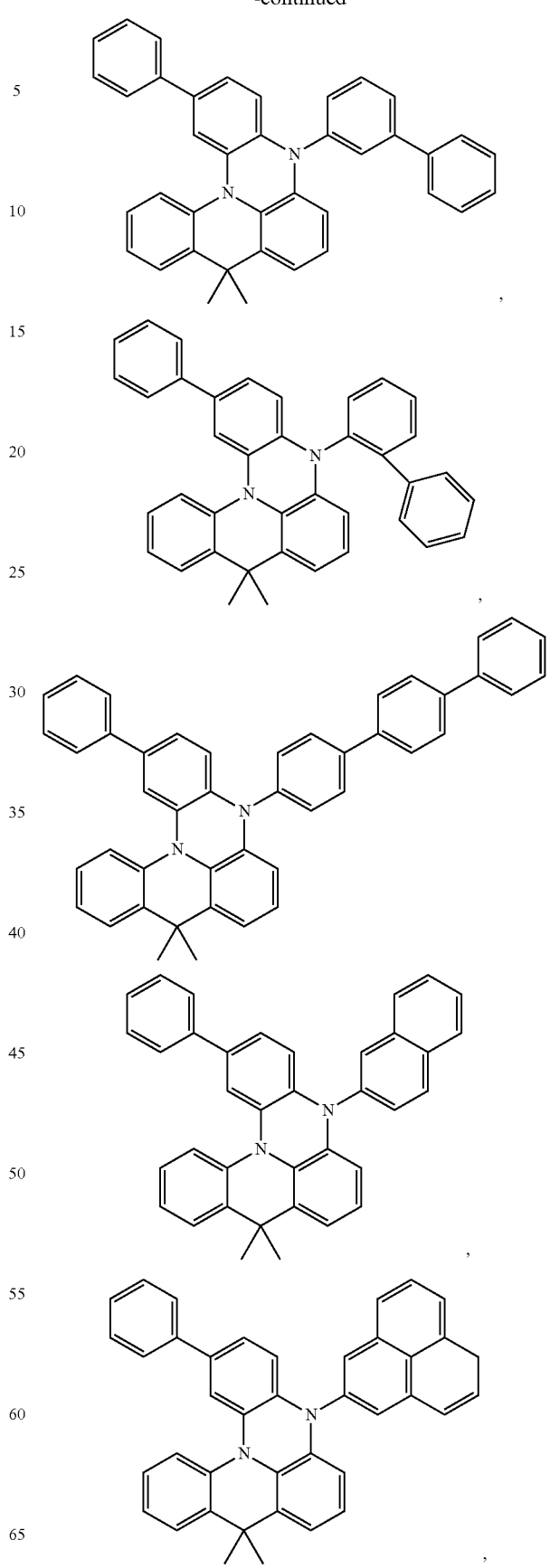

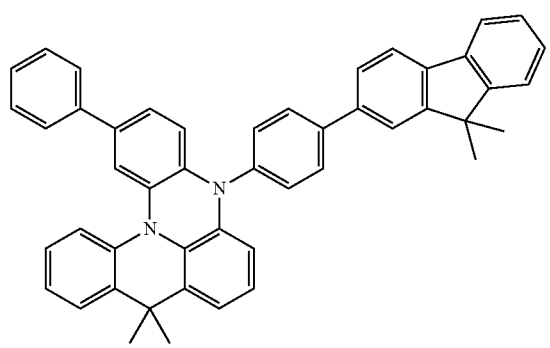
,
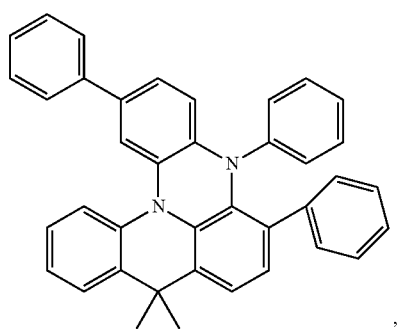
,
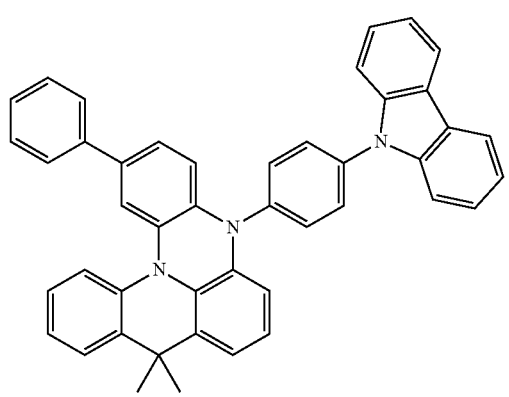
,
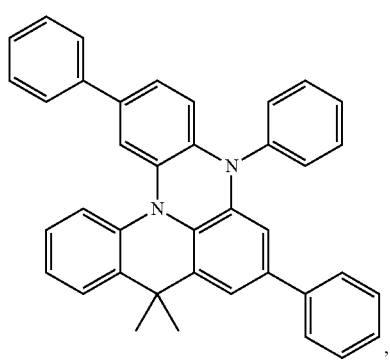
,
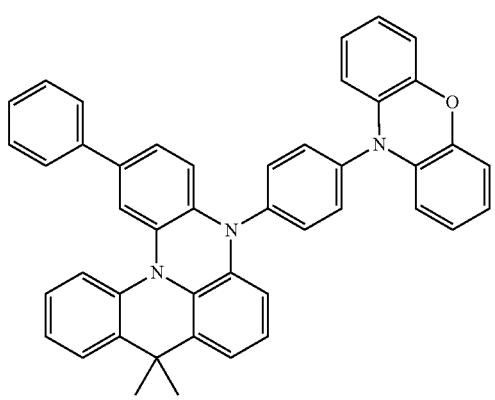
,
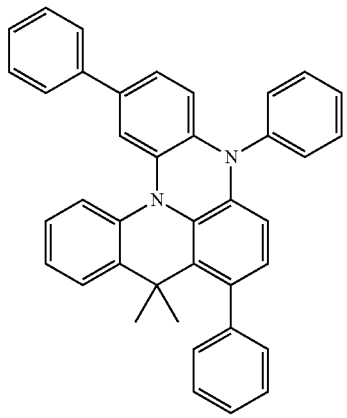
,
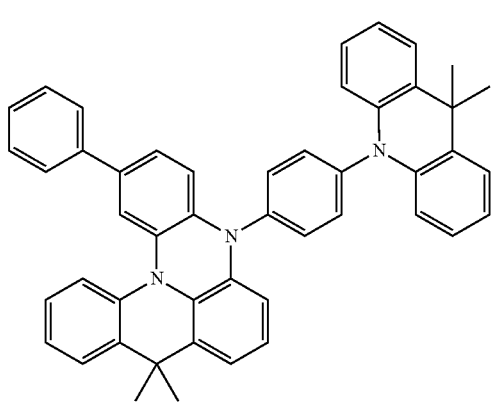
,
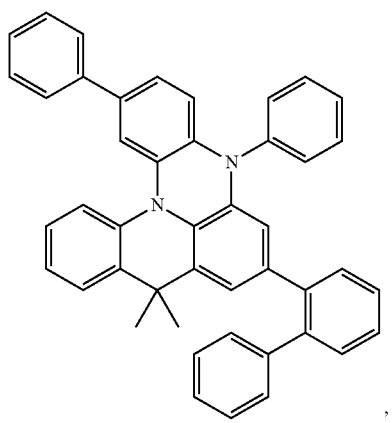
,

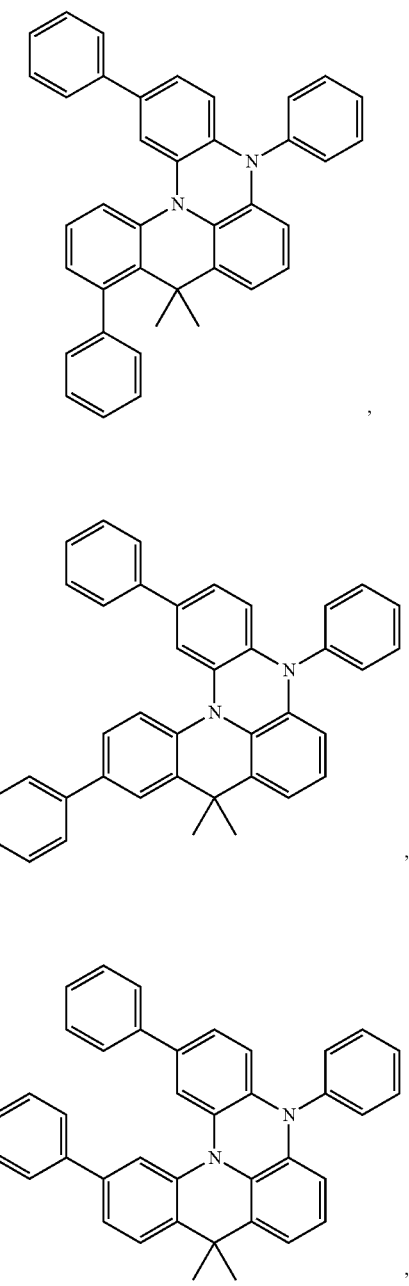

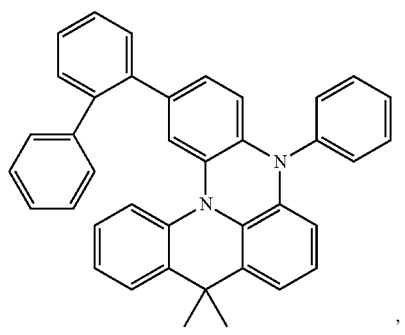

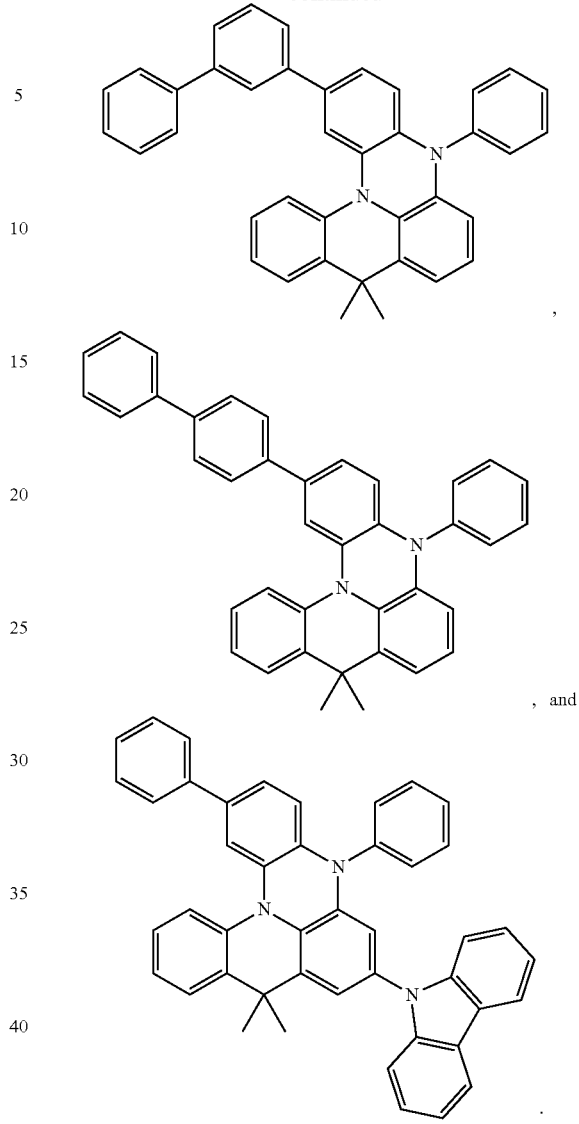

, and

In the embodiments of the present invention, by adding other electron-donating groups on the basis of a phenazine-fused acridine structure, organic compounds with high mobility are obtained, which enhance display performance of a display device.

DETAILED DESCRIPTION OF PREFERRED EMBODIMENTS

Figure 1:
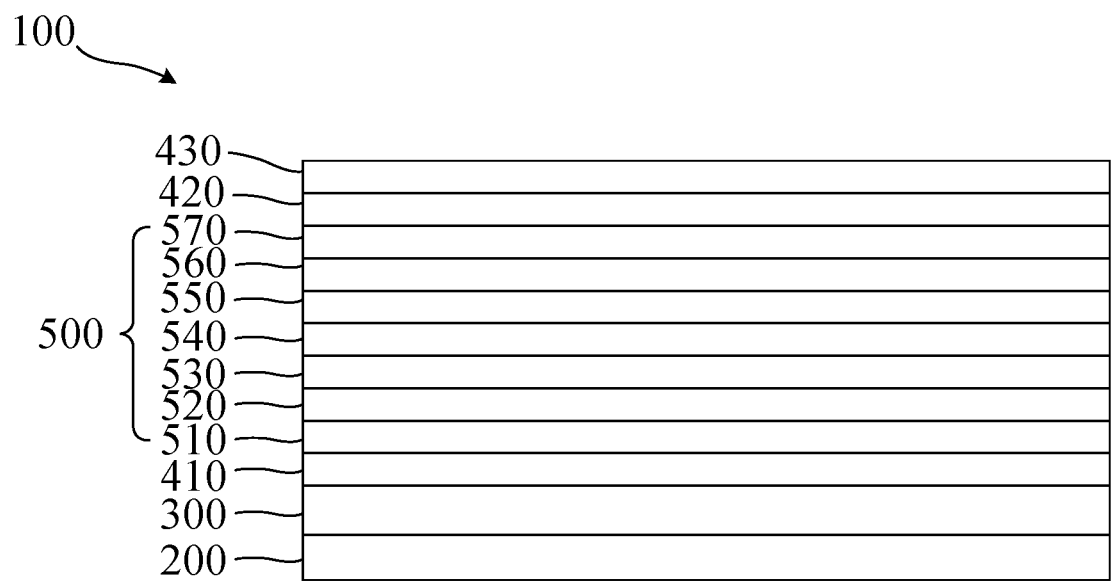
FIG. 1 is a schematic structural diagram of a display panel provided by an embodiment of the present invention.

The present application provides an organic compound, a preparation method thereof, and a display panel. In order to make the purpose, technical solution, and effect of the present application clearer and more definite, the present application is further described in detail below with reference to the accompanying drawings and examples. It should be understood that the specific embodiments described herein are only used to explain the present application, and are not used to limit the present application.

Embodiments of the present application provide an organic compound and a preparation method thereof, and a display panel, which are described in detail respectively. It should be noted that the order of description in the following embodiments is not as a limitation on the preferred order of the embodiments.

An embodiment of the present invention provides an organic compound, and the organic compound is represented by the following general formula:

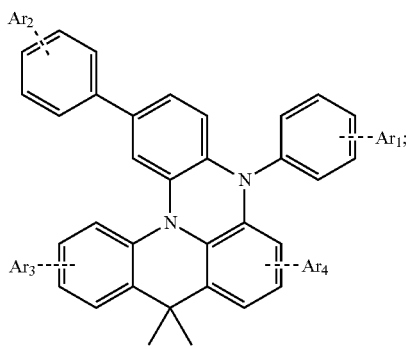

wherein any one of Ar1, Ar2, Ar3, and Ar4 includes any one or a combination of hydrogen, an isotope of hydrogen, an aromatic group, an arylamine group, a heteroarylamine group, and a fused ring group.

In the embodiments of the present invention, by adding other electron-donating groups on the basis of a phenazine-fused acridine structure, organic compounds with high mobility are obtained, which enhance display performance of a display device.

The technical solutions of the present application will now be described in conjunction with specific embodiments.

The organic compound is represented by the following general formula:

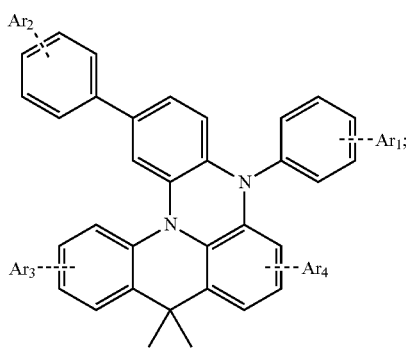

wherein a structure of the organic compound includes at least one of Ar1, Ar2, Ar3, or Ar4; and any one of Ar1, Ar2, Ar3, and Ar4 includes any one or a combination of hydrogen, an isotope of hydrogen, an aromatic group, an arylamine group, a heteroarylamine group, and a fused ring group.

In this embodiment, the general formula is the general structural formula of a phenazine-fused acridine-based structure.

In this embodiment, in the general structural formula of phenazine-fused acridine, Ar1, Ar2, Ar3, and Ar4 represent positions of substituents, and the structure of the organic compound may include at least one position substituted by a substituent of Ar1, Ar2, Ar3, or Ar4.

In this embodiment, Ar1, Ar2, Ar3, and Ar4 can all be electron-donating groups. Through the strong electron-donating ability of phenazine-fused acridine, in combination with other electron-donating groups, a compound of high mobility is obtained, the compound can be made into a transmission material for use in light-emitting materials to enhance display efficiency of the display device.

In this embodiment, any one of Ar1, Ar2, Ar3, and Ar4 includes any one or a combination of hydrogen, an isotope of hydrogen, an aromatic group, an arylamine group, a heteroarylamine group, and a fused ring group. Ar1, Ar2, Ar3 and Ar4 have an effect of adjusting a transmission efficiency.

In this embodiment, when the organic compound is substituted by only one group of Ar1, Ar2, Ar3 and Ar4, the only one group is neither hydrogen nor the hydrogen isotope.

In this embodiment, any one of Ar1, Ar2, Ar3, and Ar4 is an aromatic group or a heteroaromatic group.

In this embodiment, any one of Ar1, Ar2, Ar3, and Ar4 includes any one or a combination of protium, deuterium, tritium, an aromatic group with 6 to 60 carbon atoms, an arylamine group with 6 to 60 carbon atoms, a heteroarylamine group with 6 to 60 carbon atoms, and a fused ring group with 10 to 60 carbon atoms.

In this embodiment, any one of Ar1, Ar2, Ar3, and Ar4 is an aromatic group with 6 to 60 carbon atoms or a heteroaromatic group with 6 to 60 carbon atoms. The organic compound may be used as evaporation coating materials, C is a carbon atom, the greater the number of carbon atoms, the greater the molecular weight, the less conducive to evaporation coating, and mass production of evaporation coated molecules requires a molecular weight of the organic compound to be less than 1000.

In this embodiment, any one of Ar1, Ar2, Ar3, and Ar4 includes a nitrogen-containing aromatic group or a nitrogen-containing heteroaromatic group, wherein the nitrogen element can make the organic compound has a strong electron donating ability to improve mobility performance of the organic compound.

In this embodiment, any one of Ar1, Ar2, Ar3, and Ar4 is an axisymmetric group containing a benzene ring. The axisymmetric group containing a benzene ring can strengthen the stability of the organic compound through the axisymmetric property of the groups.

In this embodiment, the aromatic group includes an oxygen-containing aromatic group or a silicon-containing aromatic group, the arylamine group includes an oxygen-containing arylamine group or a silicon-containing arylamine group, and the fused ring group includes any one of naphthalene, anthracene, and pyrene. The incorporation of silicon or oxygen atom can increase the electron donating ability of the organic compound and improve the mobility performance of the organic compound.

In this embodiment, any one of Ar1, Ar2, Ar3, and Ar4 is any one or a combination of the following groups:
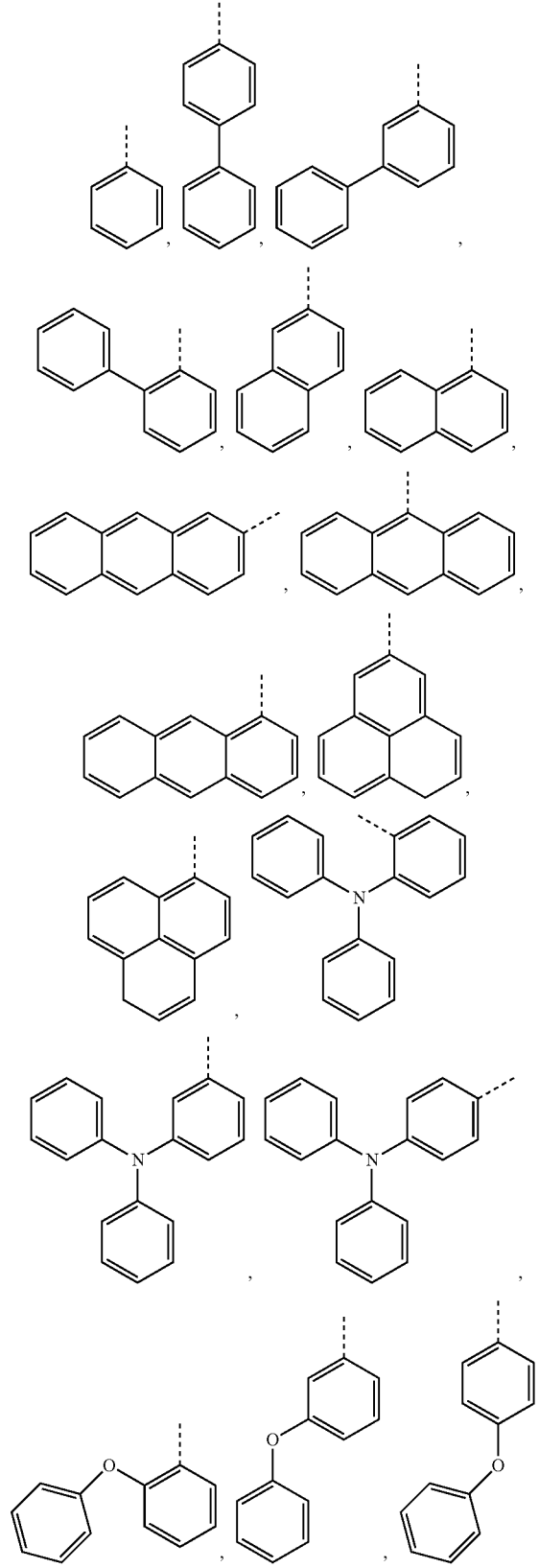
-continued
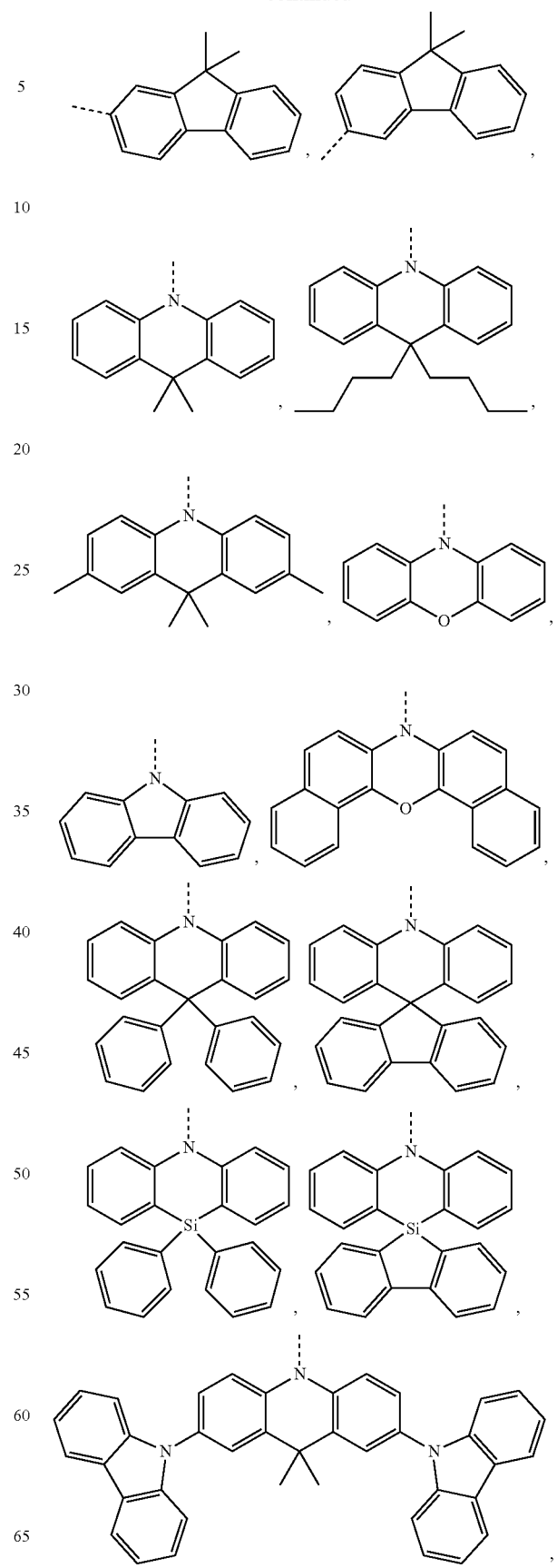

-continued

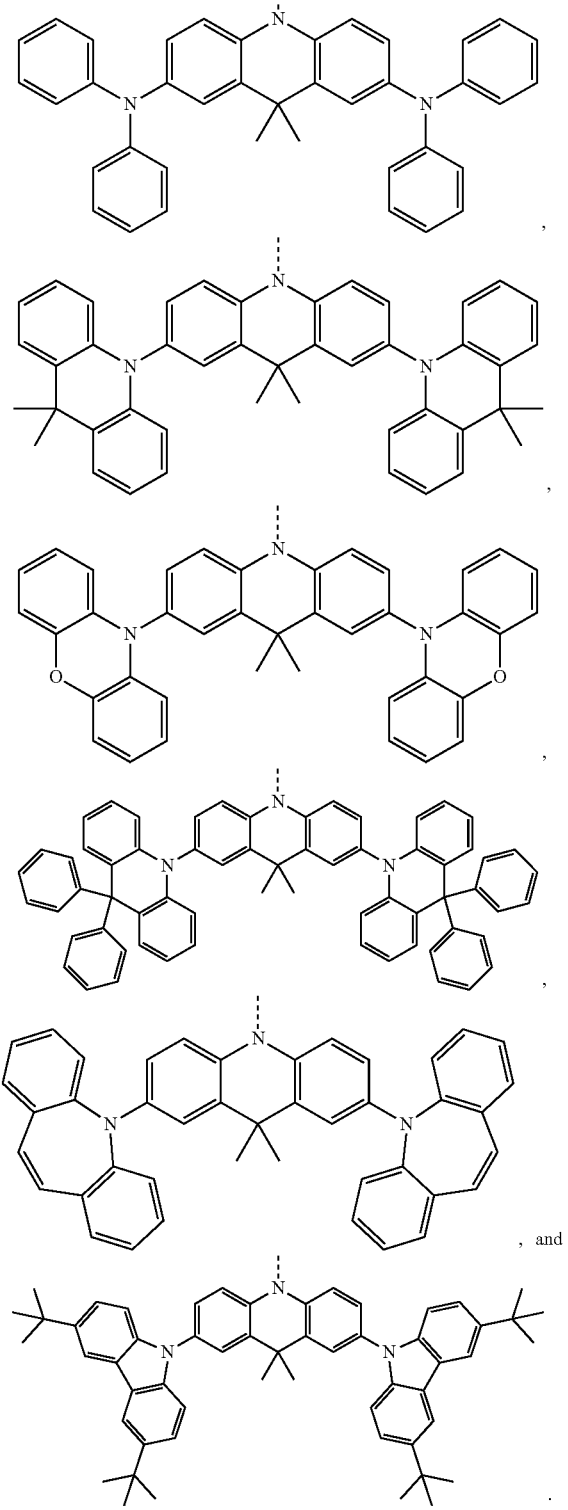

, and

In this embodiment, Ar1, Ar2, Ar3, and Ar4 adjust the mobility performance of the organic compound by their different molecular weights, improve the stability of the organic compound by the symmetric groups, and improve the mobility performance of the organic compound through the nitrogen and oxygen-containing groups, as well as effectively adjust the molecular weight of the organic compound. Meanwhile, nitrogen and oxygen can form intermolecular bonds and intramolecular bonds with hydrogen and isotopes of hydrogen to further improve the stability of the organic compound. In addition, the stability of the organic compound is improved through symmetry of silicon atoms.

In this embodiment, a structural formula of the organic compound is:

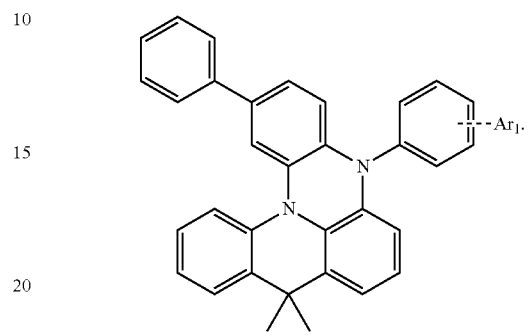

In this embodiment, Ar1 is any one of an aromatic group, an arylamine group, or a heteroarylamine group. The position of Ar1 is the last synthesized, so that it is easy to reserve a modifying group to facilitate other steps, and the main design direction for synthesis scheme is focused on Ar1 to improve the mobility performance of the organic compound.

In this embodiment, Ar1 is any one of the following groups:

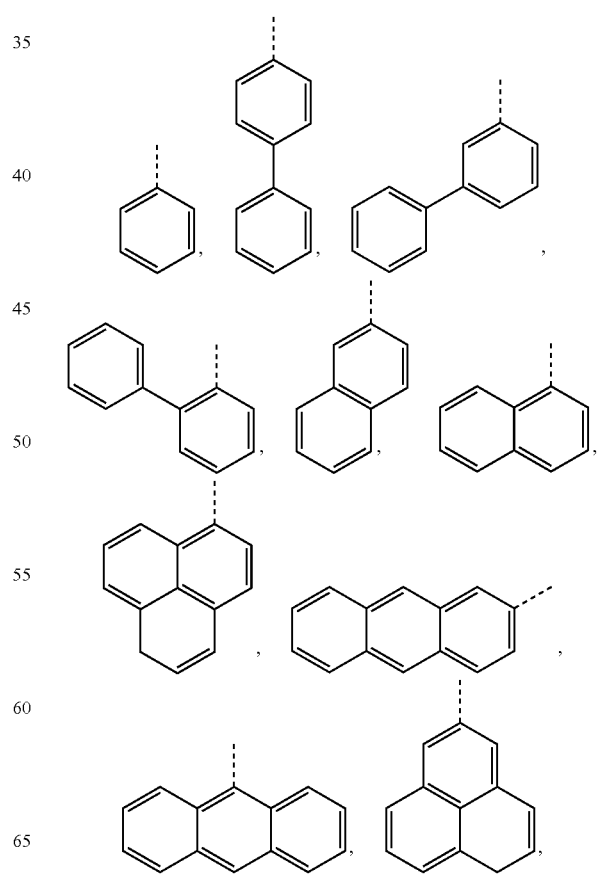

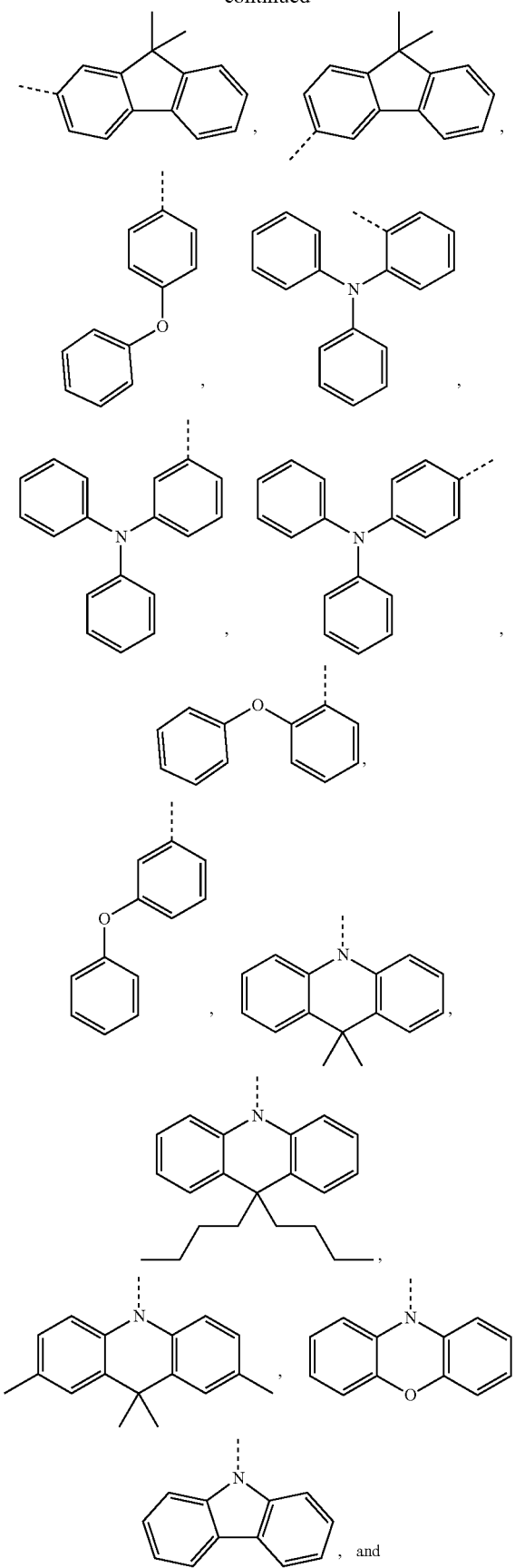

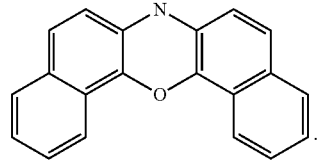

In the above-mentioned Ar1 structure, its molecular weight is relatively small and the structure is symmetrical, which can provide the organic compound with higher stability and controllable viscosity, thus preventing excessive molecular weight from impacting physical properties of the organic compound.

In this embodiment, a structure of the organic compound includes any one or a combination of the following:

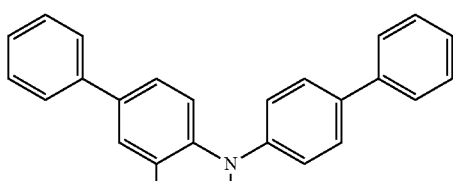

,

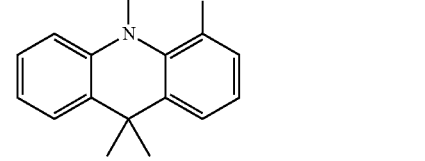

,

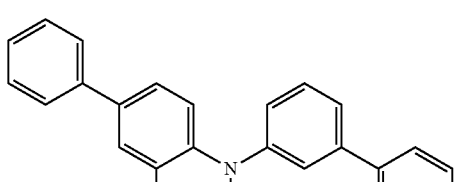

,

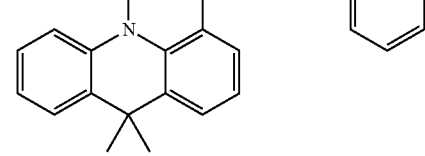

,

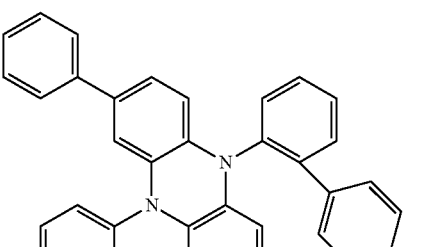

,

35
-continued
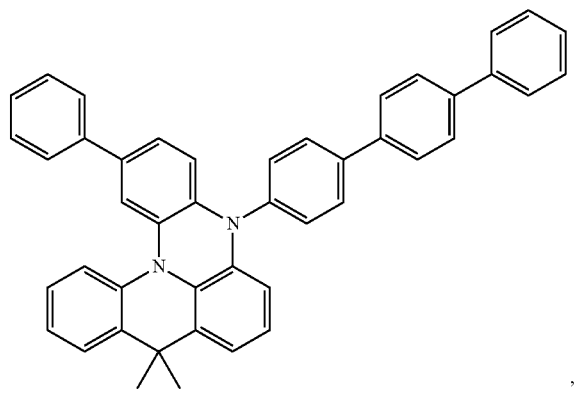
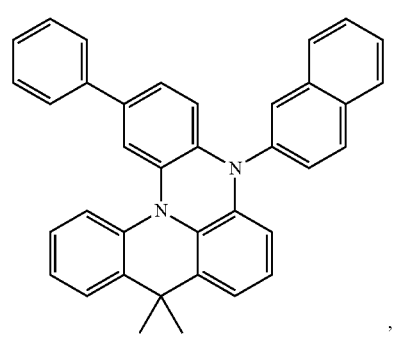
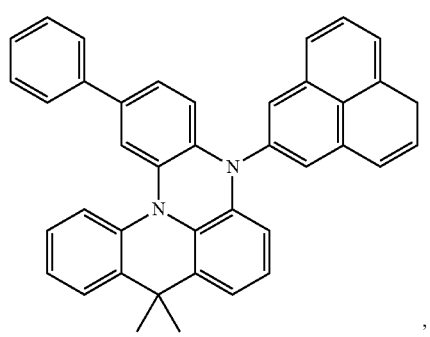
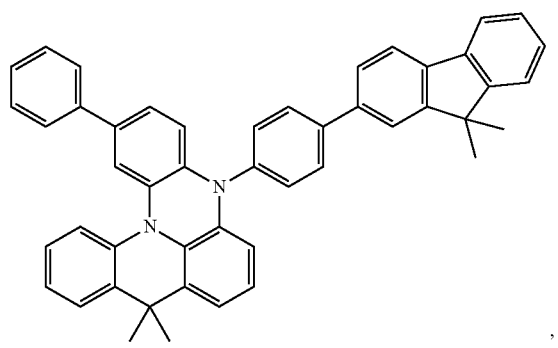
36
-continued
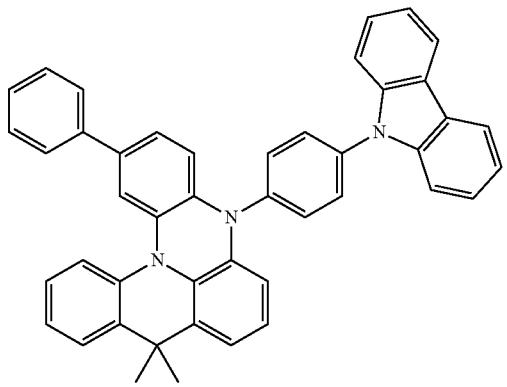
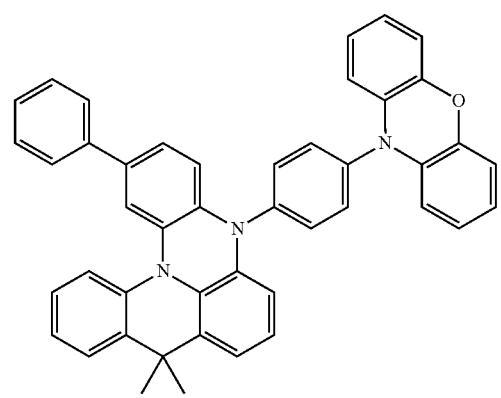
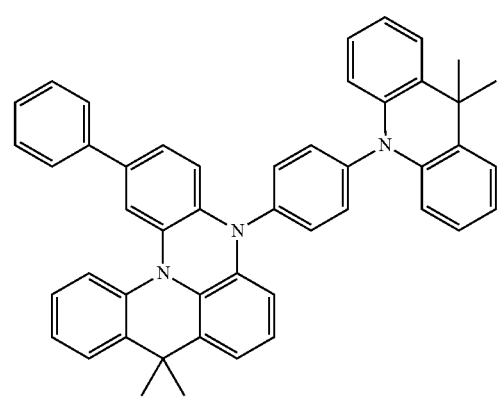
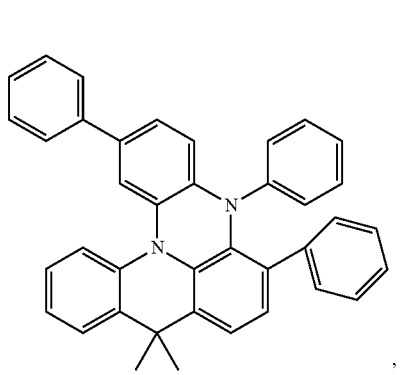

-continued
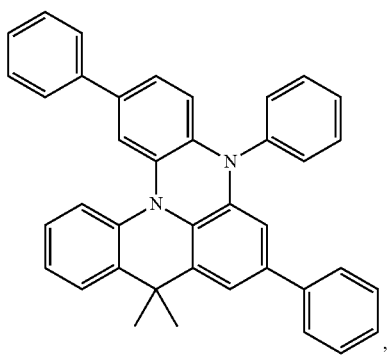
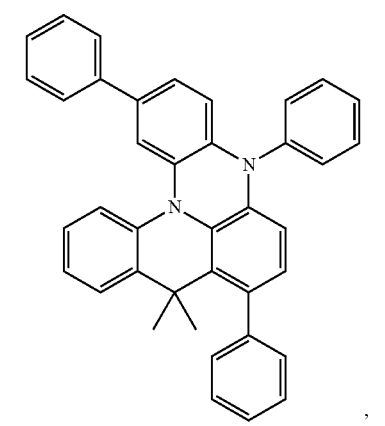
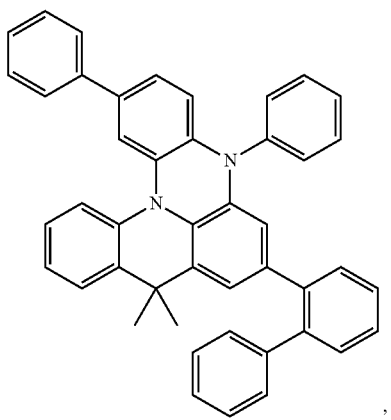
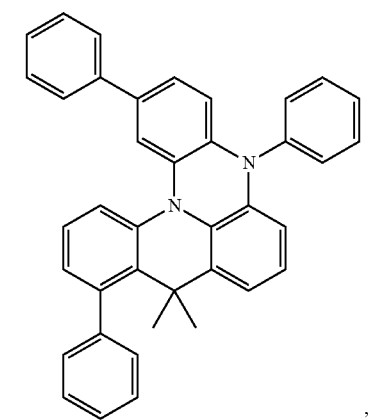
-continued
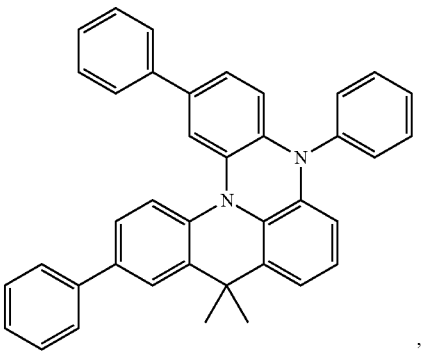
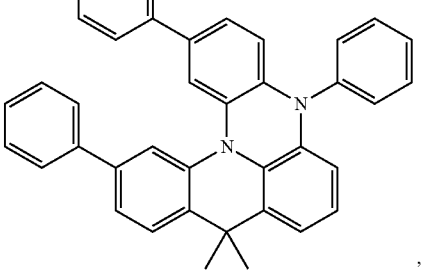
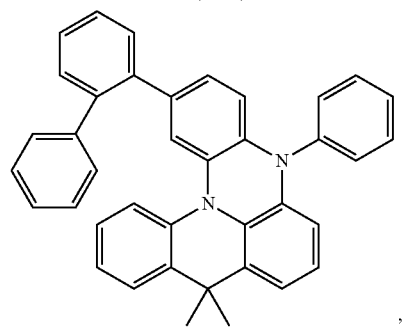
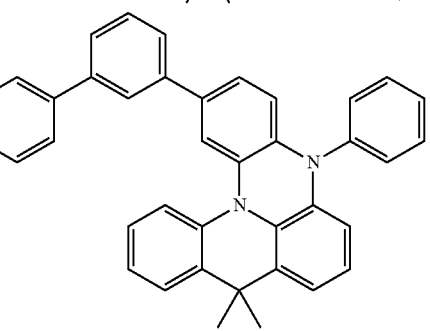
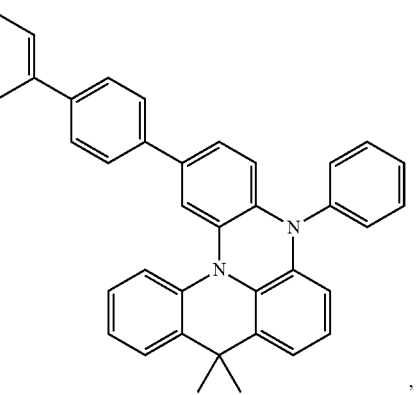
, and

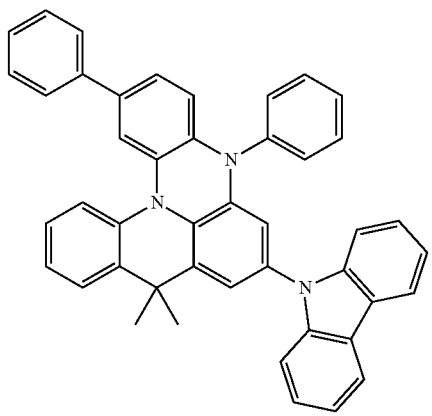

In this embodiment, the molecular bonding of the above-selected structure is relatively stable, and the material structure is relatively stable. The molecular weight is between 500 and 1000, which is suitable for vacuum evaporation, and avoids an overly high molecular weight, which causes an overly high evaporation temperature for mass production of the device.

Taking and as examples, the three compounds are named Compound 1, Compound 2, and Compound 3.

In this example, the HOMO electrochemical energy level of Compound 1 is −5.58 eV, and the LUMO electrochemical energy level is −2.53 eV. The HOMO electrochemical energy level of Compound 2 is −5.61 eV, and the LUMO electrochemical energy level is −2.54 eV. The HOMO electrochemical energy level of Compound 3 is −5.66 eV, and the LUMO electrochemical energy level is −2.53 eV. It can be seen that taking the three structures as examples, characterization parameters indicate that the organic compounds can be used as transporting materials.

In the embodiments of the present invention, by adding other electron-donating groups on the basis of a phenazine-fused acridine structure, organic compounds with high mobility are obtained, which enhance display performance of a display device.

An embodiment of the present invention also provides a method of preparing an organic compound, including:

S100, mixing the first material and the second material to form the organic compound, and the organic compound is represented by the general formula (1):

the first material is represented by the general formula (2):

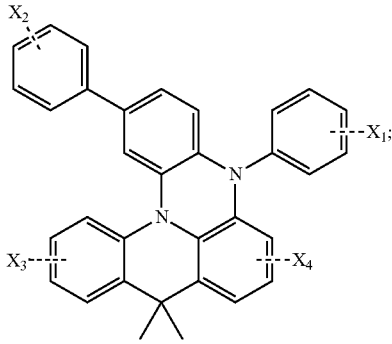

wherein the second material includes any one or a combination of an aromatic group, an arylamine group, a heteroarylamine group, and a fused ring group; each of X1, X2, X3, and X4 is halogen; a structure of the first material includes at least one of X1, X2, X3, and X4; and any one of Ar1, Ar2, Ar3, and Ar4 includes any one or a combination of hydrogen, an isotope of hydrogen, an aromatic group, an arylamine group, a heteroarylamine group, and a fused ring group.

In the embodiments of the present invention, by adding other electron-donating groups on the basis of a phenazine-fused acridine structure, organic compounds with high mobility are obtained, which enhance display performance of a display device.

The technical solutions of the present invention will now be described in conjunction with specific embodiments.

The method of preparing the organic compound includes:

S100, mixing a first material and a second material to form the organic compound, and the organic compound is represented by the general formula (1):

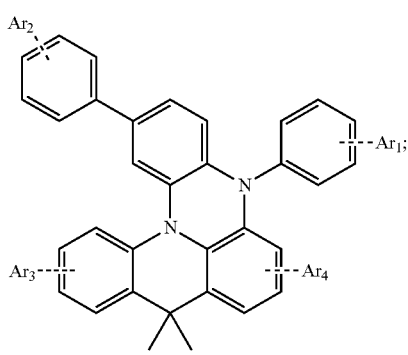

the first material is represented by the general formula (2):

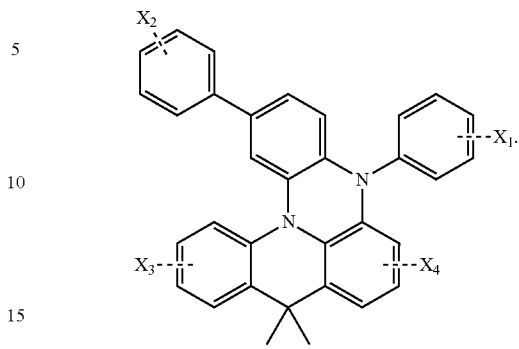

In this embodiment, any one of Ar1, Ar2, Ar3, and Ar4 includes any one or a combination of hydrogen, an isotope of hydrogen, an aromatic group, an arylamine group, a heteroarylamine group, and a fused ring group. Ar1, Ar2, Ar3 and Ar4 have an effect of adjusting a transmission efficiency.

In this embodiment, in the general structural formula of phenazine acridine, Ar1, Ar2, Ar3, and Ar4 represent positions of substituents, and the structure of the organic compound may include at least one position substituted by a substitution of Ar1, Ar2, Ar3, or Ar4.

In this embodiment, X1, X2, X3, and X4 are all halogens, and represent positions of the substituents, and a structure of the first material may include at least one position substituted by a substitution of X1, X2, X3, and X4.

In this embodiment, X1, X2, X3, and X4 are all halogens, and the structure of the first material includes at least one of X1, X2, X3, and X4. The second material includes any one or a combination of an aromatic group, an arylamine group, a heteroarylamine group, and a fused ring group. Any one of Ar1, Ar2, Ar3, and Ar4 includes any one or a combination of an aromatic group, an arylamine group, a heteroarylamine group, and a fused ring group.

In this embodiment, X1, X2, X3 and X4 are all halogens. In terms of synthesis efficiency, the synthesis efficiency of bromine and iodine is higher; and in terms of cost calculation, the cost of chlorine is lower.

In this embodiment, any one of Ar1, Ar2, Ar3 and Ar4 is an aromatic group or a heteroaromatic group.

In this embodiment, any one of Ar1, Ar2, Ar3, and Ar4 includes any one or a combination of protium, deuterium, tritium, an aromatic group with 6 to 60 carbon atoms, an arylamine group with 6 to 60 carbon atoms, a heteroarylamine group with 6 to 60 carbon atoms, and a fused ring group with 10 to 60 carbon atoms.

In this embodiment, any one of Ar1, Ar2, Ar3, and Ar4 is an aromatic group with 6 to 60 carbon atoms or a heteroaromatic group with 6 to 60 carbon atoms. The organic compound may be used as evaporation coating materials, C is a carbon atom, the greater the number of carbon atoms, the greater the molecular weight, the less conducive to evaporation coating, and mass production of evaporation coated molecules requires a molecular weight of the organic compound to be less than 1000.

In this embodiment, any one of Ar1, Ar2, Ar3, and Ar4 includes a nitrogen-containing aromatic group or a nitrogen-containing heteroaromatic group, wherein the nitrogen element can make the organic compound has a strong electron donating ability to improve mobility performance of the organic compound.

In this embodiment, any one of Ar1, Ar2, Ar3, and Ar4 is an axisymmetric group containing a benzene ring. The axisymmetric group containing a benzene ring can strengthen the stability of the organic compound through the axisymmetric property of the groups.

In this embodiment, the aromatic group includes an oxygen-containing aromatic group or a silicon-containing aromatic group, the arylamine group includes an oxygen-containing arylamine group or a silicon-containing arylamine group, and the fused ring group includes any one of naphthalene, anthracene, and pyrene. The incorporation of silicon or oxygen atom can increase the electron donating ability of the organic compound and improve the mobility performance of the organic compound.

In this embodiment, any one of Ar1, Ar2, Ar3, and Ar4 is any one or a combination of the following groups:

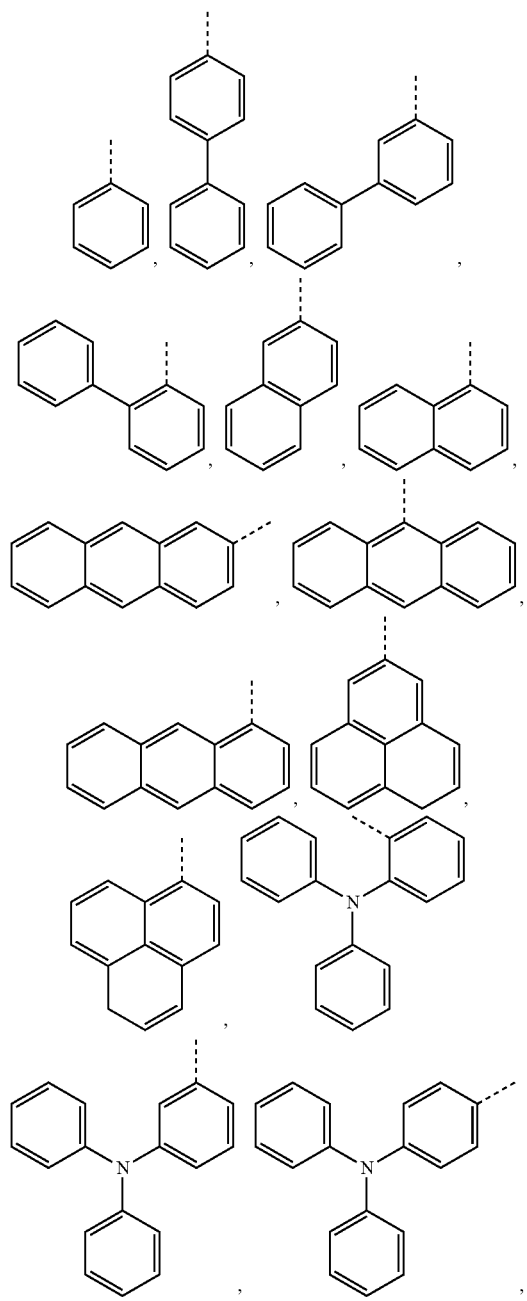

-continued

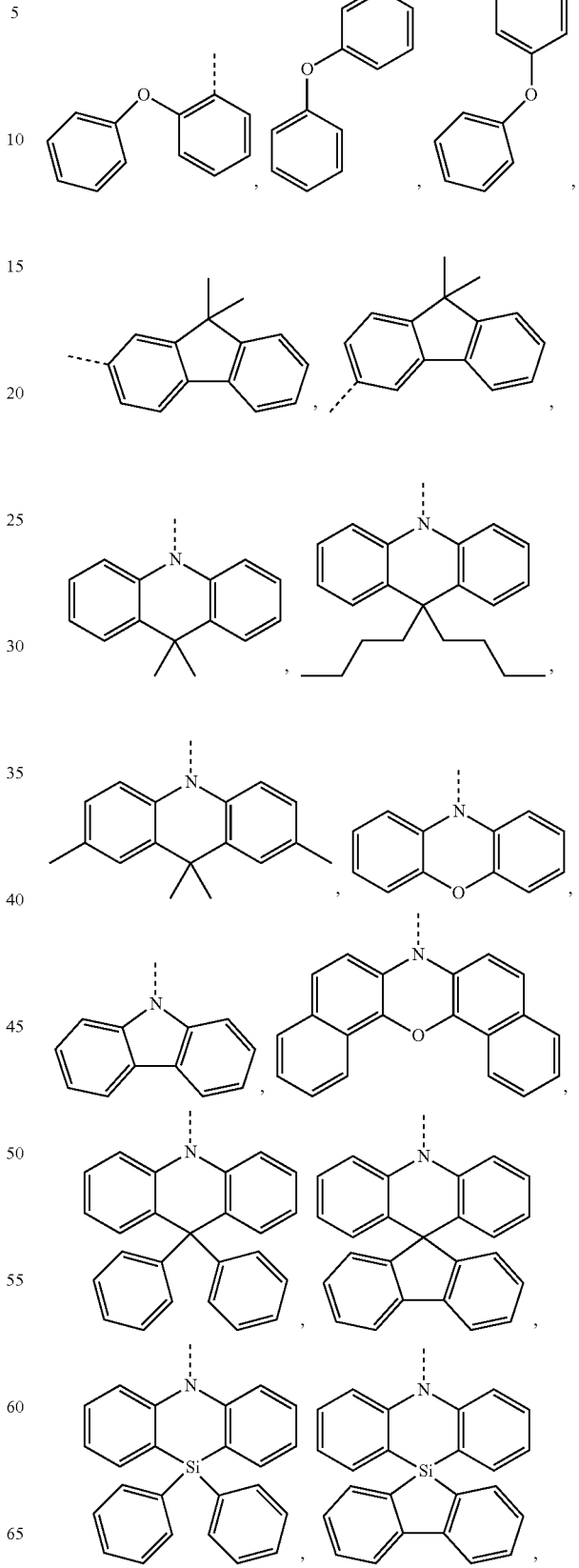

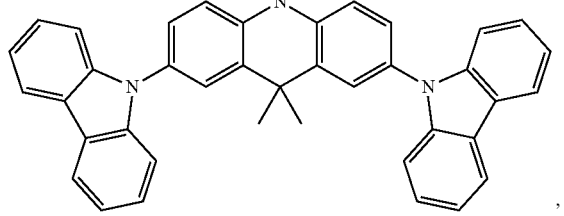

,

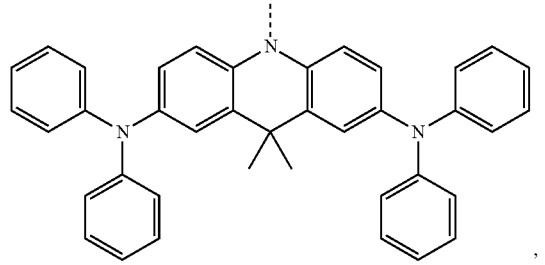

,

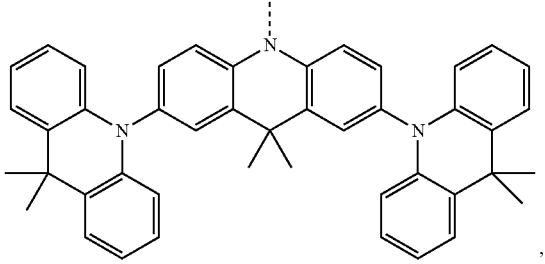

,

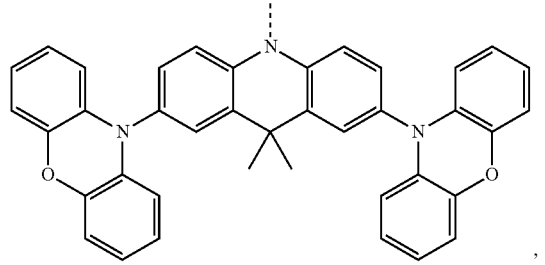

,

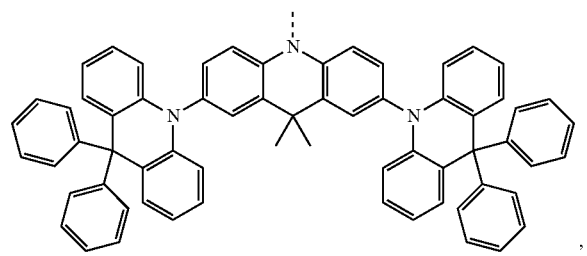

,

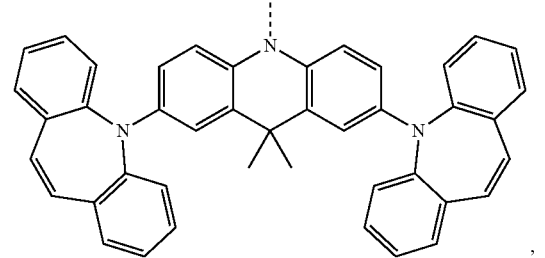

,

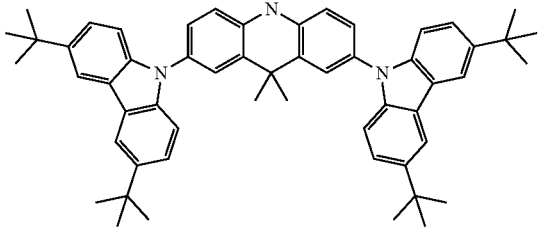

and

In this embodiment, Ar1, Ar2, Ar3, and Ar4 adjust the mobility performance of the organic compound by their different molecular weights, improve the stability of the organic compound by the symmetric groups, and improve the mobility performance of the organic compound through the nitrogen and oxygen-containing groups, as well as effectively adjust the molecular weight of the organic compound. Meanwhile, nitrogen and oxygen can form intermolecular bonds and intramolecular bonds with hydrogen and isotopes of hydrogen to further improve the stability of the organic compound. In addition, the stability of the organic compound is improved through symmetry of silicon atoms.

In this embodiment, a structural formula of the organic compound is:

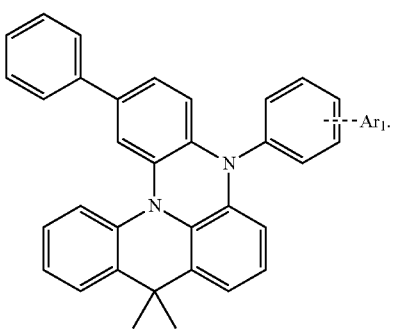

In this embodiment, Ar1 is any one of an aromatic group, an arylamine group, or a heteroarylamine group. A position of Ar1 is the last synthesized, so that it is easy to reserve a modification group to facilitate other steps, and the main design direction for synthesis scheme is focused on Ar1 to improve the mobility performance of the organic compound.

In this embodiment, a structural formula of the first material is:

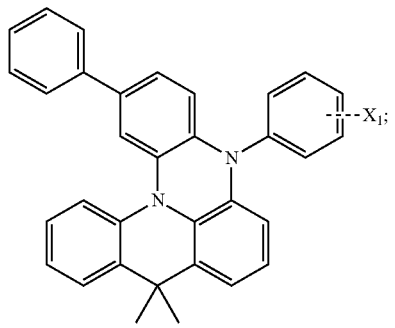

the second material includes any one of the following groups:
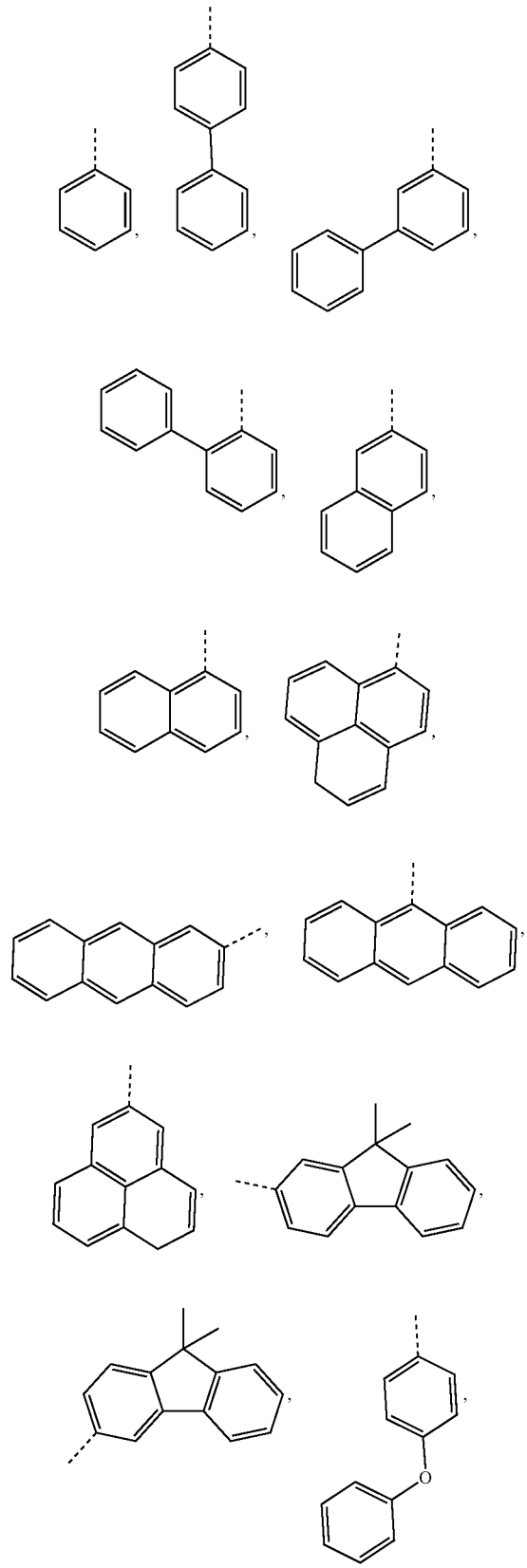
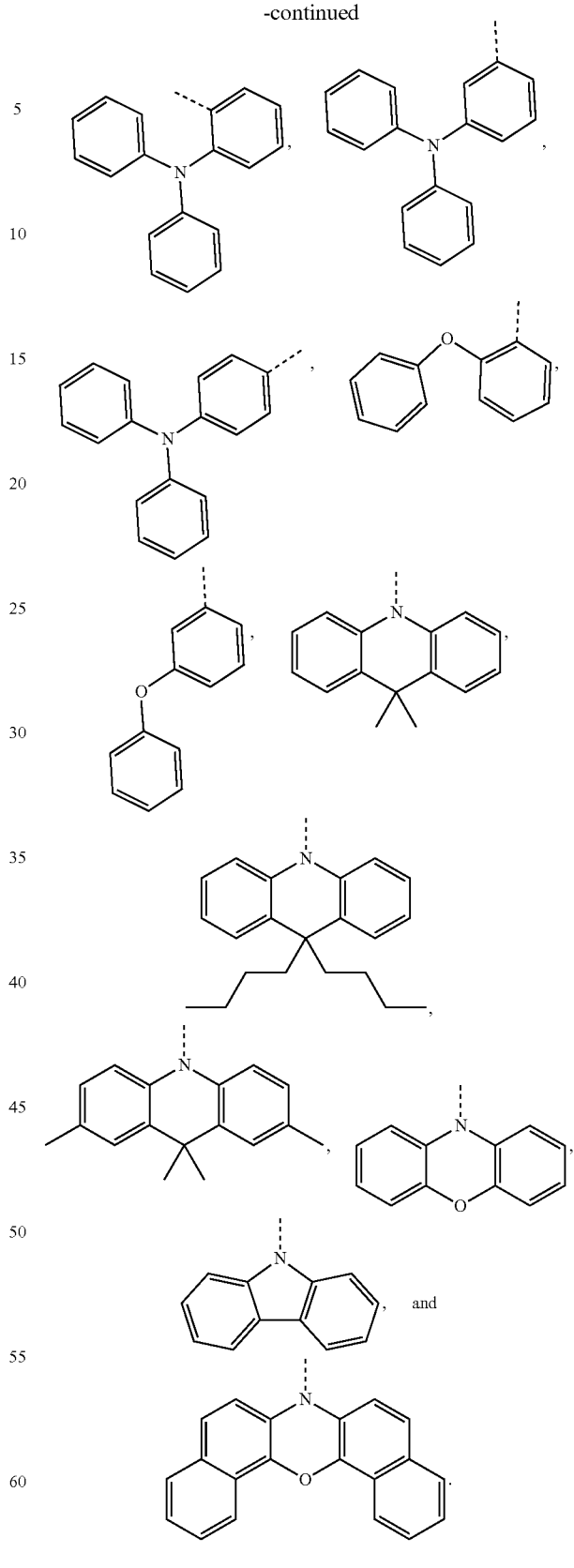
In the above-mentioned Ar1 structure, its molecular weight is relatively small and the structure is symmetrical, which can provide the organic compound with higher stability and controllable viscosity, thus preventing excessive molecular weight which impacting physical properties of the organic compound.

In this embodiment, Ar1, Ar2, Ar3, and Ar4 are all electron-donating groups. Through the strong electron-donating ability of phenazine acridine, in combination with other electron-donating groups, a compound of high mobility is obtained, the compound can be made into a transmission material for use in light-emitting materials to enhance display efficiency of the display device.

In this embodiment, the step S100 is in an inert gas environment for reaction, and the inert gas environment can be argon, or helium, which can protect the stability of the organic compound and ensure the efficiency of synthesis.

In this embodiment, the step S100 includes the following steps:

S110, mixing the first material and the second material in a molar ratio of 1:1 to 1:1.3 to form a first mixture.

In this embodiment, the step S110 is to mix the first material and the second material in a molar ratio of 1:1.2 to form a first mixture. Appropriately increasing the ratio of the second material can increase utilization rate of the first material. When the first material and the second material are mixed in a molar ratio of 1:1.2, they can be fully reacted, and it can also avoid the waste of the second substance or the excessive impurities in the product causing product purity not up to standard.

S120, adding a catalyst to the first mixture.

In this embodiment, the catalyst can speed up the progress of the step S100 to improve the production efficiency of the organic compound.

In this embodiment, the catalyst may be palladium acetate. Palladium acetate can speed up the reaction without undermining the performance of the organic compound. It is also easier to separate the palladium acetate in the later stage, which is convenient and quick, and accelerates the production efficiency of the reaction.

In this embodiment, a ratio of an amount of the catalyst material to the amount of the first material is 1:20 to 1:30.

In this embodiment, the ratio of the amount of the material of the catalyst to the amount of the material of the first material is 1:25. This content can not only ensure the catalytic efficiency, but also facilitate the separation and improve the production efficiency during the later purification and separation of the catalyst.

S130, adding a ligand to the first mixture.

In this embodiment, the ligand can be used to protect other functional groups or stabilize some easily reactive compounds, such as any one or more of aromatic groups, arylamine groups, heteroarylamine groups and fused ring groups of the second material, and the nitrogen heterocyclic ring in the first material.

In this embodiment, the ligand can be tri-tert-butyl phosphine tetrafluoroborate. Using tri-tert-butyl phosphine tetrafluoroborate as the ligand, the reaction conditions do not require an addition of expensive silver salt, which can save process steps to speed up the synthesis of complex polyaromatic ring compounds, make the reaction more green and environmentally friendly and have high atom utilization, and realize the currently advocated concept of green chemistry, and is also helpful for functional group compatibility and reaction efficiency.

In this embodiment, the ratio of the amount of the ligand material to the amount of the second material is 1:8 to 1:12.

In this embodiment, the ratio of the amount of the ligand material to the amount of the second material is 1:10. This content can not only ensure that the group protecting the second material will not be damaged, but also can prevent the excessive content of the ligand from inhibiting the progress of the reaction, thus ensuring the efficiency of reaction production.

S140, adding alkali to the first mixture.

In this embodiment, the alkali is used to provide an alkaline environment.

The alkali may be NaOt-Bu. NaOt-Bu not only provides an alkaline environment, but also has a certain catalytic effect to speed up the production efficiency of the organic compound.

In this embodiment, a ratio of an amount of the alkali material to an amount of the second material is 1:0.8 to 1:1.2.

In this embodiment, the ratio of the amount of the alkali material to the amount of the second material is 1:1. This content can not only ensure existence of an alkaline environment, but also increase a certain reaction rate and ensure the efficiency of the production reaction, and at the same time will not make the organic compound too viscous due to excessively high pH, which is inconvenient for subsequent steps.

S150, adding dehydrated and deoxygenated toluene to the first mixture.

In this embodiment, the step S110 to the step S150 can be performed simultaneously.

In this embodiment, after the step S110 to the step S150, a second mixture is formed.

S160, the second mixture is reacted at 120° C. for 24 hours to form a third mixture.

S170, cooling the third mixture to room temperature.

S180, extracting the third mixture in ice water and combining its organic phases to form a fourth mixture.

In this embodiment, an extractant used in the step S180 may be dichloromethane.

S190, the fourth mixture is subjected to rotary evaporation, column chromatography separation and purification to prepare the organic compound.

In this embodiment, the column chromatography agent for column chromatography can be dichloromethane:n-hexane in a volume ratio of 1:1 to 1:10.

In this embodiment, the column chromatography agent for column chromatography can be dichloromethane:n-hexane in a volume ratio of 1:5. It can achieve good separation effects without excessive waste and save production costs.

In this embodiment, a structure of the organic compound includes any one or a combination of the following:

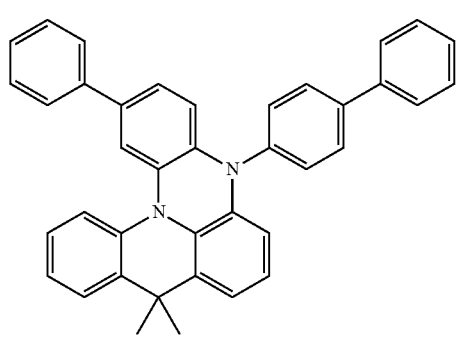

,

51
-continued
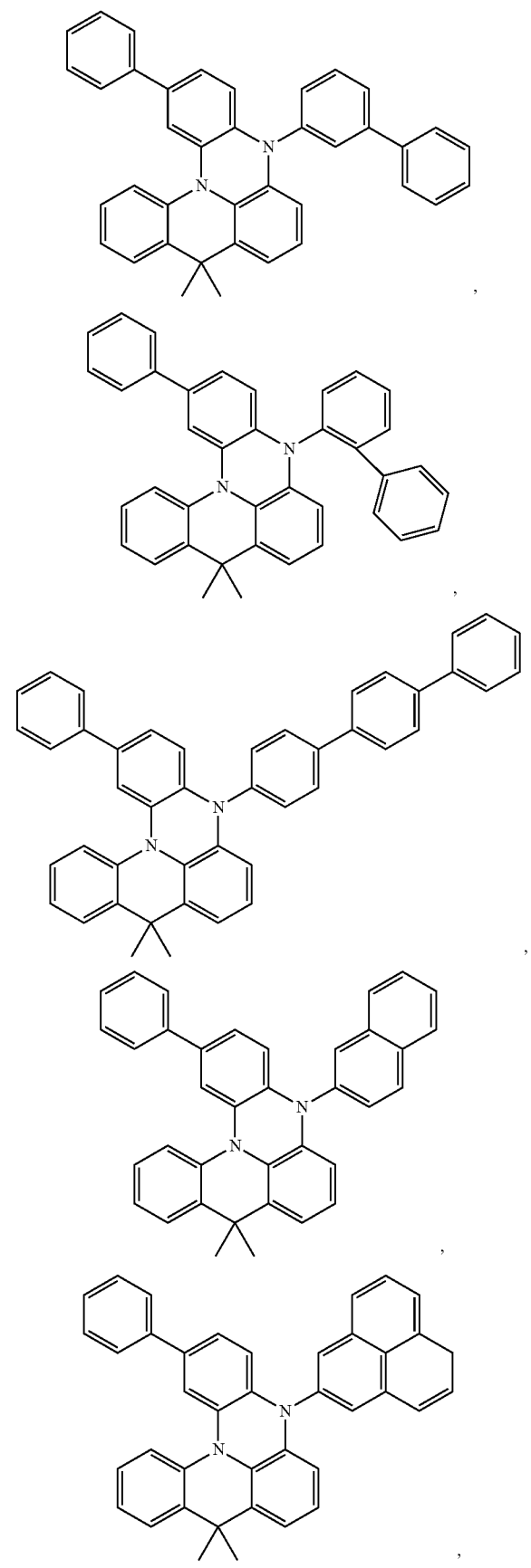
52
-continued
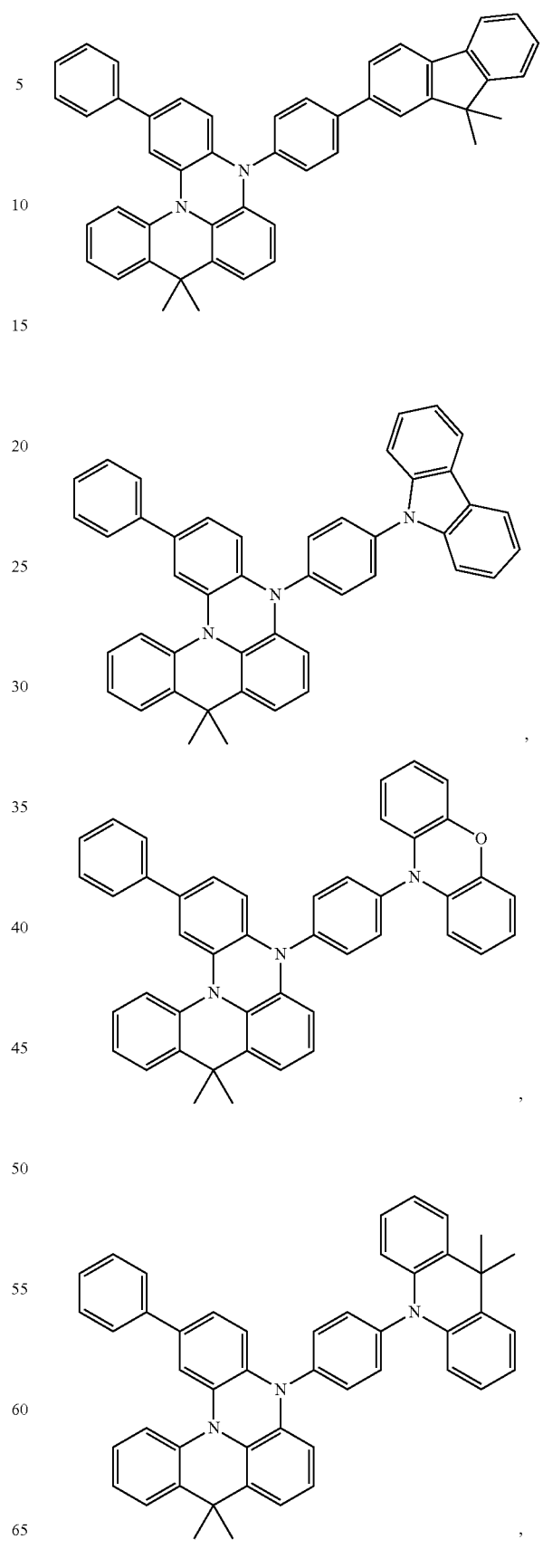

53
-continued
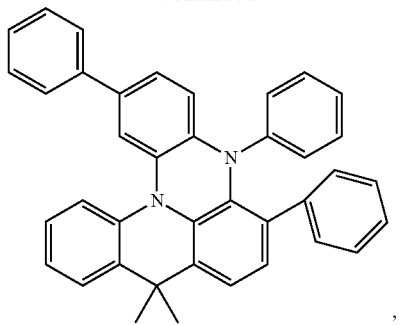
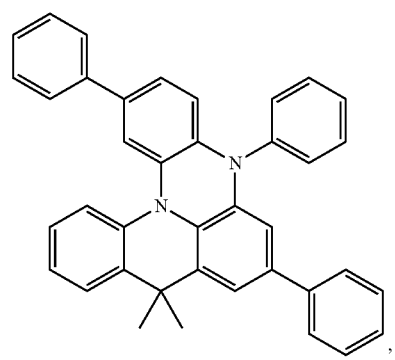
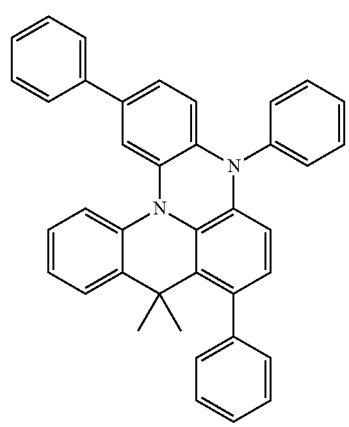
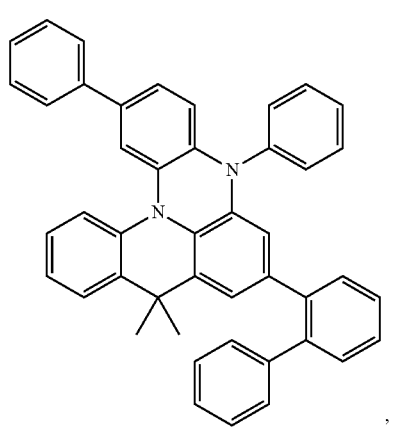
54
-continued
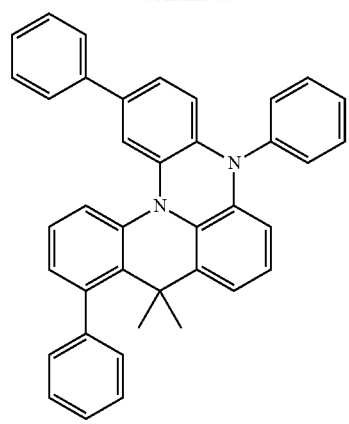
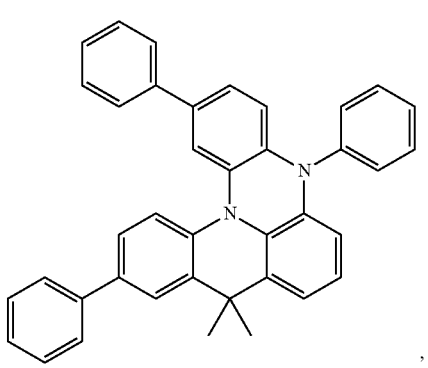
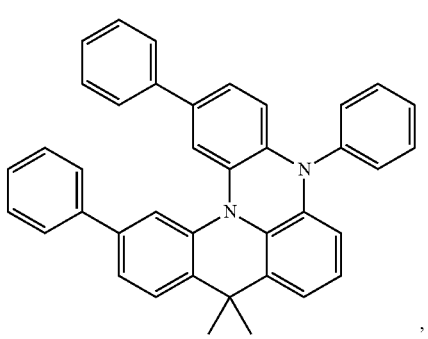
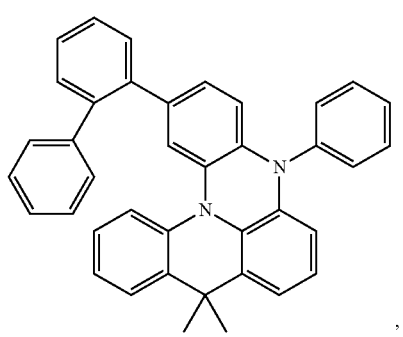

-continued

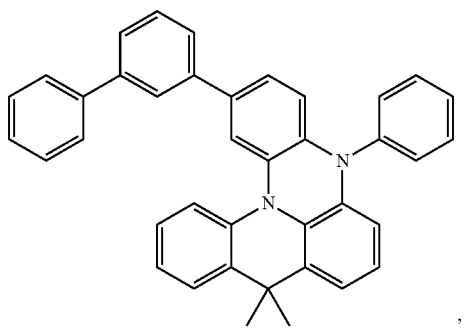
,

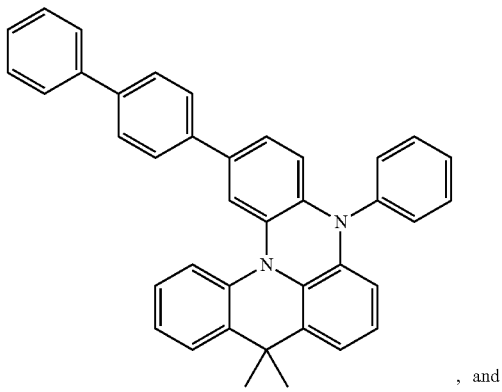
, and

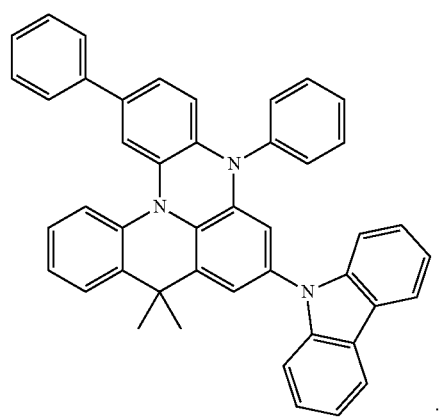

In this embodiment, the molecular bonding of the above-selected structure is relatively stable, and the material structure is relatively stable. The molecular weight is between 500 and 1000, which is suitable for vacuum evaporation, and avoids an overly high molecular weight, which causes an overly high evaporation temperature for mass production of the device.

Taking

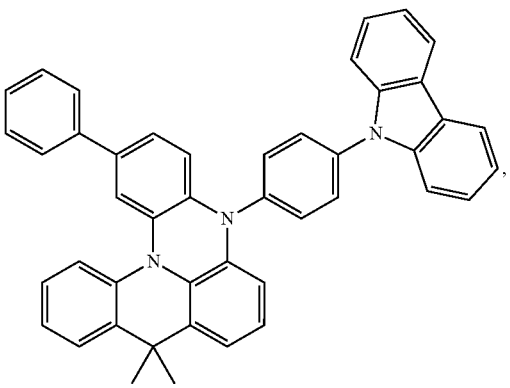
,

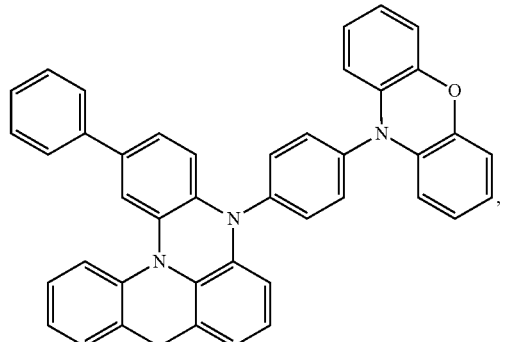
, and

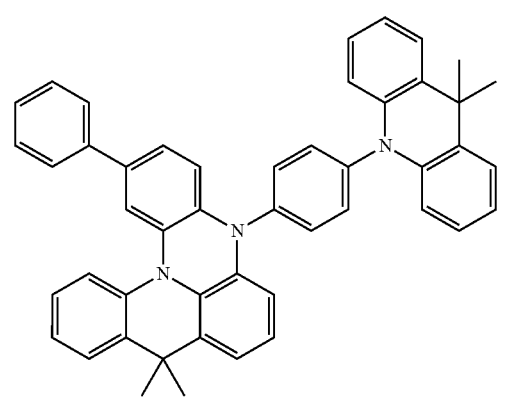 [SMILES: CC1(C)c2ccccc2N(c2ccc(N3c4ccc(-c5ccccc5)cc4N4c5ccccc5C(C)(C)c5cccc3c54)cc2)c2ccccc21]

as examples, the three compounds are named Compound 1, Compound 2, and Compound 3.

In this example, the HOMO electrochemical energy level of Compound 1 is −5.58 eV, and the LUMO electrochemical energy level is −2.53 eV. The HOMO electrochemical energy level of Compound 2 is −5.61 eV, and the LUMO electrochemical energy level is −2.54 eV. The HOMO electrochemical energy level of Compound 3 is −5.66 eV, and the LUMO electrochemical energy level is −2.53 eV. It can be seen that taking the three structures as examples, characterization parameters indicate that the organic compounds can be used as transporting materials.

In this embodiment, the reaction formula of Compound 1 is as follows:

In this embodiment, the reaction formula of Compound 2 is as follows:

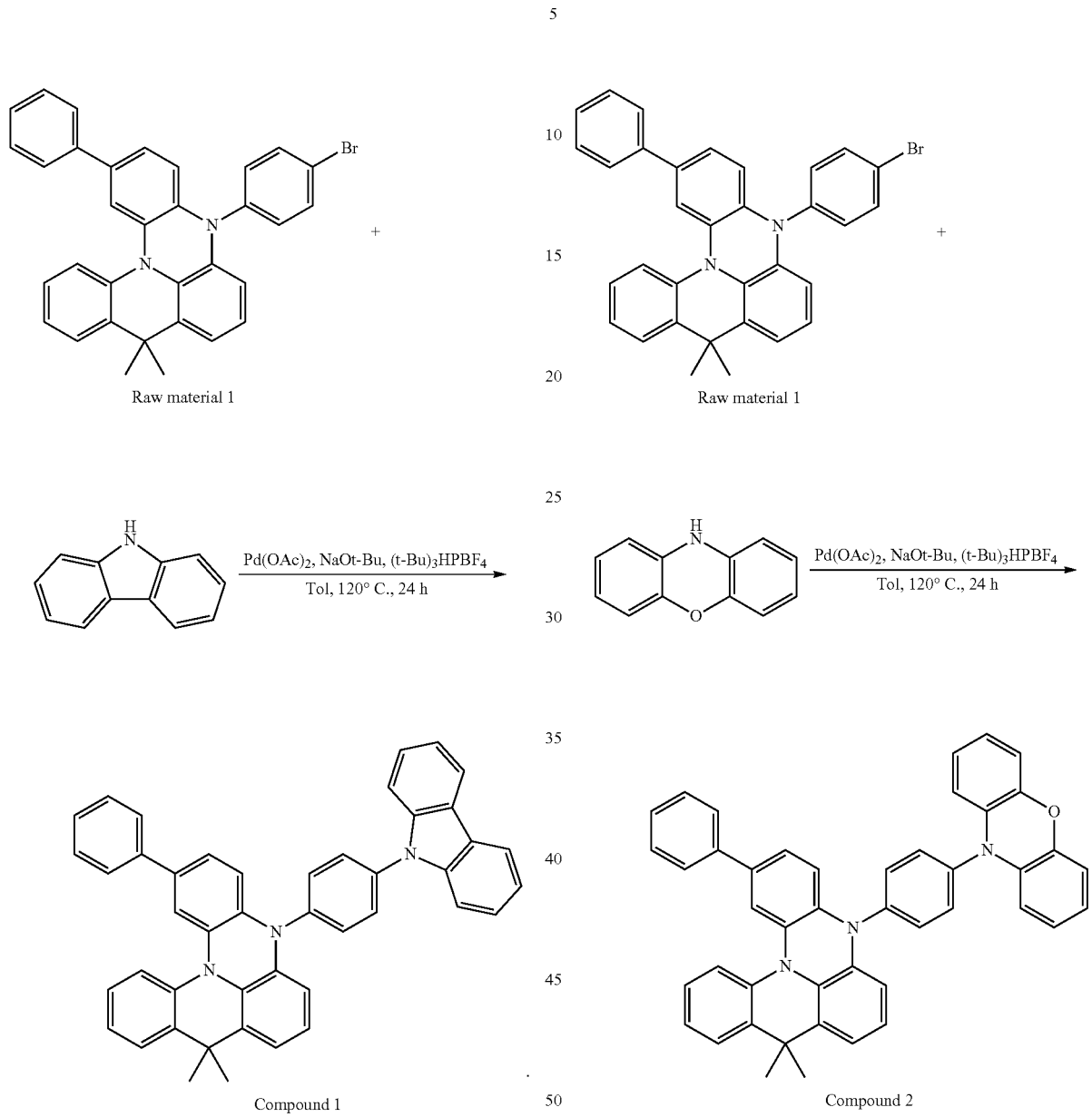

In this embodiment, the steps of the method of preparing Compound 1 are as follows, for example. Raw material 1 (2.64 g, 5 mmol), carbazole (1.00 g, 6 mmol), and palladium acetate (45 mg, 0.2 mmol) and tri-tert-butyl phosphine tetrafluoroborate (0.17 g, 0.6 mmol) were added to a 250 mL two-neck bottle, followed by addition of NaOt-Buu (0.58 g, 6 mmol) in a glove box. In an argon atmosphere, 100 mL of toluene that has been dewatered and deoxygenated was injected for reaction at 120° C. for 24 hours. After cooling to room temperature, the reaction solution was poured into 200 mL ice water, extracted three times with dichloromethane. The organic phases of the extract were combined, spun into silica gel, and isolated and purified by column chromatography (dichloromethane:n-hexane, v:v is 1:5) to obtain 2.0 g of white powder, MS (EI) m/z: [M]+: 615.24, with a yield of 65%.

In this embodiment, the steps of the method of preparing Compound 2 are as follows, for example. Raw material 1 (2.64 g, 5 mmol), phenoxazine (1.10 g, 6 mmol), and palladium acetate (45 mg, 0.2 mmol) and tri-tert-butyl phosphine tetrafluoroborate (0.17 g, 0.6 mmol) were added to a 250 mL two-neck bottle, followed by addition of NaOt-Buu (0.58 g, 6 mmol) in a glove box. In an argon atmosphere, 100 mL of toluene that has been dewatered and deoxygenated was injected for reaction at 120° C. for 24 hours. After cooling to room temperature, the reaction solution was poured into 200 mL ice water, extracted three times with dichloromethane. The organic phases of the extract were combined, spun into silica gel, and isolated and purified by column chromatography (dichloromethane:n-hexane, v:v is 1:5) to obtain 2.2 g of white powder, MS (EI) m/z: [M]+: 631.21, with a yield of 70%.

In this embodiment, the reaction formula of Compound 3 is as follows:

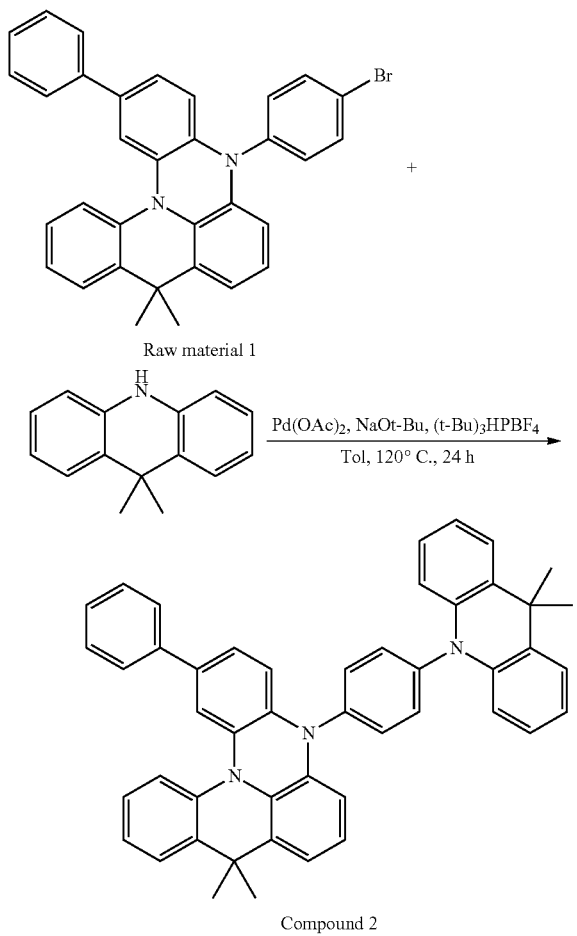

Raw material 1

Compound 2

In this embodiment, the steps of the method of preparing Compound 3 are as follows, for example. Raw material 1 (2.64 g, 5 mmol), 9,9'-dimethylacridine (1.26 g, 6 mmol), and palladium acetate (45 mg, 0.2 mmol) and tri-tert-butyl phosphine tetrafluoroborate (0.17 g, 0.6 mmol) were added to a 250 mL two-neck bottle, followed by addition of NaOt-Buu (0.58 g, 6 mmol) in a glove box. In an argon atmosphere, 100 mL of toluene that has been dewatered and deoxygenated was injected for reaction at 120° C. for 24 hours. After cooling to room temperature, the reaction solution was poured into 200 mL ice water, extracted three times with dichloromethane. The organic phases of the extract were combined, spun into silica gel, and isolated and purified by column chromatography (dichloromethane:n-hexane, v:v is 1:5) to obtain 2.3 g of white powder, MS (EI) m/z: [M]+: 657.24, with a yield of 70%.

In the embodiments of the present invention, by adding other electron-donating groups on the basis of a phenazine-fused acridine structure, organic compounds with high mobility are obtained, which enhance display performance of a display device.

An embodiment of the present invention also provides a display panel 100, which includes a light-emitting device layer 500, and the light-emitting device layer 500 includes any one of the above-mentioned organic compounds or the organic compound produced by any one of the above-mentioned preparation methods.

Embodiments of the present invention are based on the structure of phenazine-fused acridine, combined with other groups to obtain organic compounds with high mobility, thus enhancing the display efficiency of the display device.

The technical scheme of the present invention will now be described in conjunction with specific embodiments.

The display panel 100 includes a substrate 200, an array substrate 300 located on the substrate 200, a light-emitting device layer 500 located on the array substrate 300, and the light-emitting device layer 500 includes any one of the above-mentioned organic compounds or the organic compounds produced by any one of the above-mentioned preparation methods. Please refer to FIG. 1 for details.

In this embodiment, the structure of the organic compound can be referred to the embodiment of any one of the above-mentioned organic compounds and the embodiment of any one of the above-mentioned methods of making organic compounds, which will not be repeated herein for brevity.

In this embodiment, the array substrate 300 includes an active layer, a first insulating layer located on the active layer, a gate layer located on the first insulating layer, and a second insulating layer located on the gate layer. Two insulating layers, a source-drain layer located on the second insulating layer and a third insulating layer located on the source-drain layer.

In this embodiment, the display panel 100 further includes an anode layer 410 on the side of the array substrate 300, a light-emitting device layer 500 on the anode layer 410, a cathode layer 420 on the light-emitting device layer 500, and, the light outcoupling layer 430 on the cathode layer 420. Please refer to FIG. 1 for details.

In this embodiment, the light-emitting device layer 500 includes a hole injection layer 510 located on the anode layer 410, a hole transport layer 520 located on the hole injection layer 510, and a hole transport layer 520 located on the hole transport layer 520. The electron blocking layer 530, the light-emitting material layer 540 located on the electron blocking layer 530, the hole blocking layer 550 located on the light-emitting material layer 540, the electron transport layer 560 located on the hole blocking layer 550, and the electron injection layer 570 on the electron transport layer 560. Please refer to FIG. 1 for details.

In this embodiment, the material in the light-emitting material layer 540 can be OLED or QLED (quantum dot light-emitting diodes), which is not limited here.

In this embodiment, the anode layer 410 includes a first ITO (Indium Tin Oxide) layer, a silver layer on the first ITO layer, a second ITO layer on the silver layer. The anode layer 410 is a totally reflective electrode, which can improve the light-emitting efficiency of the light-emitting device layer 500.

In this embodiment, the cathode layer 420 is a transparent electrode material or a semi-transparent electrode material, and may include ITO to increase the light-emitting efficiency of the light-emitting device layer 500.

In this embodiment, the light outcoupling layer 430 is used to improve the light-emitting efficiency of the light-emitting device layer 500 and enhance the display effect.

In this embodiment, the hole transport layer 520 includes the organic compound. The organic compound cooperates with the hole transport layer 520, and the hole transport efficiency can be best improved.

Taking

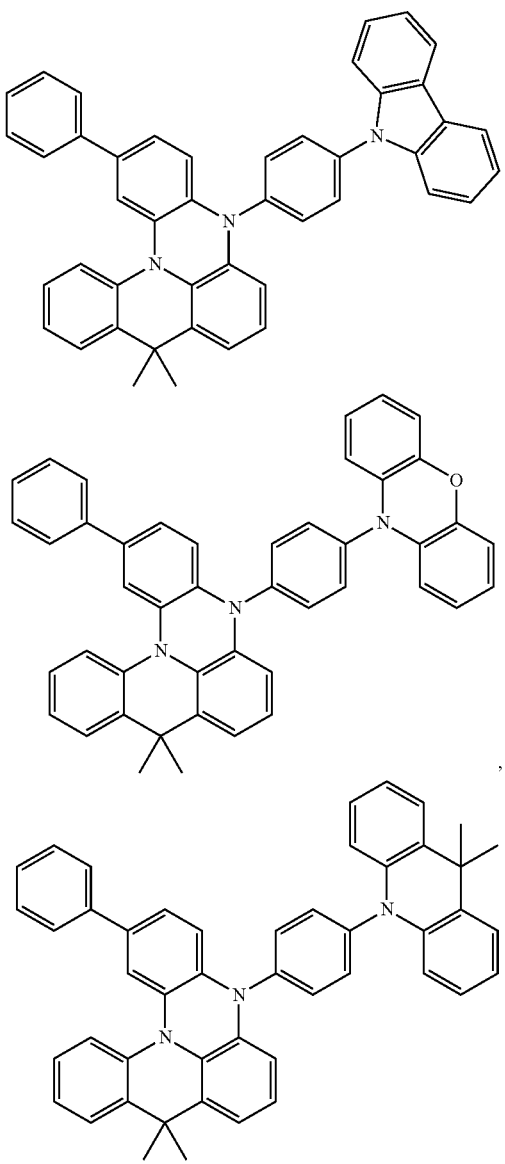

and as examples, the three compounds are named Compound 1, Compound 2 and Compound 3.

In this example, the HOMO electrochemical energy level of Compound 1 is −5.58 eV, and the LUMO electrochemical energy level is −2.53 eV. The HOMO electrochemical energy level of Compound 2 is −5.61 eV, and the LUMO electrochemical energy level is −2.54 eV. The HOMO electrochemical energy level of Compound 3 is −5.66 eV, and the LUMO electrochemical energy level is −2.53 eV. It can be seen that taking the three structures as examples, characterization parameters indicate that the organic compounds can be used as transporting materials.

In this embodiment, Compound 1, Compound 2 and Compound 3 are used in the hole transport layer 520.

In this embodiment, the display panel 100 including the hole transport layer 520 of the Compound 1 has the highest current efficiency of 40.3 cd/A, the red light color coordinates (CIEx, CIEy) of (0.685, 0.290), and the maximum external quantum efficiency of 40.9%.

In this embodiment, the display panel 100 including the hole transport layer 520 of the Compound 2 has the highest current efficiency of 41.1 cd/A, the red light color coordinates (CIEx, CIEy) of (0.685, 0.290), and the maximum external quantum efficiency of 42.3%.

In this embodiment, the display panel 100 including the hole transport layer 520 of the Compound 3 has the highest current efficiency of 40.8 cd/A, the red light color coordinates (CIEx, CIEy) of (0.685, 0.290), and the maximum external quantum efficiency of 41.5%.

In this embodiment, it can be seen from the above characterization data that the organic compounds of the embodiments of the present invention, taking Compound 1, Compound 2, and Compound 3 as examples, can be used in the hole transport layer 520, which have high current efficiency and higher maximum external quantum efficiency, and meanwhile the color standard of red light is more accurate. The organic compounds of the embodiments of the present invention can be used as the materials of the light-emitting device layer 500, especially as materials of the hole transport layer 520, and have the maximum external quantum efficiency of greater than 40%, as well as a very good working efficiency, thus extending the service life of the display panel 100.

In the embodiments of the present invention, by adding other electron-donating groups on the basis of a phenazine-fused acridine structure, organic compounds with high mobility are obtained, which enhance display performance of a display device.

An embodiment of the present invention also provides a display device 10, including any one of the above-mentioned display panel 100.

Figure 2:
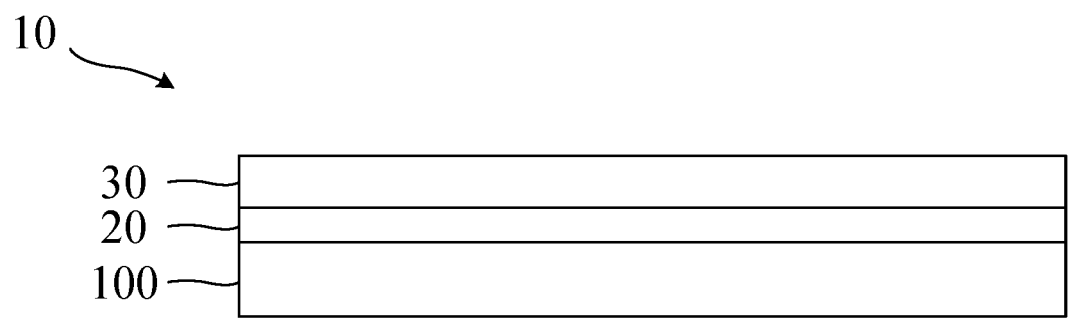
FIG. 2 is a schematic structural diagram of a display device provided by an embodiment of the present invention.

A specific structure of the display panel 100 can be referred to any one of the above-mentioned embodiments of the display panel 100, as well as FIG. 1 and FIG. 2, which will not be repeated herein for brevity.

In this embodiment, the display device 10 also includes an encapsulation layer 20 and a cover layer 30 on the display panel 100. Please refer to FIG. 2 for details.

In the embodiments of the present invention, by adding other electron-donating groups on the basis of a phenazine-fused acridine structure, organic compounds with high mobility are obtained, which enhance display performance of a display device.

Embodiments of the present invention disclose an organic compound, a preparation method thereof, and a display panel. The organic compound is represented by the following general formula:

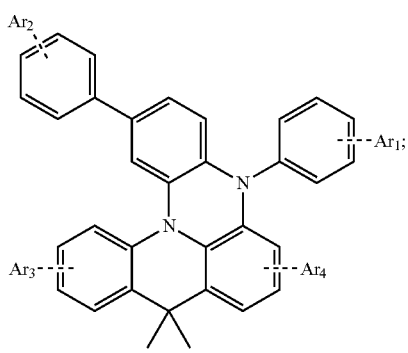

wherein a structure of the organic compound includes at least one of Ar1, Ar2, Ar3. or Ar4, any one of Ar1, Ar2, Ar3 and Ar4 includes any one or a combination of hydrogen, an isotope of hydrogen, an aromatic group, an arylamine group, a heteroarylamine group, and a fused ring group. In the embodiments of the present invention, by adding other electron-donating groups on the basis of a phenazine-fused acridine structure, organic compounds with high mobility are obtained, which enhance display performance of a display device.

It can be understood that for those of ordinary skill in the art, equivalent substitutions or changes can be made according to the technical solutions and inventive concepts of the present application, and all these changes or substitutions shall fall within the protection scope of the appended claims of the present application.

What is claimed is:

1. An organic compound, wherein the organic compound is represented by the following general formula:

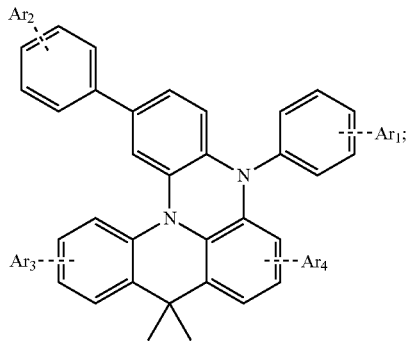

wherein any one of Ar1, Ar2, Ar3, and Ar4 comprises any one or a combination of hydrogen, an isotope of hydrogen, an aromatic group, an arylamine group, a heteroarylamine group, and a fused ring group.

2. The organic compound according to claim 1, wherein any one of Ar1, Ar2, Ar3, and Ar4 comprises any one or a combination of protium, deuterium, tritium, an aromatic group with 6 to 60 carbon atoms, an arylamine group with 6 to 60 carbon atoms, a heteroarylamine group with 6 to 60 carbon atoms, and a fused ring group with 10 to 60 carbon atoms.

3. The organic compound according to claim 2, wherein any one of Ar1, Ar2, Ar3, and Ar4 is an axisymmetric group containing a benzene ring.

4. The organic compound according to claim 3, wherein any one of Ar1, Ar2, Ar3, and Ar4 is any one or a combination of the following groups:

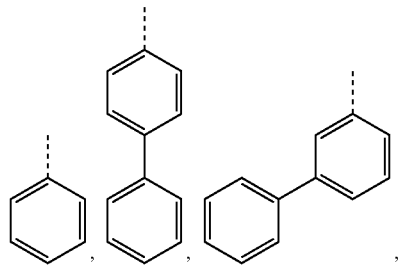

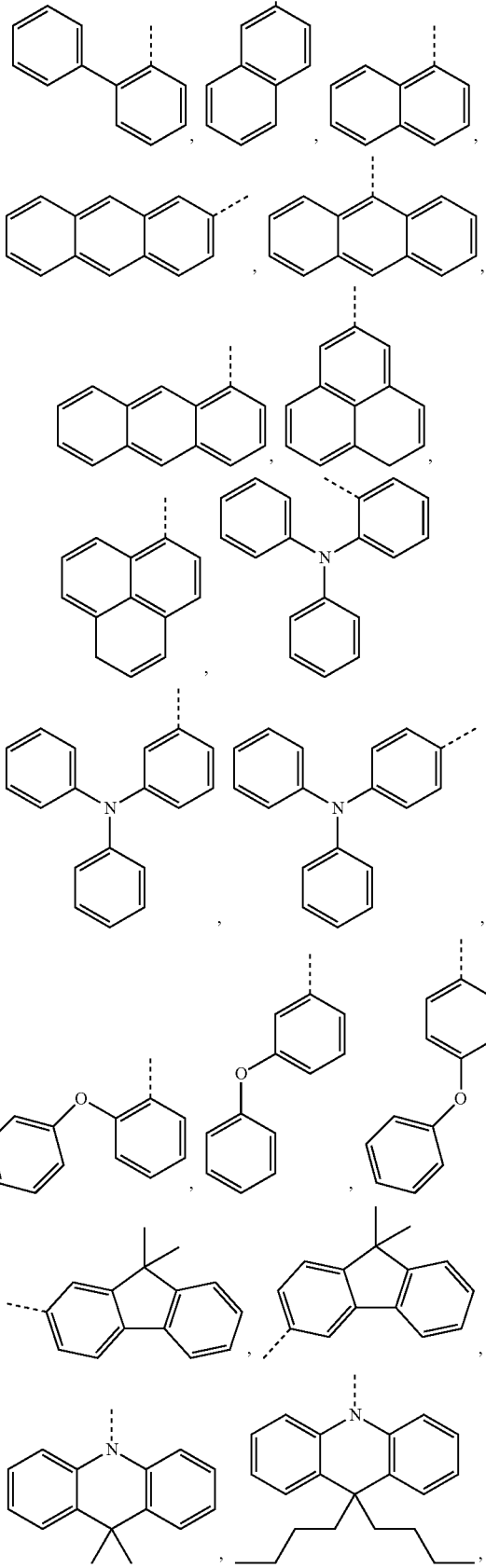

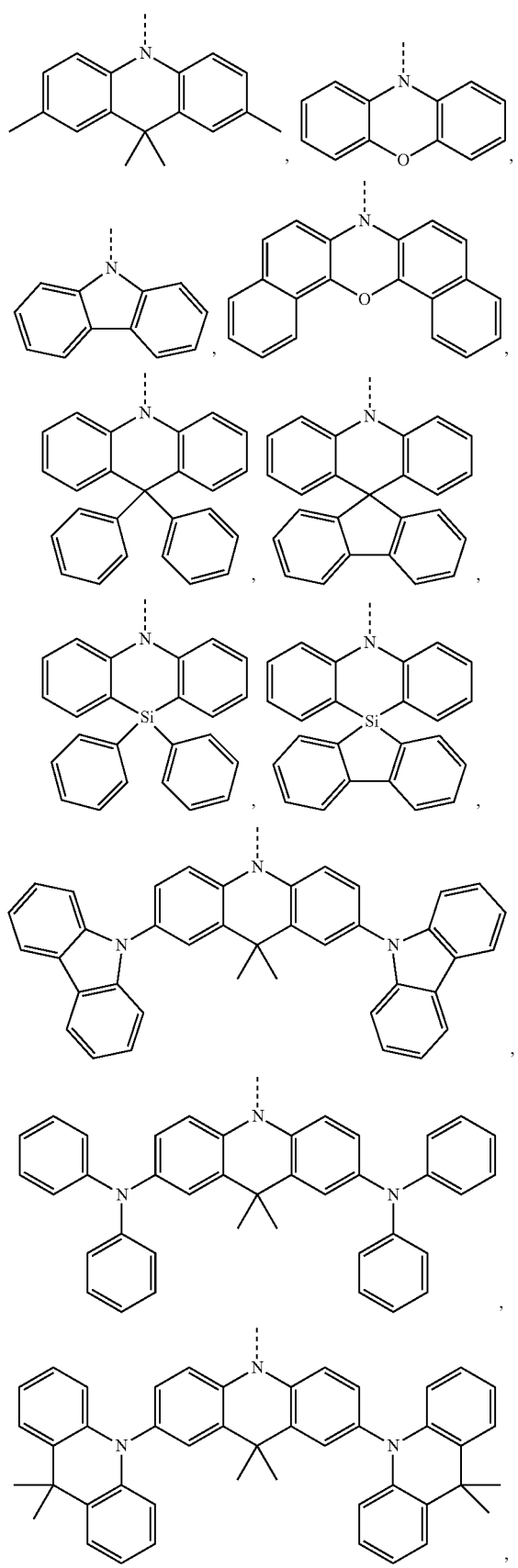

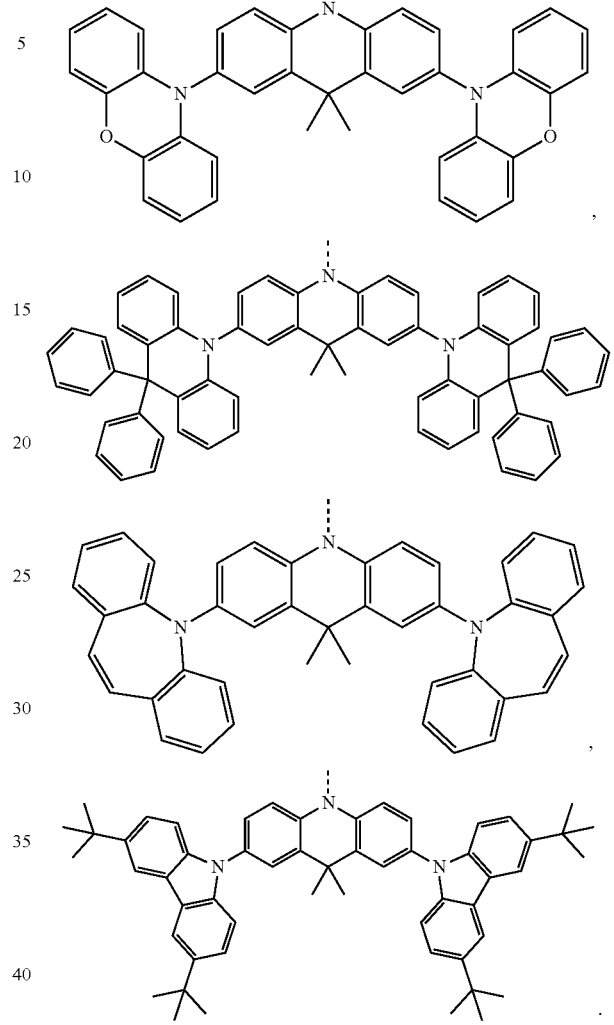

5. The organic compound according to claim 2, wherein the aromatic group comprises an oxygen-containing aromatic group or a silicon-containing aromatic group, the arylamine group comprises an oxygen-containing arylamine group or a silicon-containing arylamine group, and the fused ring group comprises any one of naphthalene, anthracene, and pyrene.

6. The organic compound according to claim 5, wherein any one of Ar1, Ar2, Ar3, and Ar4 is any one or a combination of the following groups:

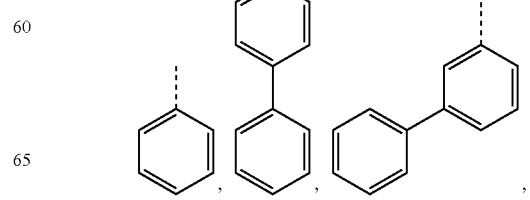

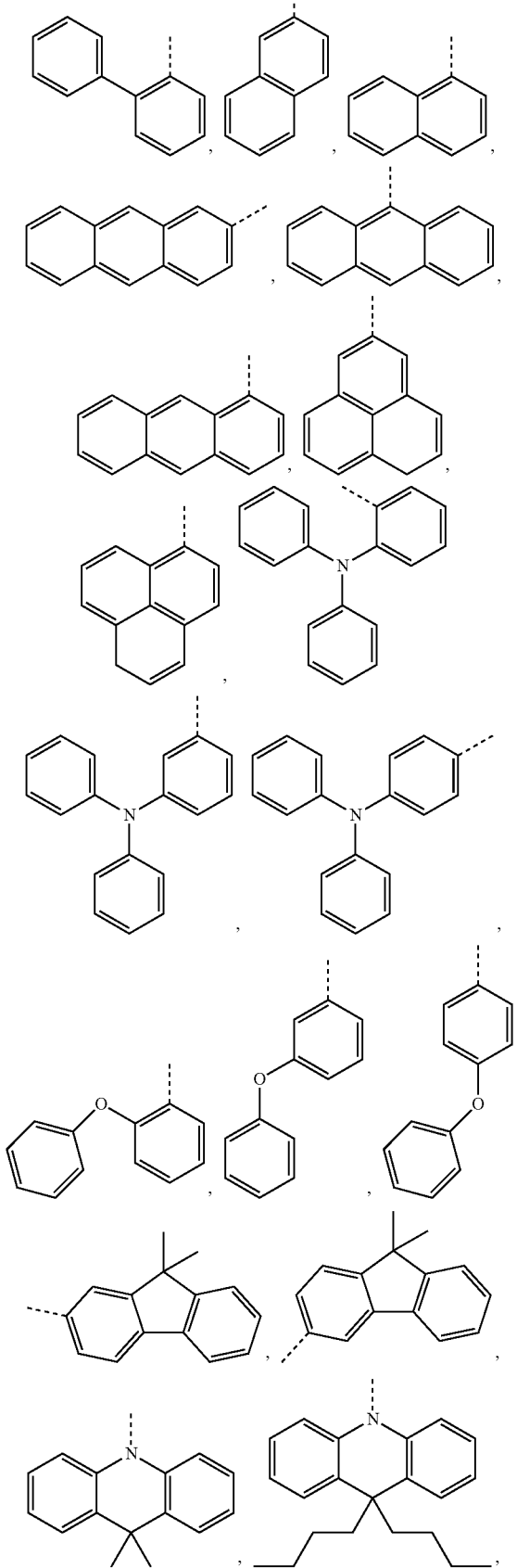
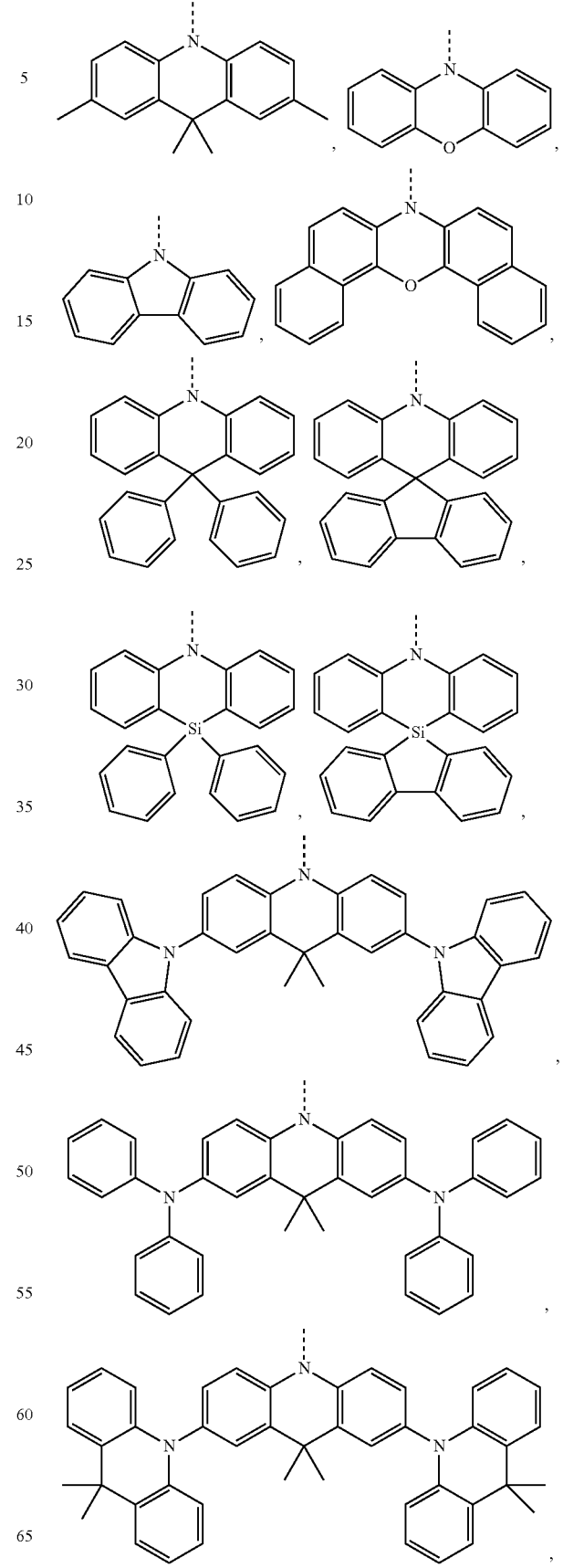

-continued
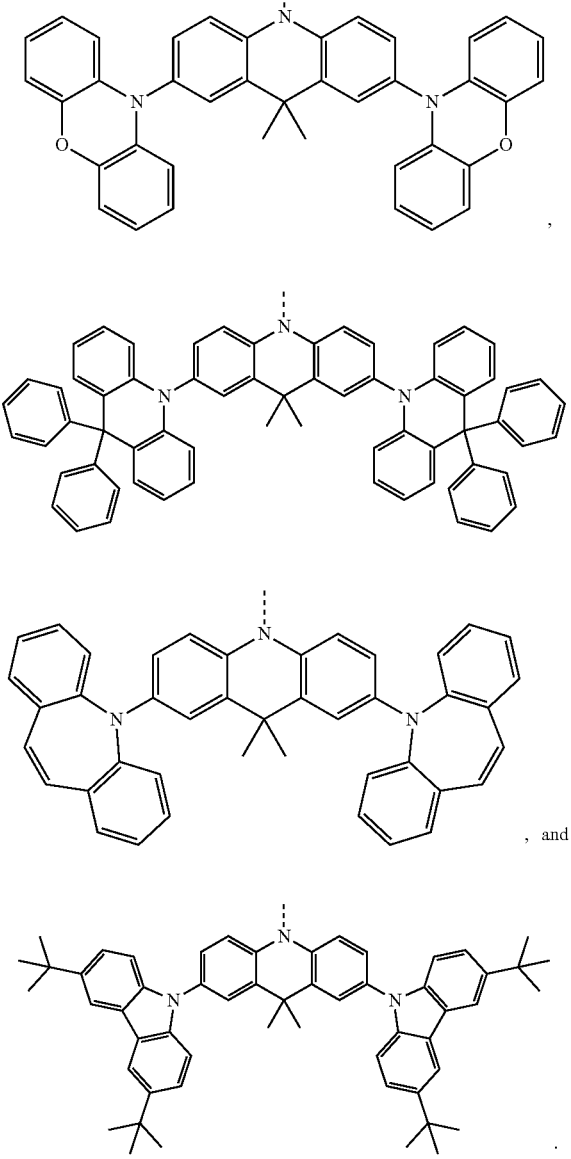
7. The organic compound according to claim 1, wherein a structural formula of the organic compound is:
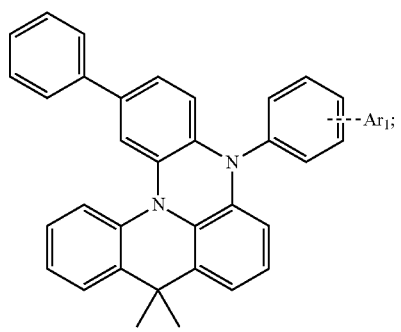
wherein Ar1 is any one of an aromatic group, an arylamine group, or a heteroarylamine group.
8. The organic compound according to claim 7, wherein Ar1 is any one of the following groups:
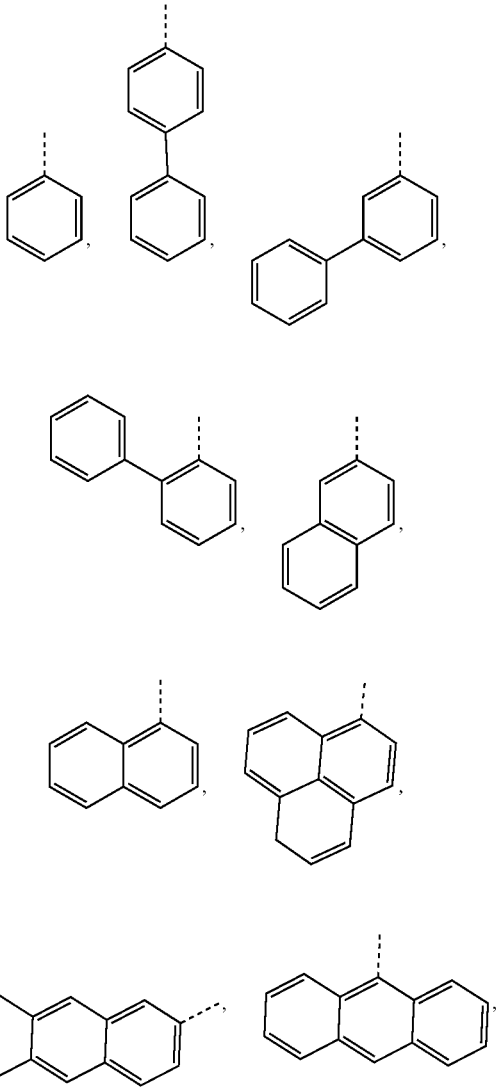
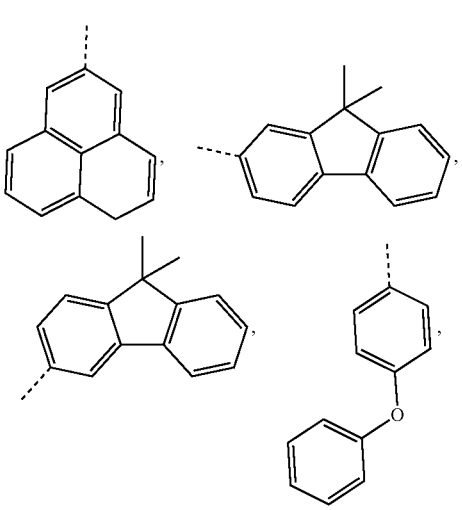

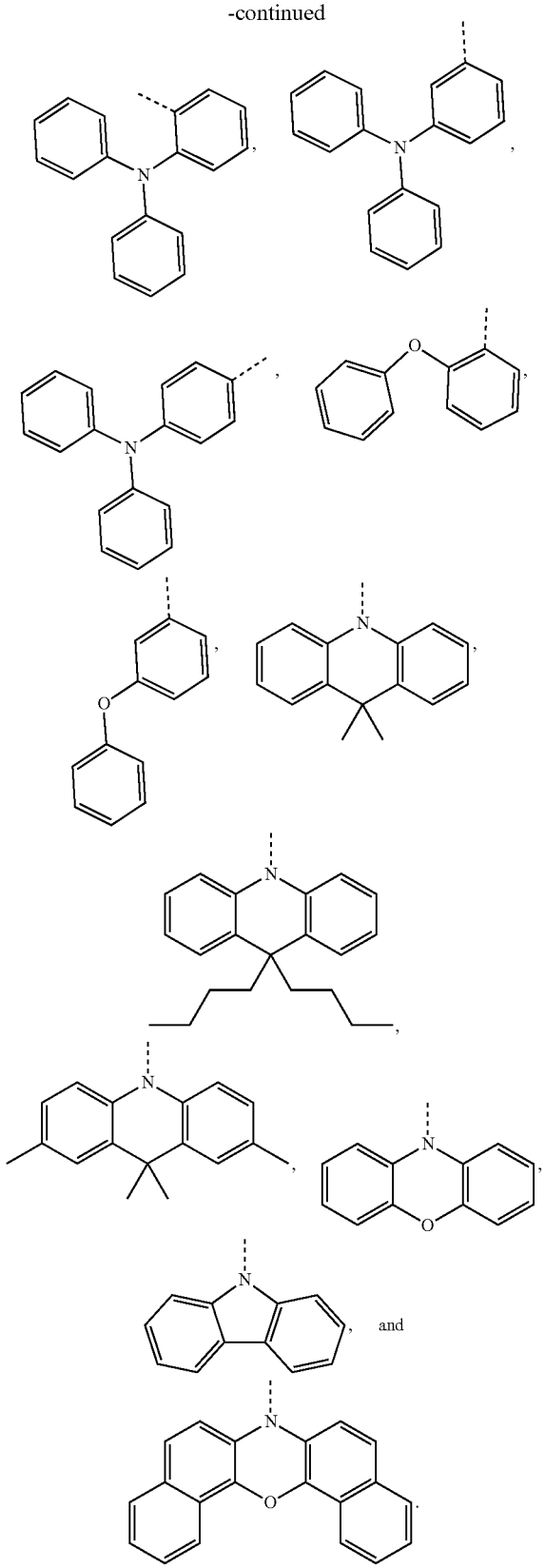
9. The organic compound according to claim 1, wherein a structure of the organic compound comprises any one or a combination of the following:
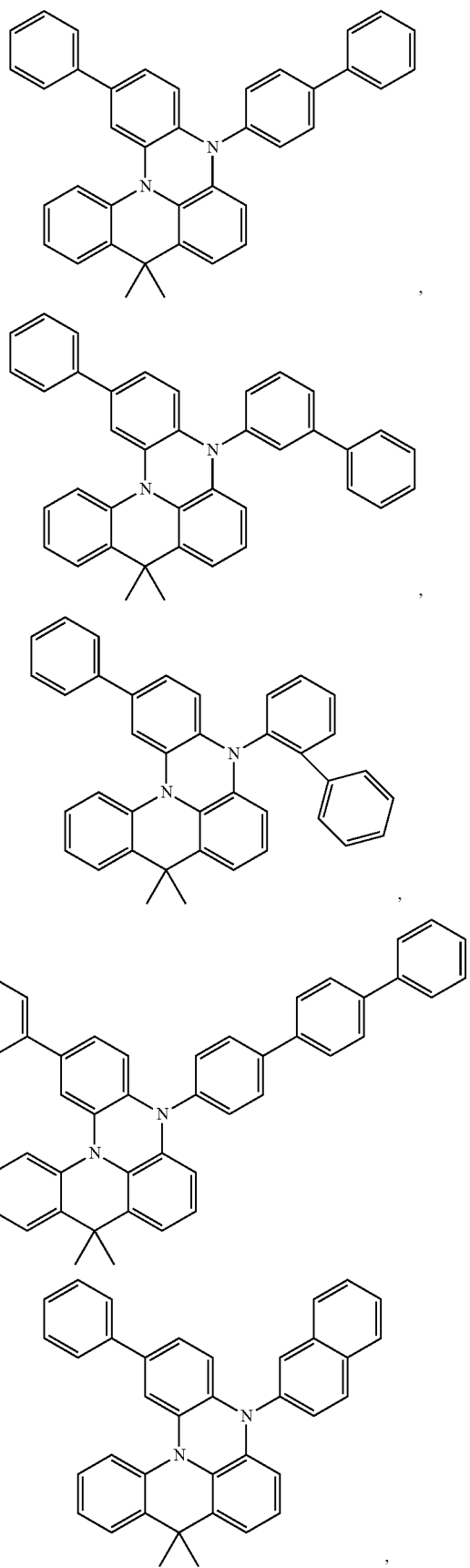

73
-continued
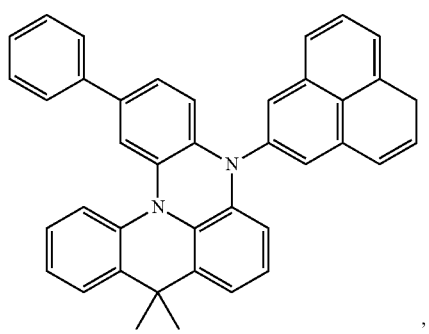
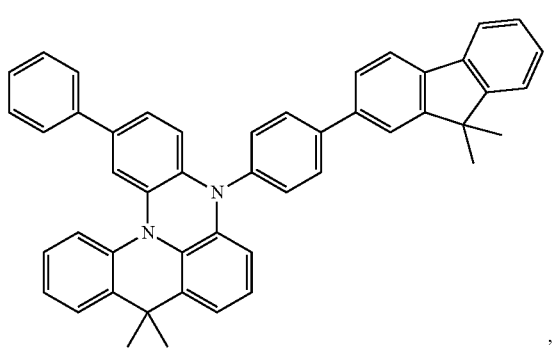
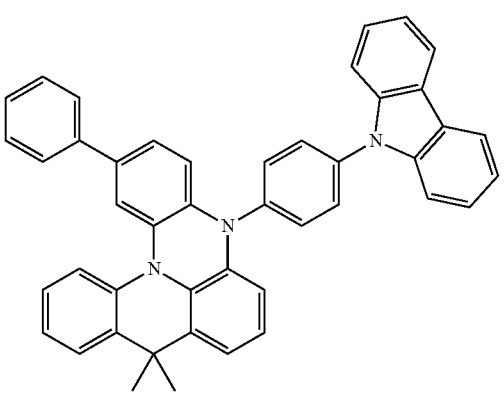
74
-continued
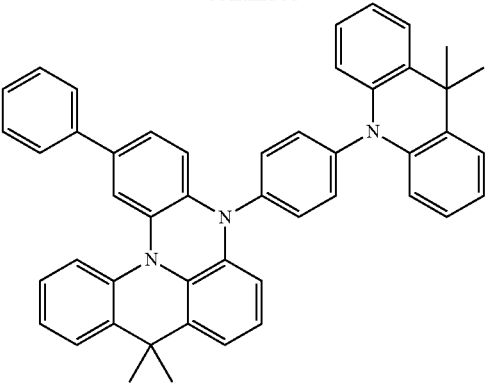
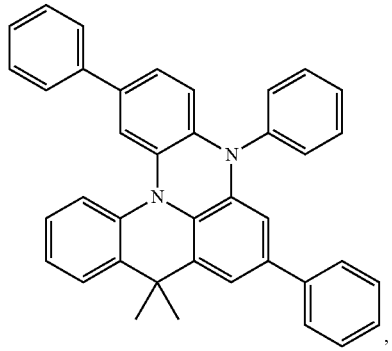
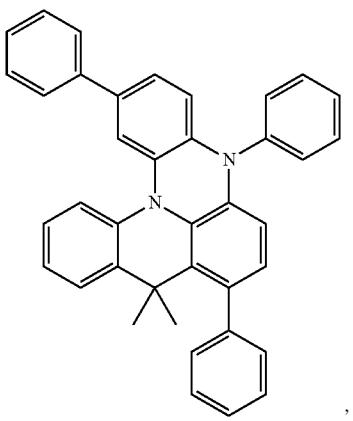

75
-continued
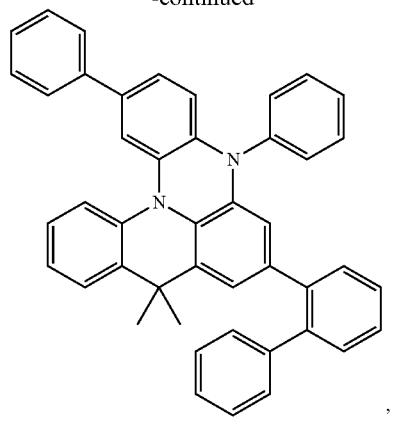
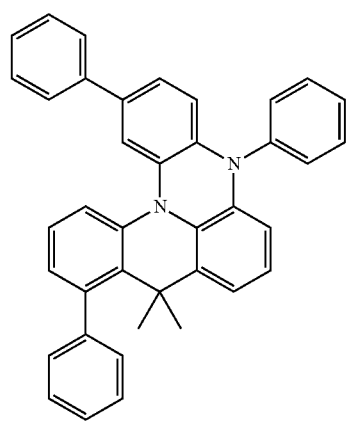
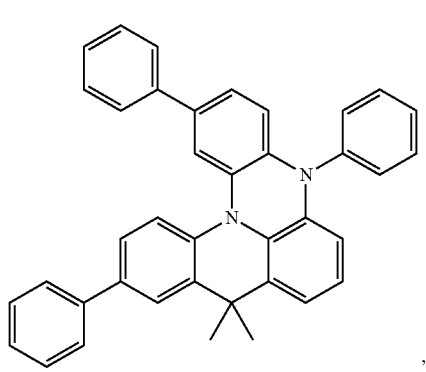
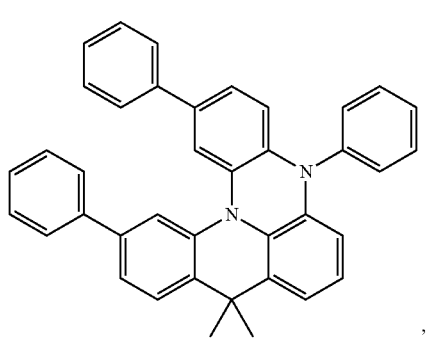
76
-continued
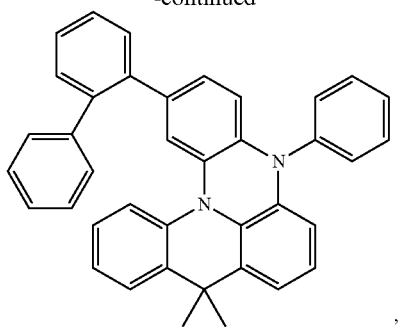
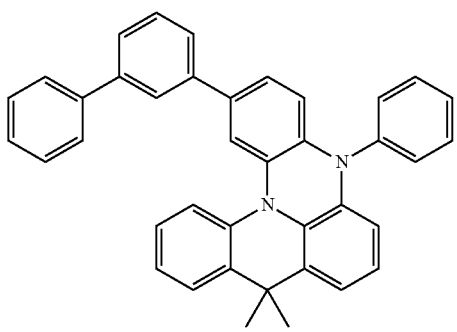
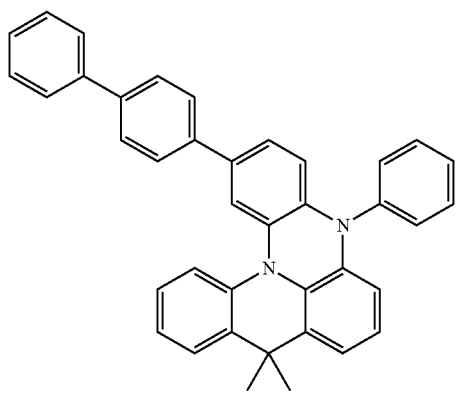
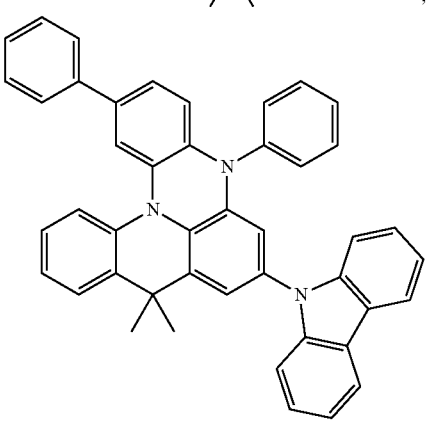, and
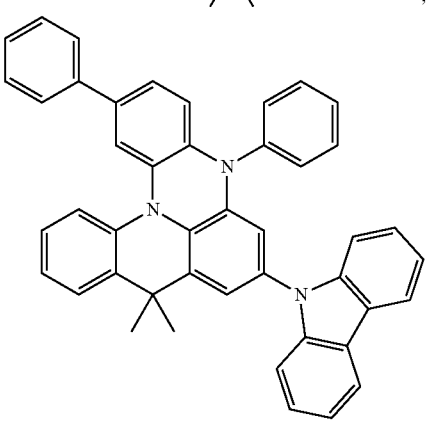
10. A method of preparing an organic compound, which comprises:
mixing a first material and a second material to form the organic compound, and the organic compound is represented by the general formula (1):

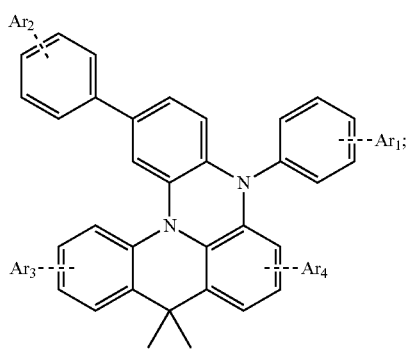

the first material is represented by the general formula (2):

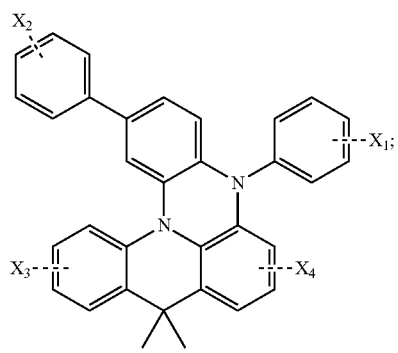

wherein the second material comprises any one or a combination of an aromatic group, an arylamine group, a heteroarylamine group, and a fused ring group; each of X1, X2, X3, and X4 is halogen; a structure of the first material comprises at least one of X1, X2, X3, and X4; and any one of Ar1, Ar2, Ar3, and Ar4 comprises any one or a combination of hydrogen, an isotope of hydrogen, an aromatic group, an arylamine group, a heteroarylamine group, and a fused ring group.

11. The method of preparing the organic compound according to claim 10, wherein a molar ratio of the first material to the second material is 1:1 to 1:3.

12. A display panel, comprising a light-emitting device layer, the light-emitting device layer comprising an organic compound, and the organic compound is represented by the following general formula:

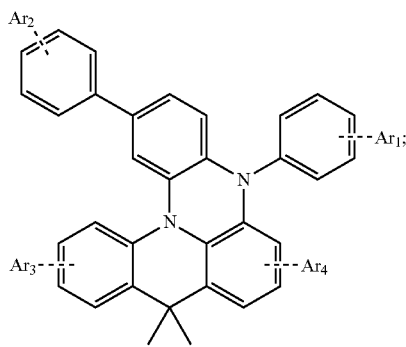

wherein any one of Ar1, Ar2, Ar3, and Ar4 comprises any one or a combination of hydrogen, an isotope of hydrogen, an aromatic group, an arylamine group, a heteroarylamine group, and a fused ring group.

13. The display panel according to claim 12, wherein any one of Ar1, Ar2, Ar3, and Ar4 comprises any one or a combination of protium, deuterium, tritium, an aromatic group with 6 to 60 carbon atoms, an arylamine group with 6 to 60 carbon atoms, a heteroarylamine group with 6 to 60 carbon atoms, and a fused ring group with 10 to 60 carbon atoms.

14. The display panel according to claim 13, wherein any one of Ar1, Ar2, Ar3, and Ar4 is an axisymmetric group containing a benzene ring.

15. The display panel according to claim 14, wherein any one of Ar1, Ar2, Ar3, and Ar4 is any one or a combination of the following:

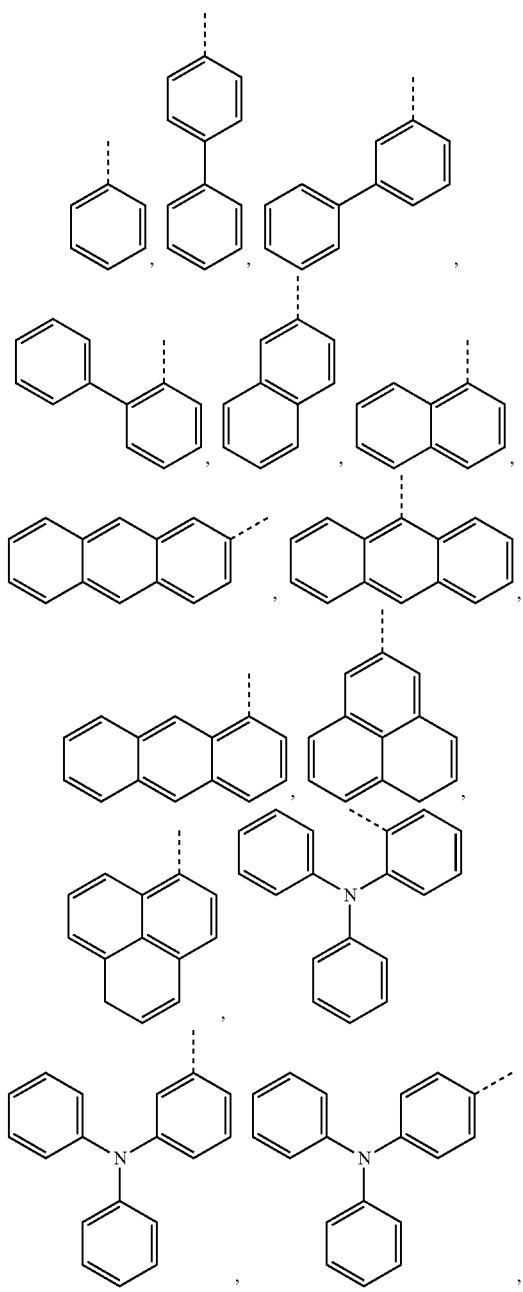

-continued
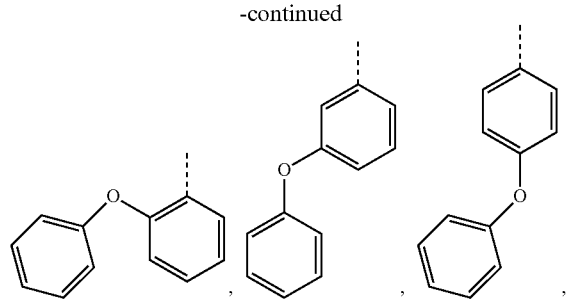
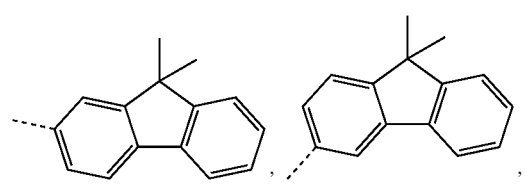
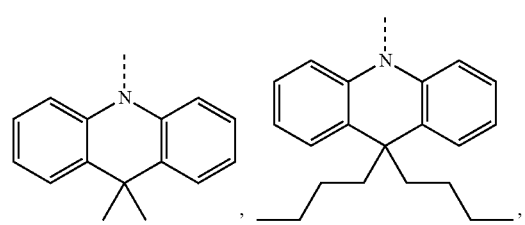
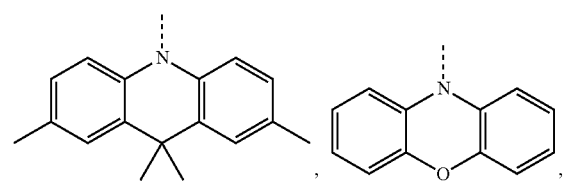
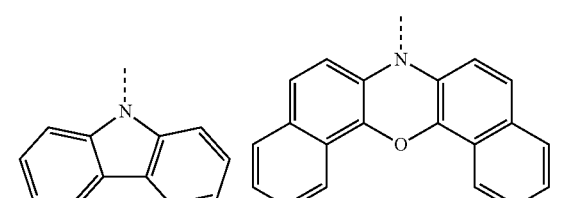
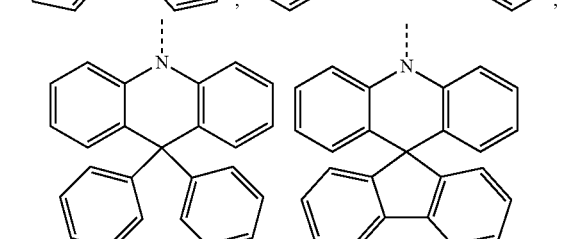
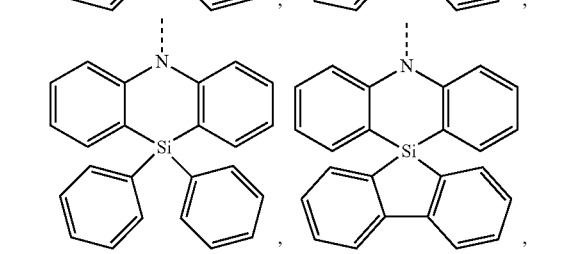
-continued
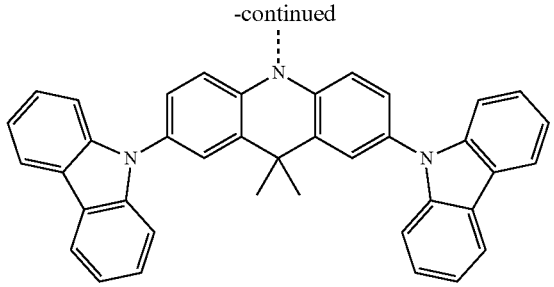
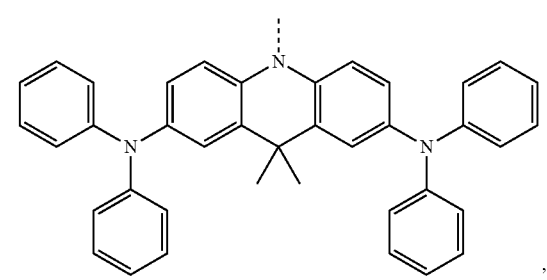
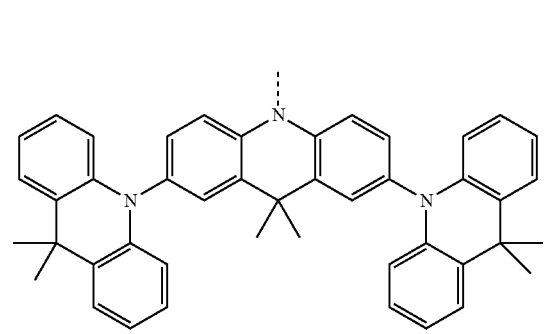
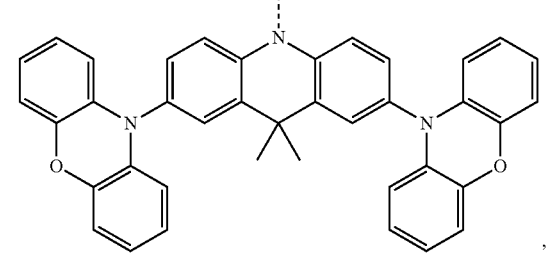
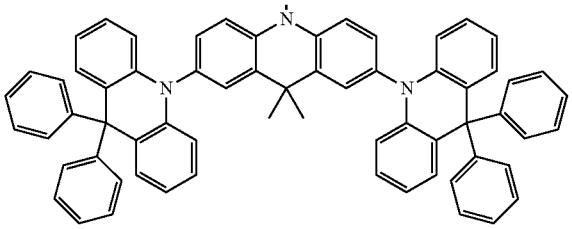
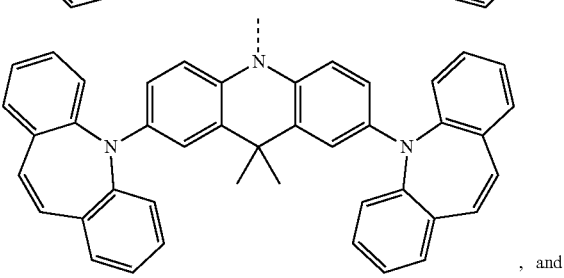
, and

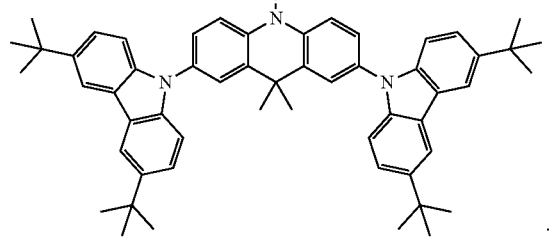

16. The display panel according to claim 13, wherein the aromatic group comprises an oxygen-containing aromatic group or a silicon-containing aromatic group, the arylamine group comprises an oxygen-containing arylamine group or a silicon-containing arylamine group, and the fused ring group comprises any one of naphthalene, anthracene, and pyrene.

17. The display panel according to claim 16, wherein any one of Ar1, Ar2, Ar3, and Ar4 is any one or a combination of the following groups:

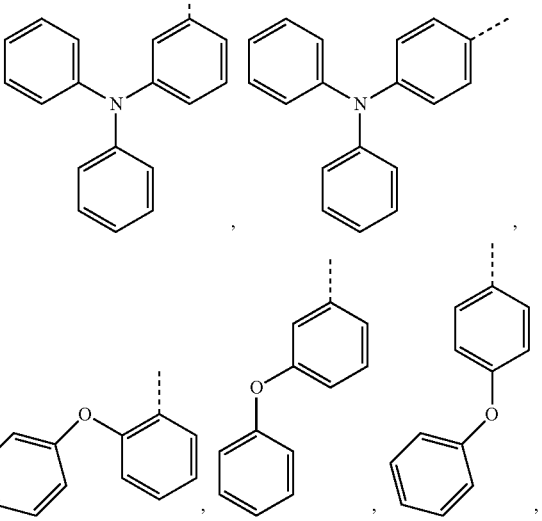

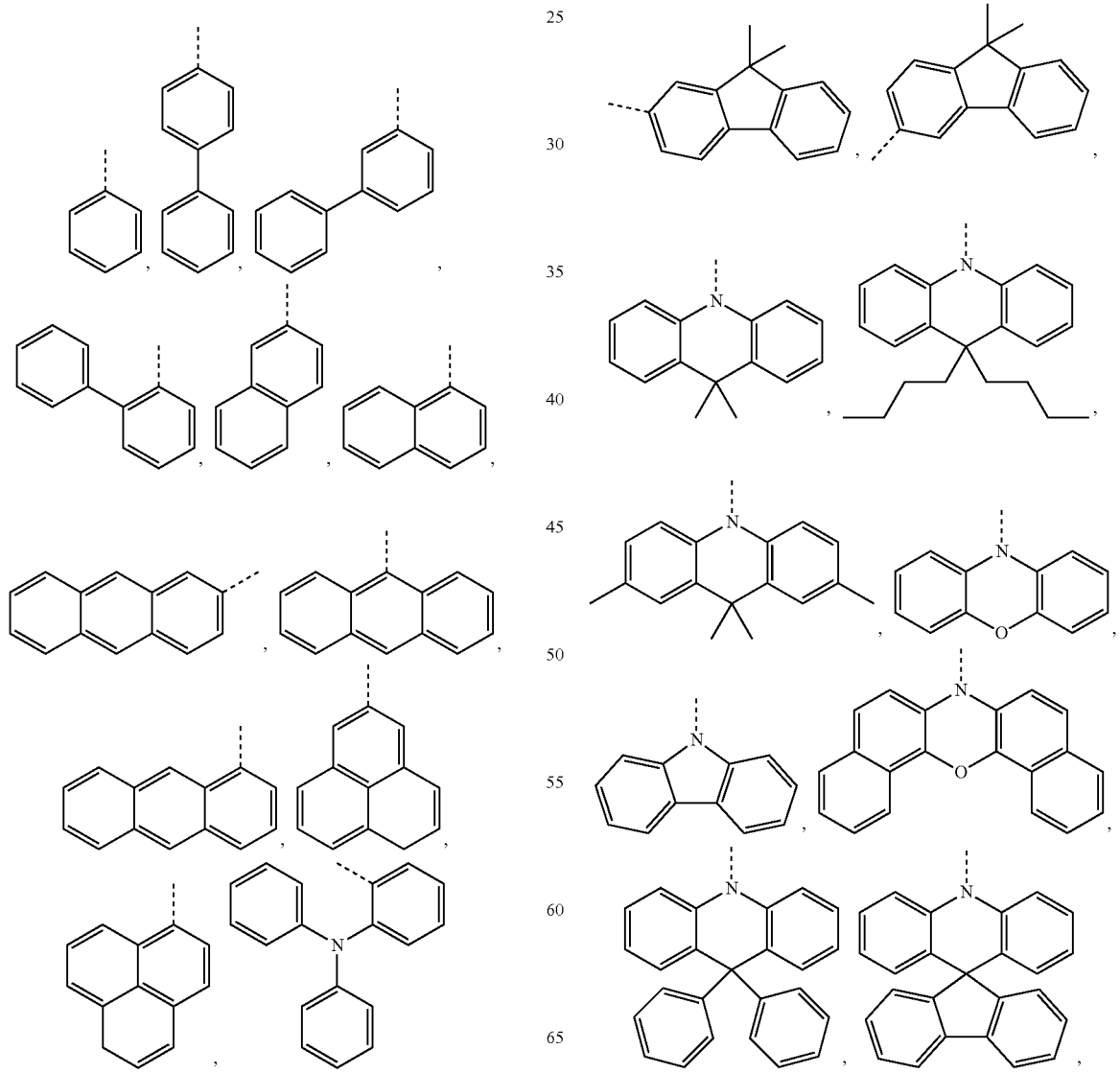

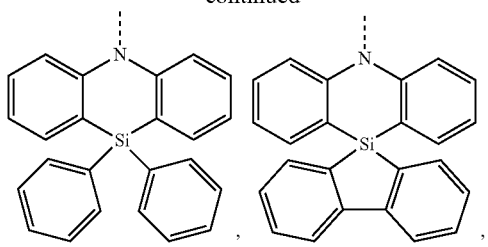
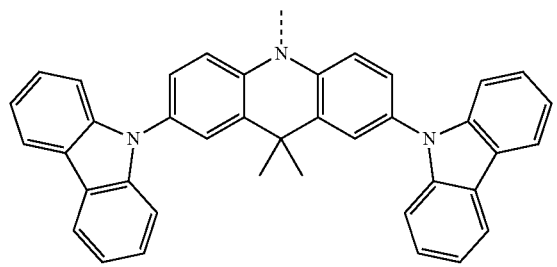
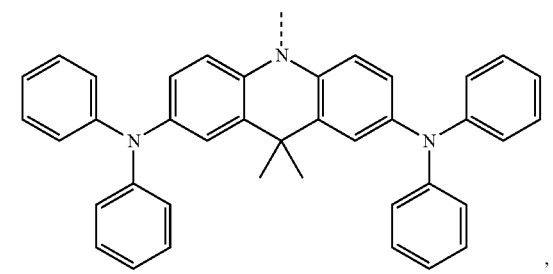
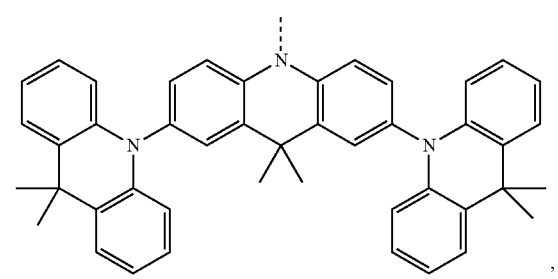
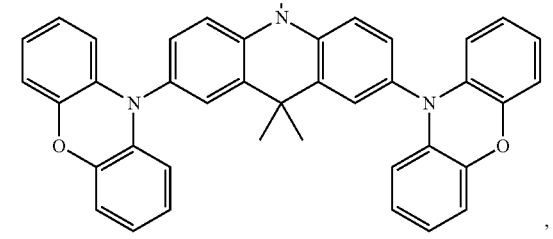
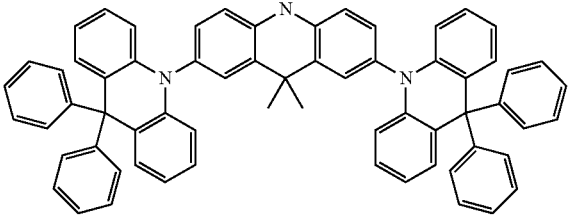
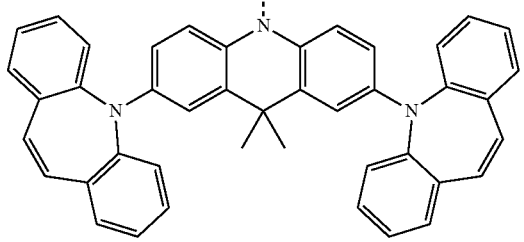
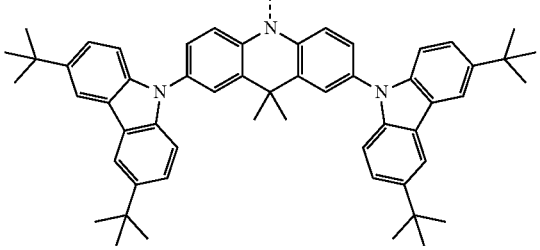
18. The display panel according to claim 12, wherein a structural formula of the organic compound is:
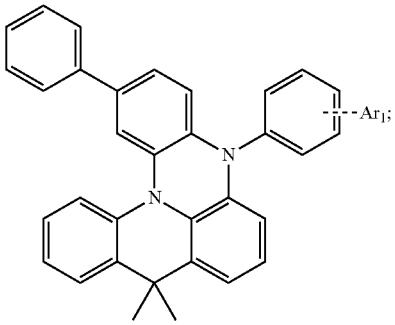
wherein Ar1 is any one of an aromatic group, an arylamine group, and a heteroarylamine group.
19. The display panel according to claim 18, wherein Ar1 is any one of the following groups:
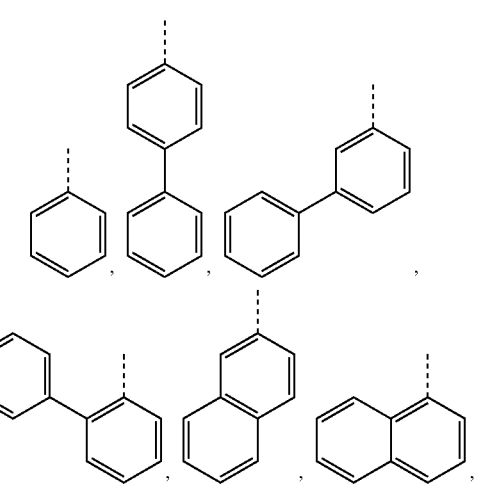

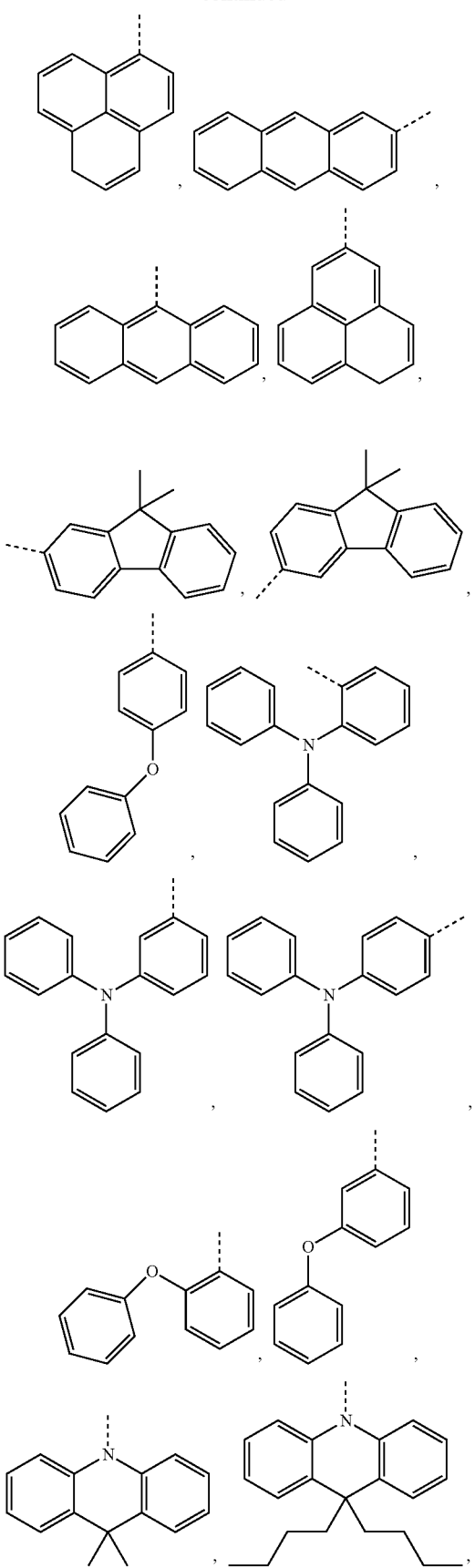
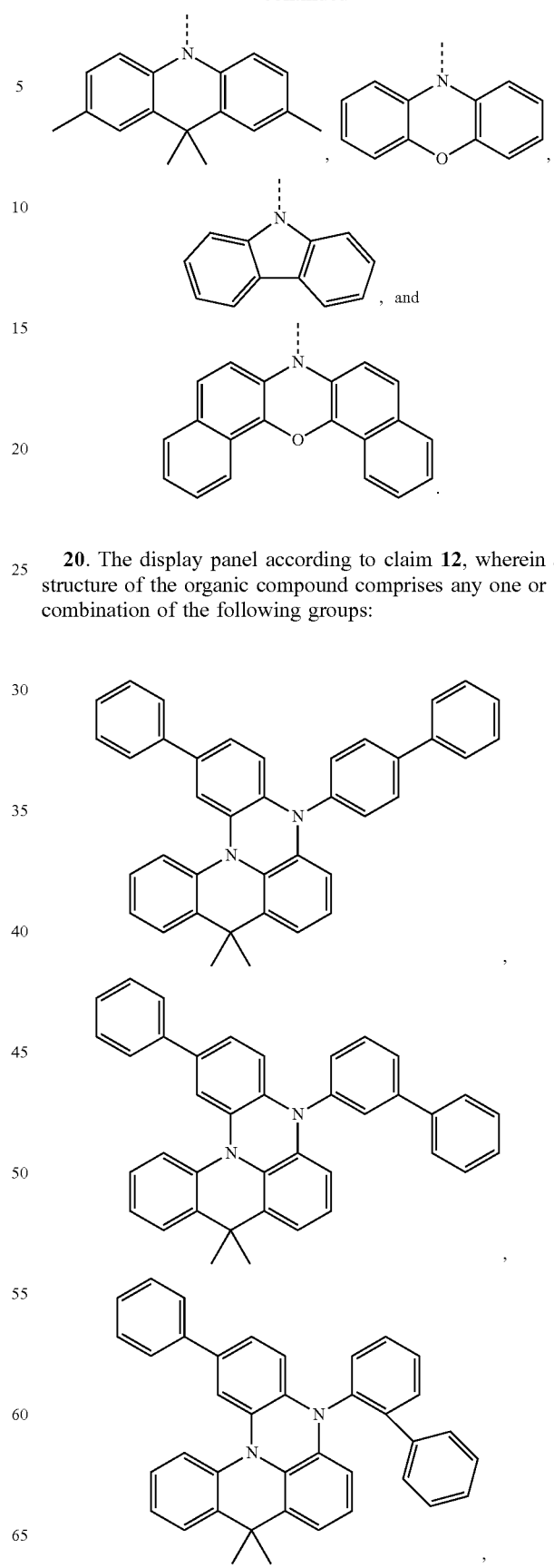
20. The display panel according to claim 12, wherein a structure of the organic compound comprises any one or a combination of the following groups:

87
-continued
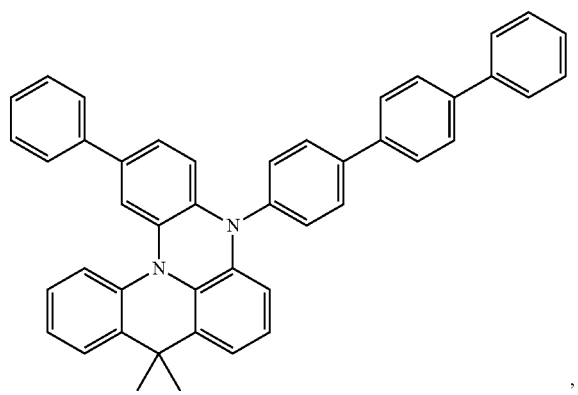
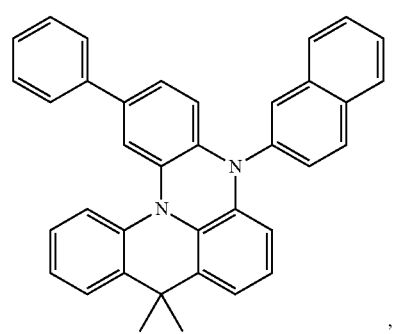
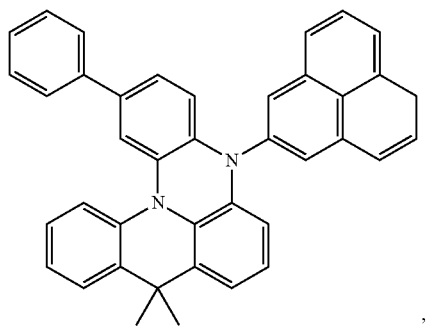
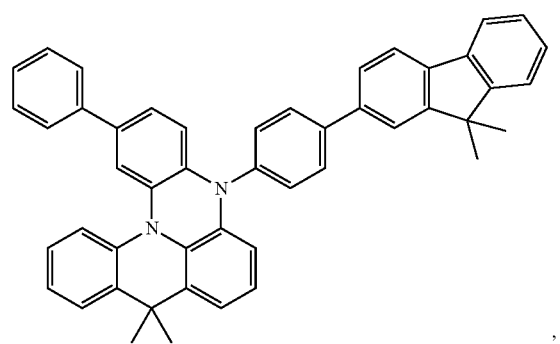
88
-continued
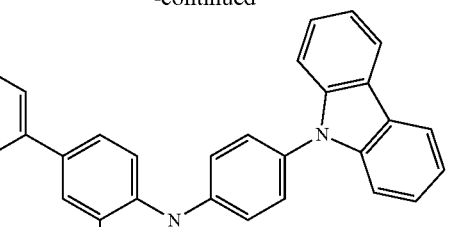
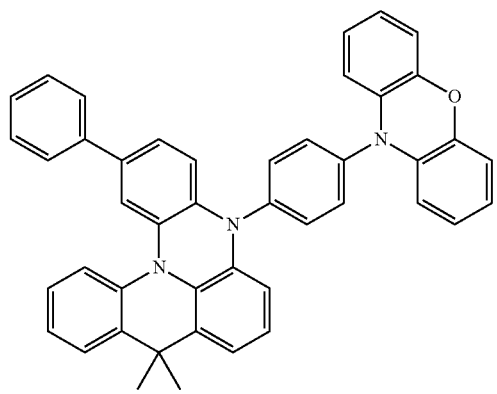
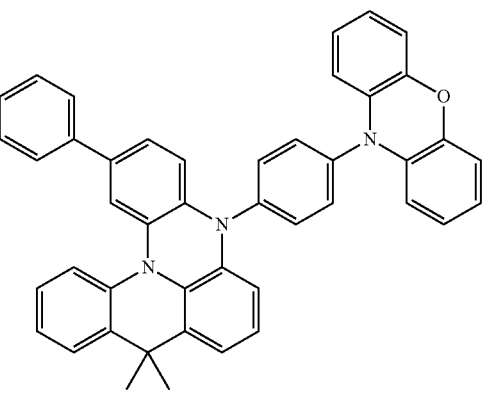
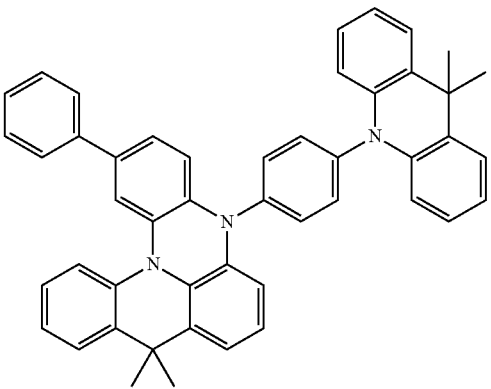
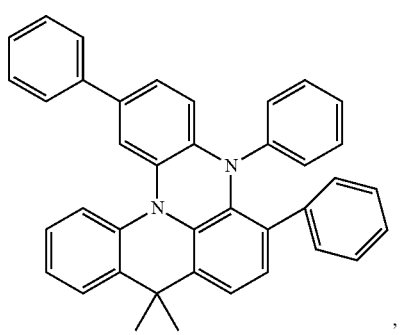

89
-continued
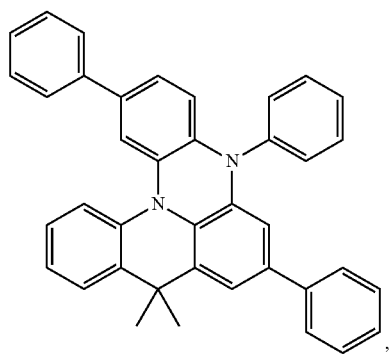
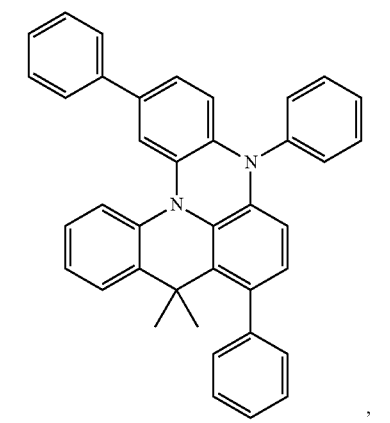
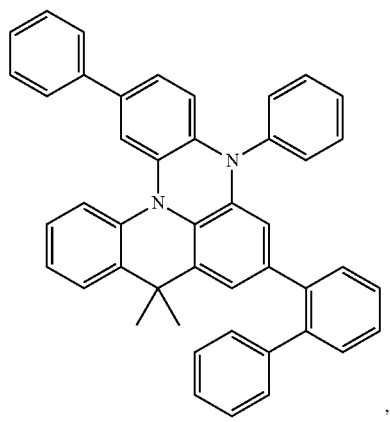
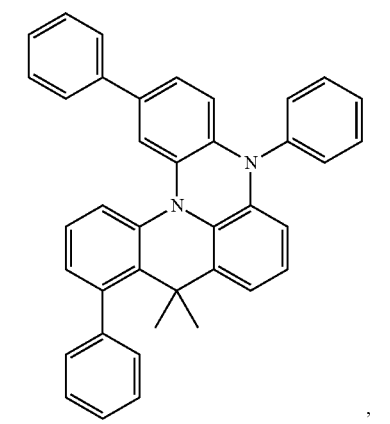
90
-continued
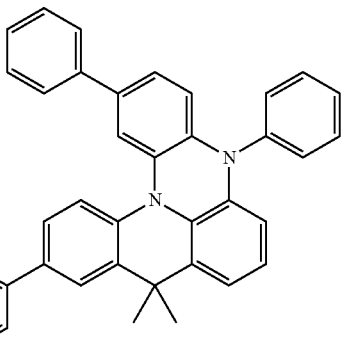
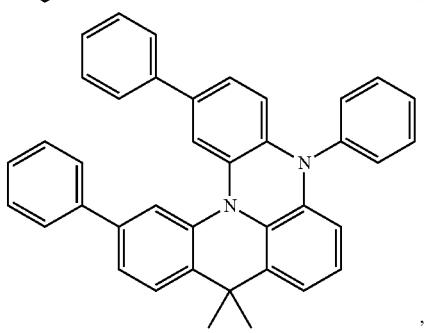
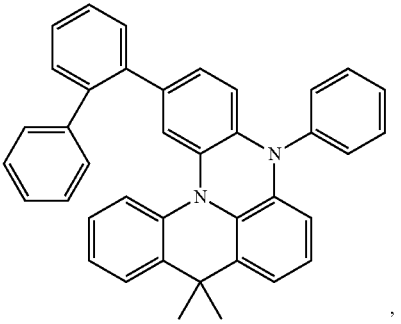
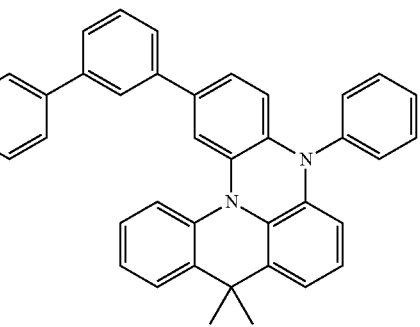
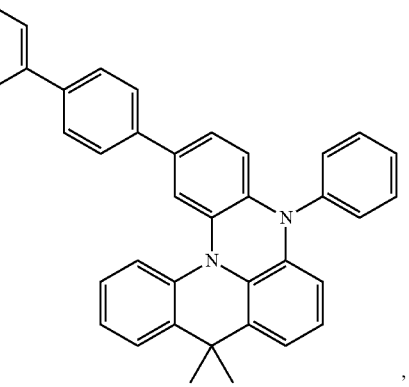
, and -continued
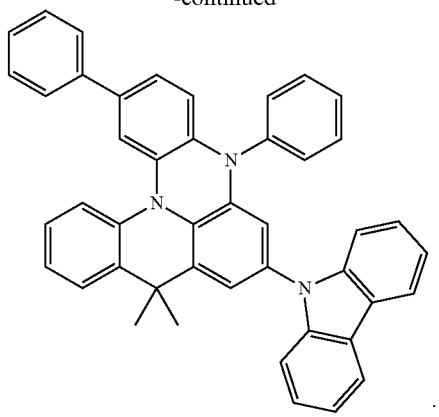
* * * * *